(12) United States Patent
Betts et al.

(10) Patent No.: US 7,119,255 B2
(45) Date of Patent: Oct. 10, 2006

(54) PROMOTER FROM MAIZE PROLAMIN SEED STORAGE PROTEIN AND USES THEREOF

(75) Inventors: Scott Betts, Durham, NC (US); Dale Wayne Skalla, Durham, NC (US); Sandra Lynn Voltrath, Durham, NC (US); Koen Hendrickx, Research Triangle Park, NC (US)

(73) Assignee: Syngenta Participations, AG, Basel (CH)

( * ) Notice: Subject to any disclaimer, the term of this patent is extended or adjusted under 35 U.S.C. 154(b) by 0 days.

(21) Appl. No.: 11/074,522

(22) Filed: Mar. 8, 2005

(65) Prior Publication Data

US 2005/0198712 A1    Sep. 8, 2005

Related U.S. Application Data

(60) Provisional application No. 60/551,286, filed on Mar. 8, 2004.

(51) Int. Cl.
  *C12N 15/82*   (2006.01)
  *C12N 15/90*   (2006.01)
  *A01H 5/00*    (2006.01)
  *C07H 21/04*   (2006.01)

(52) U.S. Cl. .................. 800/287; 536/24.1; 435/419; 435/468; 435/320.1; 435/471; 800/293; 800/294

(58) Field of Classification Search ............ None
  See application file for complete search history.

(56) References Cited

OTHER PUBLICATIONS

Puchta H. Gene replacement by homologous recombination in plants. (2002) PMB vol. 48, pp. 173-182.*
GENBANK® Accession No. AAL16979: amino acid sequence of 50 kD gamma zein from *Zea mays*.
GENBANK® Accession No. AF371263: *Zea mays* 50 kD gamma zein mRNA, complete coding sequence.
GENBANK® Accession No. AI812147: 605087H03.y1 605-Endosperm CDNA library from Schmidt lab *Zea mays* cDNA, mRNA sequence.
Vitale et al.: "Reduced Soluble Proteins Associated with Maize Endosperm Protein Bodies", *J. of Experimental Botany*, 33 (134): 439-448, Jun. 1982.
Wallace et al., "New Methods for Extraction and Quantitation of Zeins Reveal a High Content of γ-Zein in Modified *opaque*-2 Maize", *Plant Physiol.*, 92: 191-196, 1990.
Torrent et al., "Lysine-rich modified γ-zeins accumulate in protein bodies of transiently transformed maize endosperms", *Plant Molecular Biology*, 34: 139-149, 1997.
Prat et al., "Multiple variability in the sequence of a family of maize endosperm proteins", *Gene*, 52: 41-49, 1987.
Boronat et al., "Isolation and Sequencing of a 28kD Glutelin-2 from Maize. Common Elements in the 5' Flanking Regions Among Zein and Glutelin Genes", *Plant Science*, 47: 95-102, 1986.
Invitation to pay additional fees and, where applicable, protest fee, corresponding to application No. PCT/US05/07583 dated Mar. 7, 2006.
Coleman et al., "A defective signal peptide in the maize high-lysine mutant floury", *Plant Biology*, 92: 6828-6831, Jul. 1995.
Woo Young-Min et al., "Genomics analysis of genes expressed in maize endosperm identifies novel seed proteins and clarifies patterns of zein gene expression", *The Plant Cell*, 13: 2297-2317, Oct. 2001.
Gencore Version 5.1.6, PCT-US05-07583.rnpn, Sep. 14, 2005.
International Search Report and Written Opinion corresponding PCT Appl. No. PCT/US05/07583.
Geli et al. Two structural domains mediate two sequential events in gamma-zein targeting; protein endoplasmic reticulum retention and protein body formation. The Plant Cell, Dec. 1994, vol. 6, pp. 1911-1922.

* cited by examiner

*Primary Examiner*—Ashwin D. Mehta
*Assistant Examiner*—Cathy Kingdon Worley
(74) *Attorney, Agent, or Firm*—Jenkins, Wilson, Taylor & Hunt, P.A.

(57) ABSTRACT

Provided is a nucleotide sequence of a promoter from a gene encoding a 55 kDa maize prolamin family protein. Also provided are methods that utilize the 55 kDa maize prolamin family gene promoter to express heterologous sequences in plants, expression cassettes that include the 55 kDa maize prolamin family gene promoter, and plants transformed with expression cassettes that include the 55 kDa maize prolamin family gene promoter.

25 Claims, 4 Drawing Sheets

SEQUENCE LISTING

<160> NUMBER OF SEQ ID NOS: 18

<210> SEQ ID NO 1
<211> LENGTH: 927
<212> TYPE: DNA
<213> ORGANISM: Zea mays
<220> FEATURE:
<221> NAME/KEY: CDS
<222> LOCATION: (1)..(927)

<400> SEQUENCE: 1

```
atg aag ctg gtg ctt gtg gtt ctt gct ttc att gct tta gta tca agt        48
Met Lys Leu Val Leu Val Val Leu Ala Phe Ile Ala Leu Val Ser Ser
1               5                   10                  15 gtt tct tgt aca cag aca ggc ggc tgc agc tgt ggt caa caa caa agc        96
Val Ser Cys Thr Gln Thr Gly Gly Cys Ser Cys Gly Gln Gln Gln Ser
            20                  25                  30 cat gag cag caa cat cat cca caa caa cat cat cca caa aaa caa caa       144
His Glu Gln Gln His His Pro Gln Gln His His Pro Gln Lys Gln Gln
        35                  40                  45 cat caa cca cca cca caa cat cac cag cag cag caa cac caa caa caa       192
His Gln Pro Pro Pro Gln His His Gln Gln Gln Gln His Gln Gln Gln
    50                  55                  60 caa gtt cac atg caa cca caa aaa cat cag caa caa caa gaa gtt cat       240
Gln Val His Met Gln Pro Gln Lys His Gln Gln Gln Glu Val His
65                  70                  75                  80 gtt caa caa caa caa caa caa ccg cag cac caa caa caa caa caa           288
Val Gln Gln Gln Gln Gln Gln Pro Gln His Gln Gln Gln Gln Gln Gln
                85                  90                  95 caa cag cac caa caa caa cat caa tgt gaa ggc caa caa caa cat cac       336
Gln Gln His Gln Gln Gln His Gln Cys Glu Gly Gln Gln Gln His His
            100                 105                 110 caa caa tca caa ggc cat gtg caa caa cac gaa cag agc cat gag caa       384
Gln Gln Ser Gln Gly His Val Gln Gln His Glu Gln Ser His Glu Gln
        115                 120                 125 cac caa gga cag agc cat gag caa caa cat caa caa caa ttc cag ggt       432
His Gln Gly Gln Ser His Glu Gln Gln His Gln Gln Gln Phe Gln Gly
    130                 135                 140 cat gac aag cag caa caa cca caa cag cct cag caa tat cag cag ggc       480
His Asp Lys Gln Gln Gln Pro Gln Gln Pro Gln Gln Tyr Gln Gln Gly
145                 150                 155                 160 cag gaa aaa tca caa cag caa caa tgt cat tgc cag gag cag caa cag       528
Gln Glu Lys Ser Gln Gln Gln Gln Cys His Cys Gln Glu Gln Gln Gln
                165                 170                 175 act aca agg tgc agc tat aac tac tat agc agt agc tca aat cta aaa       576
Thr Thr Arg Cys Ser Tyr Asn Tyr Tyr Ser Ser Ser Ser Asn Leu Lys
            180                 185                 190 aat tgt cat gaa ttc cta agg cag cag tgc agc cct ttg gta atg cct       624
Asn Cys His Glu Phe Leu Arg Gln Gln Cys Ser Pro Leu Val Met Pro
        195                 200                 205 ttt ctc caa tca cgt ttg ata caa cca agt agc tgc cag gta ttg cag       672
Phe Leu Gln Ser Arg Leu Ile Gln Pro Ser Ser Cys Gln Val Leu Gln
    210                 215                 220 caa caa tgt tgt cat gat ctt agg cag att gag cca caa tac att cac       720
Gln Gln Cys Cys His Asp Leu Arg Gln Ile Glu Pro Gln Tyr Ile His
225                 230                 235                 240 caa gca atc tac aac atg gtt caa tcc ata atc cag gag gag caa caa       768
Gln Ala Ile Tyr Asn Met Val Gln Ser Ile Ile Gln Glu Glu Gln Gln
                245                 250                 255 caa caa cca tgt gag tta tgt gga tct caa caa gct act caa agt gcg       816
Gln Gln Pro Cys Glu Leu Cys Gly Ser Gln Gln Ala Thr Gln Ser Ala
            260                 265                 270 gtg gca atc ttg aca gca gca caa tac cta cca tca atg tgc ggc ttg       864
Val Ala Ile Leu Thr Ala Ala Gln Tyr Leu Pro Ser Met Cys Gly Leu
        275                 280                 285
```

```
tac cac tca tac tac caa aat aat cca tgc agc agc aat gac att agt    912
Tyr His Ser Tyr Tyr Gln Asn Asn Pro Cys Ser Ser Asn Asp Ile Ser
    290                 295                 300 ggt gtt tgc aat tga                                                 927
Gly Val Cys Asn
305

<210> SEQ ID NO 2
<211> LENGTH: 308
<212> TYPE: PRT
<213> ORGANISM: Zea mays

<400> SEQUENCE: 2

Met Lys Leu Val Leu Val Val Leu Ala Phe Ile Ala Leu Val Ser Ser
1               5                   10                  15

Val Ser Cys Thr Gln Thr Gly Gly Cys Ser Cys Gly Gln Gln Gln Ser
            20                  25                  30

His Glu Gln Gln His His Pro Gln Gln His His Pro Gln Lys Gln Gln
        35                  40                  45

His Gln Pro Pro Gln His His Gln Gln Gln His Gln Gln Gln
    50                  55                  60

Gln Val His Met Gln Pro Gln Lys His Gln Gln Gln Gln Glu Val His
65                  70                  75                  80

Val Gln Gln Gln Gln Gln Pro Gln His Gln Gln Gln Gln Gln Gln
                85                  90                  95

Gln Gln His Gln Gln His Gln Cys Glu Gly Gln Gln Gln His His
            100                 105                 110

Gln Gln Ser Gln Gly His Val Gln His Glu Gln Ser His Glu Gln
            115                 120                 125

His Gln Gly Gln Ser His Glu Gln Gln His Gln Gln Gln Phe Gln Gly
    130                 135                 140

His Asp Lys Gln Gln Gln Pro Gln Gln Pro Gln Gln Tyr Gln Gln Gly
145                 150                 155                 160

Gln Glu Lys Ser Gln Gln Gln Cys His Cys Gln Glu Gln Gln Gln
                165                 170                 175

Thr Thr Arg Cys Ser Tyr Asn Tyr Ser Ser Ser Asn Leu Lys
            180                 185                 190

Asn Cys His Glu Phe Leu Arg Gln Gln Cys Ser Pro Leu Val Met Pro
        195                 200                 205

Phe Leu Gln Ser Arg Leu Ile Gln Pro Ser Ser Cys Gln Val Leu Gln
    210                 215                 220

Gln Gln Cys Cys His Asp Leu Arg Gln Ile Glu Pro Gln Tyr Ile His
225                 230                 235                 240

Gln Ala Ile Tyr Asn Met Val Gln Ser Ile Ile Gln Glu Glu Gln Gln
                245                 250                 255

Gln Gln Pro Cys Glu Leu Cys Gly Ser Gln Gln Ala Thr Gln Ser Ala
            260                 265                 270

Val Ala Ile Leu Thr Ala Ala Gln Tyr Leu Pro Ser Met Cys Gly Leu
        275                 280                 285

Tyr His Ser Tyr Tyr Gln Asn Asn Pro Cys Ser Ser Asn Asp Ile Ser
    290                 295                 300

Gly Val Cys Asn
305
```

```
<210> SEQ ID NO 3
<211> LENGTH: 585
<212> TYPE: DNA
<213> ORGANISM: Zea mays

<400> SEQUENCE: 3
atgaagctgg tgcttgtggt tcttgctttc attgctttag tatcaagtgt ttcttgtaca      60
cagacaggcg gctgcagctg tggtcaacaa caaagccatg agcagcaaca tcatccacaa     120
caacatcatc cacaaaaaca acaacatcaa ccaccaccac aacatcacca gcagcagcaa     180
caccaacaac aacaagttca catgcaacca caaaaacatc agcaacaaca agaagttcat     240
gttcaacaac aacaacaaca accgcagcac caacaacaac aacaacaaca acagcaccaa     300
caacaacatc aatgtgaagg ccaacaacaa catcaccaac aatcacaagg ccatgtgcaa     360
caacacgaac agagccatga gcaacaccaa ggacagagcc atgagcaaca catcaacaa      420
caattccagg gtcatgacaa gcagcaacaa ccacaacagc ctcagcaata tcagcagggc     480
caggaaaaat cacaacagca acaatgtcat tgccaggagc agcaacagac tacaaggtgc     540
agctataact actatagcag tagctcaaat ctaaaaaatt gtcat                     585

<210> SEQ ID NO 4
<211> LENGTH: 30
<212> TYPE: DNA
<213> ORGANISM: Zea mays

<400> SEQUENCE: 4
gaccacagct gcagccgcct gtctgtgtac                                       30

<210> SEQ ID NO 5
<211> LENGTH: 30
<212> TYPE: DNA
<213> ORGANISM: Zea mays

<400> SEQUENCE: 5
gcaatgaaag caagaaccac aagcaccagc                                       30

<210> SEQ ID NO 6
<211> LENGTH: 516
<212> TYPE: DNA
<213> ORGANISM: Zea mays

<400> SEQUENCE: 6
gggctggtaa attacttggg agcaatggta tgcaaatcct ttgcatgtac gcaaaactag      60
ctagttgtca caagttgtat atcgattcgt cgcgtttcaa caactcatgc aacattacaa     120
acaagtaaca caatattaca aagttagttt catacaaagc aagaaaagga caataatact     180
tgacatgtaa agtgaagctt attatacttc ctaatccaac acaaacaaa aaaaagttgc      240
acaaggtcc aaaatccac atcaaccatt aacctatacg taaagtgagt gatgagtcac       300
attatccaac aaatgtttat caatgtggta tcatacaagc attgacatcc cataaatgca     360
agaaattgtg ccaacaaagc tataagtaac cctcatatgt atttgcactc atgcatcaca     420
aaacatcctt ctatcagtac catcaatcat cattcatctt agtagtatag gcaccaaatc     480
aaatctgcaa catcaattat ctaactccaa aaaccc                               516

<210> SEQ ID NO 7
<211> LENGTH: 20
<212> TYPE: PRT
<213> ORGANISM: Zea mays
```

-continued

```
<220> FEATURE:
<221> NAME/KEY: MISC_FEATURE
<222> LOCATION: (7)..(9)
<223> OTHER INFORMATION: Xaa is any amino acid

<400> SEQUENCE: 7

Thr His Thr Ser Gly Gly Xaa Xaa Xaa Gln Pro Pro Pro Val His
1               5                   10                  15

Leu Leu Pro Pro
            20

<210> SEQ ID NO 8
<211> LENGTH: 20
<212> TYPE: PRT
<213> ORGANISM: Zea mays

<400> SEQUENCE: 8

Thr Gln Thr Gly Gly Cys Ser Cys Gly Gln Gln Gln Ser His Glu Gln
1               5                   10                  15

Gln His His Pro
            20

<210> SEQ ID NO 9
<211> LENGTH: 14
<212> TYPE: PRT
<213> ORGANISM: Artificial
<220> FEATURE:
<223> OTHER INFORMATION: Artifical epitope tag sequence V5

<400> SEQUENCE: 9

Gly Lys Pro Ile Pro Asn Pro Leu Leu Gly Leu Asp Ser Thr
1               5                   10

<210> SEQ ID NO 10
<211> LENGTH: 5
<212> TYPE: PRT
<213> ORGANISM: Artificial
<220> FEATURE:
<223> OTHER INFORMATION: Another artifical epitope tag sequence

<400> SEQUENCE: 10

Phe His His Thr Thr
1               5

<210> SEQ ID NO 11
<211> LENGTH: 6
<212> TYPE: PRT
<213> ORGANISM: Artificial
<220> FEATURE:
<223> OTHER INFORMATION: Artificially synthesized hexapeptide tag

<400> SEQUENCE: 11

Ser Glu Lys Asp Glu Leu
1               5

<210> SEQ ID NO 12
<211> LENGTH: 437
<212> TYPE: PRT
<213> ORGANISM: Artificial
<220> FEATURE:
<223> OTHER INFORMATION: gene product of the phytase expression cassette
      in vector 11037
```

-continued

<400> SEQUENCE: 12

```
Met Arg Val Leu Leu Val Ala Leu Ala Leu Leu Ala Leu Ala Ala Ser
1               5                   10                  15

Ala Thr Ser Ala Ala Gln Ser Glu Pro Glu Leu Lys Leu Glu Ser Val
            20                  25                  30

Val Ile Val Ser Arg His Gly Val Arg Ala Pro Thr Lys Ala Thr Gln
        35                  40                  45

Leu Met Gln Asp Val Thr Pro Asp Ala Trp Pro Thr Trp Pro Val Lys
    50                  55                  60

Leu Gly Glu Leu Thr Pro Arg Gly Gly Glu Leu Ile Ala Tyr Leu Gly
65                  70                  75                  80

His Tyr Trp Arg Gln Arg Leu Val Ala Asp Gly Leu Leu Pro Lys Cys
                85                  90                  95

Gly Cys Pro Gln Ser Gly Gln Val Ala Ile Ala Asp Val Asp Glu
            100                 105                 110

Arg Thr Arg Lys Thr Gly Glu Ala Phe Ala Ala Gly Leu Ala Pro Asp
            115                 120                 125

Cys Ala Ile Thr Val His Thr Gln Ala Asp Thr Ser Ser Pro Asp Pro
130                 135                 140

Leu Phe Asn Pro Leu Lys Thr Gly Val Cys Gln Leu Asp Asn Ala Asn
145                 150                 155                 160

Val Thr Asp Ala Ile Leu Glu Arg Ala Gly Gly Ser Ile Ala Asp Phe
            165                 170                 175

Thr Gly His Tyr Gln Thr Ala Phe Arg Glu Leu Glu Arg Val Leu Asn
            180                 185                 190

Phe Pro Gln Ser Asn Leu Cys Leu Lys Arg Glu Lys Gln Asp Glu Ser
            195                 200                 205

Cys Ser Leu Thr Gln Ala Leu Pro Ser Glu Leu Lys Val Ser Ala Asp
            210                 215                 220

Cys Val Ser Leu Thr Gly Ala Val Ser Leu Ala Ser Met Leu Thr Glu
225                 230                 235                 240

Ile Phe Leu Leu Gln Gln Ala Gln Gly Met Pro Glu Pro Gly Trp Gly
                245                 250                 255

Arg Ile Thr Asp Ser His Gln Trp Asn Thr Leu Leu Ser Leu His Asn
            260                 265                 270

Ala Gln Phe Asp Leu Leu Gln Arg Thr Pro Glu Val Ala Arg Ser Arg
            275                 280                 285

Ala Thr Pro Leu Leu Asp Leu Ile Lys Thr Ala Leu Thr Pro His Pro
            290                 295                 300

Pro Gln Lys Gln Ala Tyr Gly Val Thr Leu Pro Thr Ser Val Leu Phe
305                 310                 315                 320

Ile Ala Gly His Asp Thr Asn Leu Ala Asn Leu Gly Gly Ala Leu Glu
                325                 330                 335

Leu Asn Trp Thr Leu Pro Gly Gln Pro Asp Asn Thr Pro Pro Gly Gly
            340                 345                 350

Glu Leu Val Phe Glu Arg Trp Arg Arg Leu Ser Asp Asn Ser Gln Trp
            355                 360                 365

Ile Gln Val Ser Leu Val Phe Gln Thr Leu Gln Gln Met Arg Asp Lys
            370                 375                 380

Thr Pro Leu Ser Leu Asn Thr Pro Gly Glu Val Lys Leu Thr Leu
385                 390                 395                 400

Ala Gly Cys Glu Glu Arg Asn Ala Gln Gly Met Cys Ser Leu Ala Gly
                405                 410                 415
```

-continued

```
Phe Thr Gln Ile Val Asn Glu Ala Arg Ile Pro Ala Cys Ser Leu Ser
            420                 425                 430
Glu Lys Asp Glu Leu
        435

<210> SEQ ID NO 13
<211> LENGTH: 687
<212> TYPE: DNA
<213> ORGANISM: Zea mays
<220> FEATURE:
<221> NAME/KEY: misc_feature
<222> LOCATION: (1)..(6)
<223> OTHER INFORMATION: 5' Hind III recognition sequence
<220> FEATURE:
<221> NAME/KEY: misc_feature
<222> LOCATION: (682)..(687)
<223> OTHER INFORMATION: 3' BamH I recognition sequence

<400> SEQUENCE: 13
aagcttcgat catccaggtg caaccgtata agtcctaaag tggtgaggaa cacgaaacaa      60
ccatgcattg gcatgtaaag ctccaagaat ttgttgtatc cttaacaact cacagaacat     120
caaccaaaat tgcacgtcaa gggtattggg taagaaacaa tcaaacaaat cctctctgtg     180
tgcaaagaaa cacggtgagt catgccgaga tcatactcat ctgatataca tgcttacagc     240
tcacaagaca ttacaaacaa ctcatattgc attacaaaga tcgtttcatg aaaaataaaa     300
taggccggac aggacaaaaa tccttgacgt gtaaagtaaa tttacaacaa aaaaaaagcc     360
atatgtcaag ctaaatctaa ttcgttttac gtagatcaac aacctgtaga aggcaacaaa     420
actgagccac gcagaagtac agaatgattc cagatgaacc atcgacgtgc tacgtaaaga     480
gagtgacgag tcatatacat ttggcaagaa accatgaagc tgcctacagc cgtctcggtg     540
gcataagaac acaagaaatt gtgttaatta atcaaagcta taaataacgc tcgcatgcct     600
gtgcacttct ccatcaccac cactgggtct tcagaccatt agctttatct actccagagc     660
gcagaagaac ccgatcgaca aggatcc                                         687

<210> SEQ ID NO 14
<211> LENGTH: 11357
<212> TYPE: DNA
<213> ORGANISM: Artificial
<220> FEATURE:
<223> OTHER INFORMATION: Artificially constructed expression construct
      encoding a Nov9x phytase with a gamma zein signal sequence under
      the control of the gamma zein promoter
<220> FEATURE:
<221> NAME/KEY: misc_feature
<222> LOCATION: (1)..(11357)
<223> OTHER INFORMATION: The sequence presented is of a circular
      molecule

<400> SEQUENCE: 14
gaattggccg cagcggccat ttaaatcaat tgggcgcgcc gaattcgagc tcggtacaag      60
cttcgatcat ccaggtgcaa ccgtataagt cctaaagtgg tgaggaacac gaaacaacca     120
tgcattggca gtaaagctc caagaatttg ttgtatcctt aacaactcac agaacatcaa     180
ccaaaattgc acgtcaaggg tattgggtaa gaaacaatca aacaatcct ctctgtgtgc     240 aaagaaacac ggtgagtcat gccgagatca tactcatctg atatacatgc ttacagctca     300
caagacatta caaacaactc atattgcatt acaaagatcg tttcatgaaa aataaaatag     360
gccggacagg acaaaaatcc ttgacgtgta aagtaaattt acaacaaaaa aaagccata     420 tgtcaagcta aatctaattc gttttacgta gatcaacaac ctgtagaagg caacaaaact     480
```

-continued

```
gagccacgca gaagtacaga atgattccag atgaaccatc gacgtgctac gtaaagagag    540
tgacgagtca tatacatttg gcaagaaacc atgaagctgc ctacagccgt ctcggtggca    600
taagaacaca agaaattgtg ttaattaatc aaagctataa ataacgctcg catgcctgtg    660
cacttctcca tcaccaccac tgggtcttca gaccattagc tttatctact ccagagcgca    720
gaagaacccg atcgacagga tccaccatga gggtgttgct cgttgccctc gctctcctgg    780
ctctcgctgc gagcgccacc agcgctgcgc agtccgagcc ggagctgaag ctggagtccg    840
tggtgatcgt gtcccgccac ggcgtgcgcg ccccgaccaa ggccacccag ctcatgcagg    900
acgtgacccc ggacgcctgg ccgacctggc cggtgaagct cggcgagctg accccgcgcg    960
gcggcgagct gatcgcctac ctcggccact actggcgcca gcgcctcgtg ccgacggcc    1020 tcctcccgaa gtgcggctgc cgcagtccg gccaggtggc catcatcgcc gacgtggacg    1080
agcgcacccg caagaccggc gaggccttcg ccgccggcct cgccccggac tgcgccatca    1140
ccgtgcacac ccaggccgac acctcctccc cggacccgct cttcaacccg ctcaagaccg    1200
gcgtgtgcca gctcgacaac gccaacgtga ccgacgccat cctggagcgc gccggcggct    1260
ccatcgccga cttcaccggc cactaccaga ccgccttccg cgagctggag cgcgtgctca    1320
acttcccgca gtccaacctc tgcctcaagc gcgagaagca ggacgagtcc tgctccctca    1380
cccaggccct cccgtccgag ctgaaggtgt ccgccgactg cgtgtccctc accggcgccg    1440
tgtccctcgc ctccatgctc accgaaatct tcctcctcca gcaggcccag ggcatgccgg    1500
agccgggctg gggccgcatc accgactccc accagtggaa caccctcctc tccctccaca    1560
acgcccagtt cgacctcctc cagcgcaccc cggaggtggc ccgctcccgc gccacccgc    1620 tcctcgacct catcaagacc gccctcaccc cgcaccgcc gcagaagcag gcctacggcg    1680
tgaccctccc gacctccgtg ctcttcatcg ccggccacga caccaacctc gccaacctcg    1740
gcggcgccct ggagctgaac tggaccctcc cgggccagcc ggacaacacc ccgccgggcg    1800
gcgagctggt gttcgagcgc tggcgccgcc tctccgacaa ctcccagtgg attcaggtgt    1860
ccctcgtgtt ccagaccctc cagcagatgc gcgacaagac cccgctctcc ctcaacaccc    1920
cgccgggcga ggtgaagctc accctcgccg gctgcgagga gcgcaacgcc cagggcatgt    1980
gctccctcgc cggcttcacc cagatcgtga acgaggcccg catcccggcc tgctccctct    2040
ccgagaagga cgagctgtaa tagagctcta gatctgttct gcacaaagtg gagtagtcag    2100
tcatcgatca ggaaccagac accagacttt tattcataca gtgaagtgaa gtgaagtgca    2160
gtgcagtgag ttgctggttt ttgtacaact tagtatgtat ttgtatttgt aaaatacttc    2220
tatcaataaa atttctaatt cctaaaacca aaatccaggg gtaccagctt gcatgcctgc    2280
agtgcagcgt gacccggtcg tgcccctctc tagagataat gagcattgca tgtctaagtt    2340
ataaaaaatt accacatatt tttttgtca cacttgttg aagtgcagtt tatctatctt    2400
tatacatata tttaaacttt actctacgaa taatataatc tatagtacta caataatatc    2460
agtgttttag agaatcatat aaatgaacag ttagacatgg tctaaaggac aattgagtat    2520
tttgacaaca ggactctaca gttttatctt tttagtgtgc atgtgttctc ctttttttt    2580 gcaaatagct tcacctatat aatacttcat ccatttatt agtacatcca tttagggttt    2640
agggttaatg gtttttatag actaattttt ttagtacatc tatttattc tattttagcc    2700 tctaaattaa gaaaactaaa actctatttt agttttttta tttaataatt tagatataaa    2760
atagaataaa ataagtgac taaaattaa acaaataccc tttaagaaat taaaaaaact    2820
aaggaaacat ttttcttgtt tcgagtagat aatgccagcc tgttaaacgc cgtcgacgag    2880
```

```
tctaacggac accaaccagc gaaccagcag cgtcgcgtcg ggccaagcga agcagacggc    2940
acggcatctc tgtcgctgcc tctggacccc tctcgagagt tccgctccac cgttggactt    3000
gctccgctgt cggcatccag aaattgcgtg gcggagcggc agacgtgagc cggcacggca    3060
ggcggcctcc tcctcctctc acggcaccgg cagctacggg ggattccttt cccaccgctc    3120
cttcgctttc ccttcctcgc ccgccgtaat aaatagacac ccctccaca ccctctttcc     3180
ccaacctcgt gttgttcgga gcgcacacac acacaaccag atctccccca aatccacccg    3240
tcggcaccct cgcttcaagg tacgccgctc gtcctccccc ccccccctc tctaccttct     3300
ctagatcggc gttccggtcc atggttaggg cccggtagtt ctacttctgt tcatgtttgt    3360
gttagatccg tgtttgtgtt agatccgtgc tgctagcgtt cgtacacgga tgcgacctgt    3420
acgtcagaca cgttctgatt gctaacttgc cagtgtttct ctttgggaa tcctgggatg     3480
gctctagccg ttccgcagac gggatcgatt tcatgatttt ttttgtttcg ttgcataggg    3540
tttggttttgc ccttttcctt tatttcaata tatgccgtgc acttgtttgt cgggtcatct   3600
tttcatgctt tttttttgtct tggttgtgat gatgtggtct ggttgggcgg tcgttctaga  3660
tcggagtaga attctgtttc aaactacctg gtggatttat taattttgga tctgtatgtg   3720
tgtgccatac atattcatag ttacgaattg aagatgatgg atggaaatat cgatctagga   3780
taggtataca tgttgatgcg ggttttactg atgcatatac agagatgctt tttgttcgct   3840
tggttgtgat gatgtggtgt ggttgggcgg tcgttcattc gttctagatc ggagtagaat   3900
actgtttcaa actacctggt gtatttatta attttggaac tgtatgtgtg tgtcatacat   3960
cttcatagtt acgagtttaa gatggatgga aatatcgatc taggataggt atacatgttg   4020
atgtgggttt tactgatgca tatacatgat ggcatatgca gcatctattc atatgctcta   4080
accttgagta cctatctatt ataataaaca agtatgtttt ataattattt tgatcttgat   4140
atacttggat gatggcatat gcagcagcta tatgtggatt tttttagccc tgccttcata   4200
cgctatttat ttgcttggta ctgtttcttt tgtcgatgct caccctgttg tttggtgtta   4260
cttctgcagg gatccccgat catgcaaaaa ctcattaact cagtgcaaaa ctatgcctgg    4320
ggcagcaaaa cggcgttgac tgaactttat ggtatggaaa atccgtccag ccagccgatg   4380
gccgagctgt ggatgggcgc acatccgaaa agcagttcac gagtgcagaa tgccgccgga   4440
gatatcgttt cactgcgtga tgtgattgag agtgataaat cgactctgct cggagaggcc   4500
gttgccaaac gctttggcga actgcctttc ctgttcaaag tattatgcgc agcacagcca   4560
ctctccattc aggttcatcc aaacaaacac aattctgaaa tcggttttgc caaagaaaat   4620
gccgcaggta tcccgatgga tgccgccgag cgtaactata agatcctaa ccacaagccg    4680
gagctggttt ttgcgctgac gccttttcctt gcgatgaacg cgtttcgtga attttccgag  4740
attgtctccc tactccagcc ggtcgcaggt gcacatccgg cgattgctca cttttttacaa  4800
cagcctgatg ccgaacgttt aagcgaactg ttcgccagcc tgttgaatat gcagggtgaa   4860
gaaaaatccc gcgcgctggc gattttaaaa tcggccctcg atagccagca gggtgaaccg    4920
tggcaaacga ttcgtttaat ttctgaattt tacccggaag acagcggtct gttctccccg    4980
ctattgctga atgtggtgaa attgaaccct ggcgaagcga tgttcctgtt cgctgaaaca   5040
ccgcacgctt acctgcaagg cgtggcgctg gaagtgatgg caaactccga taacgtgctg   5100
cgtgcgggtc tgacgcctaa atacattgat attccggaac tggttgccaa tgtgaaattc   5160
gaagccaaac cggctaacca gttgttgacc cagccggtga acaaggtgc agaactggac    5220
ttcccgattc cagtggatga ttttgccttc tcgctgcatg accttagtga taaagaaacc   5280
```

```
accattagcc agcagagtgc cgccattttg ttctgcgtcg aaggcgatgc aacgttgtgg   5340
aaaggttctc agcagttaca gcttaaaccg ggtgaatcag cgtttattgc cgccaacgaa   5400
tcaccggtga ctgtcaaagg ccacggccgt tagcgcgtg tttacaacaa gctgtaagag    5460
cttactgaaa aaattaacat ctcttgctaa gctgggagct cgatccgtcg acctgcagat   5520
cgttcaaaca tttggcaata aagtttctta agattgaatc ctgttgccgg tcttgcgatg   5580
attatcatat aatttctgtt gaattacgtt aagcatgtaa taattaacat gtaatgcatg   5640
acgttattta tgagatgggt ttttatgatt agagtcccgc aattatacat ttaatacgcg   5700
atagaaaaca aaatatagcg cgcaaactag gataaattat cgcgcgcggt gtcatctatg   5760
ttactagatc tgctagccct gcaggaaatt taccggtgcc cgggcggcca gcatggccgt   5820
atccgcaatg tgttattaag ttgtctaagc gtcaatttgt ttacaccaca atatatcctg   5880
ccaccagcca gccaacagct ccccgaccgg cagctcggca caaaatcacc actcgataca   5940
ggcagcccat cagaattaat tctcatgttt gacagcttat catcgactgc acggtgcacc   6000
aatgcttctg gcgtcaggca gccatcggaa gctgtggtat ggctgtgcag gtcgtaaatc   6060
actgcataat tcgtgtcgct caaggcgcac tcccgttctg gataatgttt tttgcgccga   6120
catcataacg gttctggcaa atattctgaa atgagctgtt gacaattaat catccggctc   6180
gtataatgtg tggaattgtg agcggataac aatttcacac aggaaacaga ccatgaggga   6240
agcgttgatc gccgaagtat cgactcaact atcagaggta gttggcgtca tcgagcgcca   6300
tctcgaaccg acgttgctgg ccgtacattt gtacggctcc gcagtggatg gcggcctgaa   6360
gccacacagt gatattgatt tgctggttac ggtgaccgta aggcttgatg aaacaacgcg   6420
gcgagctttg atcaacgacc ttttggaaac ttcggcttcc cctggagaga gcgagattct   6480
ccgcgctgta gaagtcacca ttgttgtgca cgacgacatc attccgtggc gttatccagc   6540
taagcgcgaa ctgcaatttg gagaatggca gcgcaatgac attcttgcag gtatcttcga   6600
gccagccacg atcgacattg atctggctat cttgctgaca aaagcaagag aacatagcgt   6660
tgccttggta ggtccagcgg cggaggaact ctttgatccg gttcctgaac aggatctatt   6720
tgaggcgcta aatgaaacct taacgctatg gaactcgccg cccgactggg ctggcgatga   6780
gcgaaatgta gtgcttacgt tgtcccgcat ttggtacagc gcagtaaccg gcaaaatcgc   6840
gccgaaggat gtcgctgccg actgggcaat ggagcgcctg ccggcccagt atcagcccgt   6900
catacttgaa gctaggcagg cttatcttgg acaagaagat cgcttggcct cgcgcgcaga   6960
tcagttggaa gaatttgttc actacgtgaa aggcgagatc accaaagtag tcggcaaata   7020
aagctctagt ggatctccgt acccggggat ctggctcgcg cggacgcac gacgccgggg     7080 cgagaccata ggcgatctcc taaatcaata gtagctgtaa cctcgaagcg tttcacttgt   7140
aacaacgatt gagaatttt gtcataaaat tgaaatactt ggttcgcatt tttgtcatcc     7200
gcggtcagcc gcaattctga cgaactgccc atttagctgg agatgattgt acatccttca   7260
cgtgaaaatt tctcaagcgc tgtgaacaag ggttcagatt ttagattgaa aggtgagccg   7320
ttgaaacacg ttcttcttgt cgatgacgac gtcgctatgc ggcatcttat tattgaatac   7380
cttacgatcc acgccttcaa agtgaccgcg gtagccgaca gcacccagtt cacaagagta   7440
ctctcttccg cgacggtcga tgtcgtggtt gttgatctag atttaggtcg tgaagatggg   7500
ctcgagatcg ttcgtaatct ggcggcaaag tctgatattc caatcataat tatcagtggc   7560
gaccgccttg aggagacgga taaagttgtt gcactcgagc taggagcaag tgattttatc   7620
gctaagccgt tcagtatcag agagtttcta gcacgcattc gggttgcctt gcgcgtgcgc   7680
```

```
cccaacgttg tccgctccaa agaccgacgg tcttttttgtt ttactgactg gacacttaat    7740
ctcaggcaac gtcgcttgat gtccgaagct ggcggtgagg tgaaacttac ggcaggtgag    7800
ttcaatcttc tcctcgcgtt tttagagaaa ccccgcgacg ttctatcgcg cgagcaactt    7860
ctcattgcca gtcgagtacg cgacgaggag gtttatgaca ggagtataga tgttctcatt    7920
ttgaggctgc gccgcaaact tgaggcagat ccgtcaagcc ctcaactgat aaaaacagca    7980
agaggtgccg gttatttctt tgacgcggac gtgcaggttt cgcacggggg gacgatggca    8040
gcctgagcca attcccagat ccccgaggaa tcggcgtgag cggtcgcaaa ccatccggcc    8100
cggtacaaat cggcgcggcg ctgggtgatg acctggtgga gaagttgaag gccgcgcagg    8160
ccgcccagcg gcaacgcatc gaggcagaag cacgccccgg tgaatcgtgg caagcggccg    8220
ctgatcgaat ccgcaaagaa tcccggcaac cgccggcagc cggtgcgccg tcgattagga    8280
agccgcccaa gggcgacgag caaccagatt ttttcgttcc gatgctctat gacgtgggca    8340
cccgcgatag tcgcagcatc atggacgtgg ccgtttccg tctgtcgaag cgtgaccgac    8400
gagctggcga ggtgatccgc tacgagcttc agacgggca cgtagaggtt ccgcagggc    8460
cggccggcat ggccagtgtg tgggattacg acctggtact gatggcggtt tcccatctaa    8520
ccgaatccat gaaccgatac cgggaaggga agggagacaa gcccggccgc gtgttccgtc    8580
cacacgttgc ggacgtactc aagttctgcc ggcgagccga tggcggaaag cagaaagacg    8640
acctggtaga aacctgcatt cggttaaaca ccacgcacgt tgccatgcag cgtacgaaga    8700
aggccaagaa cggccgcctg gtgacggtat ccgagggtga agccttgatt agccgctaca    8760
agatcgtaaa gagcgaaacc gggcggccgg agtacatcga gatcgagcta gctgattgga    8820
tgtaccgcga gatcacagaa ggcaagaacc cggacgtgct gacggttcac cccgattact    8880
tttttgatcga tcccggcatc ggccgttttc tctaccgcct ggcacgccgc gccgcaggca    8940
aggcagaagc cagatggttg ttcaagacga tctacgaacg cagtggcagc gccggagagt    9000
tcaagaagtt ctgtttcacc gtgcgcaagc tgatcgggtc aaatgacctg ccggagtacg    9060
atttgaagga ggaggcgggg caggctggcc cgatcctagt catgcgctac cgcaaccctga    9120
tcgagggcga agcatccgcc ggttcctaat gtacggagca gatgctaggg caaattgccc    9180
tagcagggga aaaaggtcga aaaggtctct ttcctgtgga tagcacgtac attgggaacc    9240
caaagccgta cattgggaac cggaacccgt acattgggaa cccaaagccg tacattggga    9300
accggtcaca catgtaagtg actgatataa aagagaaaaa aggcgatttt tccgcctaaa    9360
actctttaaa acttattaaa actcttaaaa cccgcctggc ctgtgcataa ctgtctggcc    9420
agcgcacagc cgaagagctg caaaagcgc ctaccccttcg gtcgctgcgc tccctacgcc    9480
ccgccgcttc gcgtcggcct atcgcggccg ctggccgctc aaaaatggct ggcctacggc    9540
caggcaatct accagggcgc ggacaagccg cgccgtcgcc actcgaccgc cggcgctgag    9600
gtctgcctcg tgaagaaggt gttgctgact cataccaggc ctgaatcgcc ccatcatcca    9660
gccagaaagt gagggagcca cggttgatga gagctttgtt gtaggtggac cagttggtga    9720
ttttgaactt ttgctttgcc acggaacggt ctgcgttgtc gggaagatgc gtgatctgat    9780
ccttcaactc agcaaaagtt cgatttattc aacaaagccg ccgtcccgtc aagtcagcgt    9840
aatgctctgc cagtgttaca accaattaac caattctgat tagaaaaact catcgagcat    9900
caaatgaaac tgcaatttat tcatatcagg attatcaata ccatattttt gaaaaagccg    9960
tttctgtaat gaaggagaaa actcaccgag gcagttccat aggatggcaa gatcctggta   10020
tcggtctgcg attccgactc gtccaacatc aatacaacct attaatttcc cctcgtcaaa   10080
```

-continued

| | |
|---|---|
| aataaggtta tcaagtgaga aatcaccatg agtgacgact gaatccggtg agaatggcaa | 10140 |
| aagctctgca ttaatgaatc ggccaacgcg cggggagagg cggtttgcgt attgggcgct | 10200 |
| cttccgcttc ctcgctcact gactcgctgc gctcggtcgt tcggctgcgg cgagcggtat | 10260 |
| cagctcactc aaaggcggta atacggttat ccacagaatc aggggataac gcaggaaaga | 10320 |
| acatgtgagc aaaaggccag caaaaggcca ggaaccgtaa aaaggccgcg ttgctggcgt | 10380 |
| ttttccatag gctccgcccc cctgacgagc atcacaaaaa tcgacgctca agtcagaggt | 10440 |
| ggcgaaaccc gacaggacta taaagatacc aggcgtttcc ccctggaagc tccctcgtgc | 10500 |
| gctctcctgt tccgaccctg ccgcttaccg gatacctgtc cgcctttctc ccttcgggaa | 10560 |
| gcgtggcgct ttctcatagc tcacgctgta ggtatctcag ttcggtgtag gtcgttcgct | 10620 |
| ccaagctggg ctgtgtgcac gaaccccccg ttcagcccga ccgctgcgcc ttatccggta | 10680 |
| actatcgtct tgagtccaac ccggtaagac acgacttatc gccactggca gcagccactg | 10740 |
| gtaacaggat tagcagagcg aggtatgtag gcggtgctac agagttcttg aagtggtggc | 10800 |
| ctaactacgg ctacactaga agaacagtat ttggtatctg cgctctgctg aagccagtta | 10860 |
| ccttcggaaa aagagttggt agctcttgat ccggcaaaca aaccaccgct ggtagcggtg | 10920 |
| gtttttttgt ttgcaagcag cagattacgc gcagaaaaaa aggatctcaa gaagatcctt | 10980 |
| tgatcttttc tacggggtct gacgctcagt ggaacgaaaa ctcacgttaa gggattttgg | 11040 |
| tcatgagatt atcaaaaagg atcttcacct agatcctttt gatccggaat taattcctgt | 11100 |
| ggttggcatg cacatacaaa tggacgaacg gataaacctt ttcacgccct tttaaatatc | 11160 |
| cgattattct aataaacgct cttttctctt aggtttaccc gccaatatat cctgtcaaac | 11220 |
| actgatagtt taaactgaag gcgggaaacg acaatctgat catgagcgga gaattaaggg | 11280 |
| agtcacgtta tgacccccgc cgatgacgcg ggacaagccg ttttacgttt ggaactgaca | 11340 |
| gaaccgcaac gctgcag | 11357 |

<210> SEQ ID NO 15
<211> LENGTH: 9169
<212> TYPE: DNA
<213> ORGANISM: Artificial
<220> FEATURE:
<223> OTHER INFORMATION: Artificial Agrobacterium binary vector encoding
    E. coli manA phosphomannose isomerase under the transcriptional
    control of a maize ubiquitin promoter
<220> FEATURE:
<221> NAME/KEY: misc_feature
<222> LOCATION: (1)..(9169)
<223> OTHER INFORMATION: The sequence presented is of a circular
    molecule

<400> SEQUENCE: 15

| | |
|---|---|
| aagcttggcg cgccggtacc agcttgcatg cctgcagtgc agcgtgaccc ggtcgtgccc | 60 |
| ctctctagag ataatgagca ttgcatgtct aagttatata aaattaccac atatttttt | 120 |
| tgtcacactt gtttgaagtg cagtttatct atctttatac atatatttaa actttactct | 180 |
| acgaataata taatctatag tactacaata atatcagtgt tttagagaat catataaatg | 240 |
| aacagttaga catggtctaa aggacaattg agtatttga caacaggact ctacagtttt | 300 |
| atctttttag tgtgcatgtg ttctcctttt tttttgcaaa tagcttcacc tatataatac | 360 |
| ttcatccatt ttattagtac atccatttag ggtttagggt taatggtttt tatagactaa | 420 |
| ttttttagt acatctatt tattctattt tagcctctaa attaagaaaa ctaaaactct | 480 |
| attttagttt ttttatttaa taatttagat ataaaataga ataaaataaa gtgactaaaa | 540 |

| | |
|---|---|
| attaaacaaa tacccttaa gaaattaaaa aaactaagga aacatttttc ttgtttcgag | 600 |
| tagataatgc cagcctgtta aacgccgtcg acgagtctaa cggacaccaa ccagcgaacc | 660 |
| agcagcgtcg cgtcgggcca agcgaagcag acggcacggc atctctgtcg ctgcctctgg | 720 |
| accctctcg agagttccgc tccaccgttg gacttgctcc gctgtcggca tccagaaatt | 780 |
| gcgtggcgga gcggcagacg tgagccggca cggcaggcgg cctcctcctc ctctcacggc | 840 |
| accggcagct acgggggatt cctttcccac cgctccttcg cttccttc ctcgcccgcc | 900 |
| gtaataaata gacacccct ccacaccctc tttccccaac ctcgtgttgt tcggagcgca | 960 |
| cacacacaca accagatctc cccaaatcc acccgtcggc acctccgctt caaggtacgc | 1020 |
| cgctcgtcct cccccccccc ccctctctac cttctctaga tcggcgttcc ggtccatggt | 1080 |
| tagggcccgg tagttctact tctgttcatg tttgtgttag atccgtgttt gtgttagatc | 1140 |
| cgtgctgcta gcgttcgtac acggatgcga cctgtacgtc agacacgttc tgattgctaa | 1200 |
| cttgccagtg tttctctttg gggaatcctg ggatggctct agccgttccg cagacgggat | 1260 |
| cgatttcatg attttttttg tttcgttgca tagggtttgg tttgcccttt tcctttattt | 1320 |
| caatatatgc cgtgcacttg tttgtcgggt catcttttca tgcttttttt tgtcttggtt | 1380 |
| gtgatgatgt ggtctggttg ggcggtcgtt ctagatcgga gtagaattct gtttcaaact | 1440 |
| acctggtgga tttattaatt ttggatctgt atgtgtgtgc catacatatt catagttacg | 1500 |
| aattgaagat gatggatgga aatatcgatc taggataggt atacatgttg atgcgggttt | 1560 |
| tactgatgca tatacagaga tgcttttgt tcgcttggtt gtgatgatgt ggtgtggttg | 1620 |
| ggcggtcgtt cattcgttct agatcggagt agaatactgt ttcaaactac ctggtgtatt | 1680 |
| tattaattt ggaactgtat gtgtgtgtca tacatcttca tagttacgag tttaagatgg | 1740 |
| atggaaatat cgatctagga taggtataca tgttgatgtg ggttttactg atgcatatac | 1800 |
| atgatggcat atgcagcatc tattcatatg ctctaacctt gagtacctat ctattataat | 1860 |
| aaacaagtat gttttataat tattttgatc ttgatatact tggatgatgg catatgcagc | 1920 |
| agctatatgt ggatttttt agccctgcct tcatacgcta tttatttgct tggtactgtt | 1980 |
| tcttttgtcg atgctcaccc tgttgtttgg tgttacttct gcagggatcc ccgatcatgc | 2040 |
| aaaaactcat taactcagtg caaaactatg cctggggcag caaaacggcg ttgactgaac | 2100 |
| tttatggtat ggaaaatccg tccagccagc cgatggccga gctgtggatg ggcgcacatc | 2160 |
| cgaaaagcag ttcacgagtg cagaatgccg ccggagatat cgtttcactg cgtgatgtga | 2220 |
| ttgagagtga taaatcgact ctgctcggag aggccgttgc caaacgcttt ggcgaactgc | 2280 |
| ctttcctgtt caaagtatta tgcgcagcac agccactctc cattcaggtt catccaaaca | 2340 |
| aacacaattc tgaaatcggt tttgccaaag aaaatgccgc aggtatcccg atggatgccg | 2400 |
| ccgagcgtaa ctataaagat cctaaccaca agccggagct ggttttgcg ctgacgcctt | 2460 |
| tccttgcgat gaacgcgttt cgtgaatttt ccgagattgc tccctactc cagccggtcg | 2520 |
| caggtgcaca tccggcgatt gctcactttt acaacagcc tgatgccgaa cgtttaagcg | 2580 |
| aactgttcgc cagcctgttg aatatgcagg gtgaagaaaa atcccgcgcg ctggcgattt | 2640 |
| taaaatcggc cctcgatagc cagcagggtg aaccgtggca aacgattcgt ttaatttctg | 2700 |
| aattttaccc ggaagacagc ggtctgttct ccccgctatt gctgaatgtg gtgaaattga | 2760 |
| accctggcga agcgatgttc ctgttcgctg aaacaccgca cgcttacctg caaggcgtgg | 2820 |
| cgctggaagt gatggcaaac tccgataacg tgctgcgtgc gggtctgacg cctaaataca | 2880 |
| ttgatattcc ggaactggtt gccaatgtga aattcgaagc caaaccggct aaccagttgt | 2940 |

```
tgacccagcc ggtgaaacaa ggtgcagaac tggacttccc gattccagtg gatgattttg   3000
ccttctcgct gcatgacctt agtgataaag aaaccaccat tagccagcag agtgccgcca   3060
ttttgttctg cgtcgaaggc gatgcaacgt tgtggaaagg ttctcagcag ttacagctta   3120
aaccgggtga atcagcgttt attgccgcca acgaatcacc ggtgactgtc aaaggccacg   3180
gccgtttagc gcgtgtttac aacaagctgt aagagcttac tgaaaaaatt aacatctctt   3240
gctaagctgg gagctcgatc cgtcgacctg cagatcgttc aaacatttgg caataaagtt   3300
tcttaagatt gaatcctgtt gccggtcttg cgatgattat catataattt ctgttgaatt   3360
acgttaagca tgtaataatt aacatgtaat gcatgacgtt atttatgaga tgggttttta   3420
tgattagagt cccgcaatta tacatttaat acgcgataga aaacaaaata tagcgcgcaa   3480
actaggataa attatcgcgc gcggtgtcat ctatgttact agatctgcta gcccgcagg    3540 aaatttaccg gtgcccgggc ggccagcatg gccgtatccg caatgtgtta ttaagttgtc   3600
taagcgtcaa tttgtttaca ccacaatata tcctgccacc agccagccaa cagctccccg   3660
accggcagct cggcacaaaa tcaccactcg atacaggcag cccatcagaa ttaattctca   3720
tgtttgacag cttatcatcg actgcacggt gcaccaatgc ttctggcgtc aggcagccat   3780
cggaagctgt ggtatggctg tgcaggtcgt aaatcactgc ataattcgtg tcgctcaagg   3840
cgcactcccg ttctggataa tgttttttgc gccgacatca taacggttct ggcaaatatt   3900
ctgaaatgag ctgttgacaa ttaatcatcc ggctcgtata atgtgtggaa ttgtgagcgg   3960
ataacaattt cacacaggaa acagaccatg agggaagcgt tgatcgccga agtatcgact   4020
caactatcag aggtagttgg cgtcatcgag cgccatctcg aaccgacgtt gctggccgta   4080
catttgtacg gctccgcagt ggatggcggc ctgaagccac acagtgatat tgatttgctg   4140
gttacggtga ccgtaaggct tgatgaaaca acgcggcgag ctttgatcaa cgaccttttg   4200
gaaacttcgg cttcccctgg agagagcgag attctccgcg ctgtagaagt caccattgtt   4260
gtgcacgacg acatcattcc gtggcgttat ccagctaagc gcgaactgca atttggagaa   4320
tggcagcgca atgacattct tgcaggtatc ttcgagccag ccacgatcga cattgatctg   4380
gctatcttgc tgacaaaagc aagagaacat agcgttgcct tggtaggtcc agcggcggag   4440
gaactctttg atccggttcc tgaacaggat ctatttgagg cgctaaatga aaccttaacg   4500
ctatggaact cgccgcccga ctgggctggc gatgagcgaa atgtagtgct tacgttgtcc   4560
cgcatttggt acagcgcagt aaccggcaaa atcgcgccga aggatgtcgc tgccgactgg   4620
gcaatggagc gcctgccggc ccagtatcag cccgtcatac ttgaagctag gcaggcttat   4680
cttggacaag aagatcgctt ggcctcgcgc gcagatcagt tggaagaatt tgttcactac   4740
gtgaaaggcg agatcaccaa gtagtcggc aaataaagct ctagtggatc tccgtacccg   4800
gggatctggc tcgcggcgga cgcacgacgc cggggcgaga ccataggcga tctcctaaat   4860
caatagtagc tgtaacctcg aagcgtttca cttgtaacaa cgattgagaa ttttttgtcat   4920 aaaattgaaa tacttggttc gcatttttgt catccgcggt cagccgcaat tctgacgaac   4980
tgcccattta gctggagatg attgtacatc cttcacgtga aaatttctca agcgctgtga   5040
acaagggttc agattttaga ttgaaaggtg agccgttgaa acacgttctt cttgtcgatg   5100
acgacgtcgc tatgcggcat cttattattg aataccttac gatccacgcc ttcaaagtga   5160
ccgcggtagc cgacagcacc cagttcacaa gagtactctc ttccgcgacg gtcgatgtcg   5220
tggttgttga tctagattta ggtcgtgaag atgggctcga gatcgttcgt aatctggcgg   5280
caaagtctga tattccaatc ataattatca gtggcgaccg ccttgaggag acggataaag   5340
```

```
ttgttgcact cgagctagga gcaagtgatt ttatcgctaa gccgttcagt atcagagagt   5400
ttctagcacg cattcgggtt gccttgcgcg tgcgcccccaa cgttgtccgc tccaaagacc   5460
gacggtcttt ttgttttact gactggacac ttaatctcag gcaacgtcgc ttgatgtccg   5520
aagctggcgg tgaggtgaaa cttacggcag gtgagttcaa tcttctcctc gcgttttttag   5580 agaaaccccg cgacgttcta tcgcgcgagc aacttctcat tgccagtcga gtacgcgacg   5640
aggaggttta tgacaggagt atagatgttc tcattttgag gctgcgccgc aaacttgagg   5700
cagatccgtc aagccctcaa ctgataaaaa cagcaagagg tgccggttat ttctttgacg   5760
cggacgtgca ggtttcgcac gggggggacga tggcagcctg agccaattcc cagatccccg   5820
aggaatcggc gtgagcggtc gcaaaccatc cggcccggta caaatcggcg cggcgctggg   5880
tgatgacctg gtggagaagt tgaaggccgc gcaggccgcc cagcggcaac gcatcgaggc   5940
agaagcacgc cccggtgaat cgtggcaagc ggccgctgat cgaatccgca agaatcccg   6000 gcaaccgccg gcagccggtg cgccgtcgat taggaagccg cccaagggcg acgagcaacc   6060
agattttttc gttccgatgc tctatgacgt gggcacccgc gatagtcgca gcatcatgga   6120
cgtggccgtt ttccgtctgt cgaagcgtga ccgacgagct ggcgaggtga tccgctacga   6180
gcttccagac gggcacgtag aggtttccgc agggccggcc ggcatggcca gtgtgtggga   6240
ttacgacctg gtactgatgg cggtttccca tctaaccgaa tccatgaacc gataccggga   6300
agggaaggga gacaagcccg gccgcgtgtt ccgtccacac gttgcggacg tactcaagtt   6360
ctgccggcga gccgatggcg gaaagcagaa agacgacctg gtagaaacct gcattcggtt   6420
aaacaccacg cacgttgcca tgcagcgtac gaagaaggcc aagaacggcc gcctggtgac   6480
ggtatccgag ggtgaagcct tgattagccg ctacaagatc gtaaagagcg aaaccgggcg   6540
gccggagtac atcgagatcg agctagctga ttggatgtac cgcgagatca cagaaggcaa   6600
gaacccggac gtgctgacgg ttcaccccga ttacttttttg atcgatcccg gcatcggccg   6660 tttttctctac cgcctggcac gccgcgccgc aggcaaggca gaagccagat ggttgttcaa   6720
gacgatctac gaacgcagtg gcagcgccgg agagttcaag aagttctgtt tcaccgtgcg   6780
caagctgatc gggtcaaatg acctgccgga gtacgatttg aaggaggagg cggggcaggc   6840
tggcccgatc ctagtcatgc gctaccgcaa cctgatcgag ggcgaagcat ccgccggttc   6900
ctaatgtacg gagcagatgc tagggcaaat tgccctagca ggggaaaaag gtcgaaaagg   6960
tctctttcct gtggatagca cgtacattgg gaacccaaag ccgtacattg ggaaccggaa   7020
cccgtacatt gggaacccaa agccgtacat tgggaaccgg tcacacatgt aagtgactga   7080 tataaagag aaaaaaggcg attttttccgc ctaaaactct ttaaaactta ttaaaactct   7140 taaacccgc ctggcctgtg cataactgtc tggccagcgc acagccgaag agctgcaaaa   7200
agcgcctacc cttcggtcgc tgcgctccct acgccccgcc gcttcgcgtc ggcctatcgc   7260
ggccgctggc cgctcaaaaa tggctggcct acggccaggc aatctaccag ggcgcggaca   7320
agccgcgccg tcgccactcg accgccggcg ctgaggtctg cctcgtgaag aaggtgttgc   7380
tgactcatac caggcctgaa tcgccccatc atccagccag aaagtgaggg agccacggtt   7440
gatgagagct tgttgtagg tggaccagtt ggtgattttg aacttttgct ttgccacgga   7500
acggtctgcg ttgtcgggaa gatgcgtgat ctgatccttc aactcagcaa aagttcgatt   7560
tattcaacaa agccgccgtc ccgtcaagtc agcgtaatgc tctgccagtg ttacaaccaa   7620
ttaaccaatt ctgattagaa aaactcatcg agcatcaaat gaaactgcaa tttattcata   7680
tcaggattat caataccata tttttgaaaa agccgttttct gtaatgaagg agaaaactca   7740
```

| | |
|---|---|
| ccgaggcagt tccataggat ggcaagatcc tggtatcggt ctgcgattcc gactcgtcca | 7800 |
| acatcaatac aacctattaa tttcccctcg tcaaaaataa ggttatcaag tgagaaatca | 7860 |
| ccatgagtga cgactgaatc cggtgagaat ggcaaaagct ctgcattaat gaatcggcca | 7920 |
| acgcgcgggg agaggcggtt tgcgtattgg gcgctcttcc gcttcctcgc tcactgactc | 7980 |
| gctgcgctcg tcgttcggc tgcggcgagc ggtatcagct cactcaaagg cggtaatacg | 8040 |
| gttatccaca gaatcagggg ataacgcagg aaagaacatg tgagcaaaag gccagcaaaa | 8100 |
| ggccaggaac cgtaaaaagg ccgcgttgct ggcgtttttc cataggctcc gcccccctga | 8160 |
| cgagcatcac aaaaatcgac gctcaagtca gaggtggcga acccgacag gactataaag | 8220 |
| ataccaggcg tttcccctg gaagctccct cgtgcgctct cctgttccga ccctgccgct | 8280 |
| taccggatac ctgtccgcct ttctcccttc gggaagcgtg cgctttctc atagctcacg | 8340 |
| ctgtaggtat ctcagttcgg tgtaggtcgt tcgctccaag ctgggctgtg tgcacgaacc | 8400 |
| ccccgttcag cccgaccgct gcgccttatc cggtaactat cgtcttgagt ccaacccggt | 8460 |
| aagacacgac ttatcgccac tggcagcagc cactggtaac aggattagca gagcgaggta | 8520 |
| tgtaggcggt gctacagagt tcttgaagtg gtggcctaac tacggctaca ctagaagaac | 8580 |
| agtatttggt atctgcgctc tgctgaagcc agttaccttc ggaaaaagag ttggtagctc | 8640 |
| ttgatccggc aaacaaacca ccgctggtag cggtggtttt tttgtttgca agcagcagat | 8700 |
| tacgcgcaga aaaaaggat ctcaagaaga tcctttgatc ttttctacgg ggtctgacgc | 8760 |
| tcagtggaac gaaaactcac gttaagggat tttggtcatg agattatcaa aaaggatctt | 8820 |
| cacctagatc cttttgatcc ggaattaatt cctgtggttg gcatgcacat acaaatggac | 8880 |
| gaacggataa accttttcac gccctttaa atatccgatt attctaataa acgctctttt | 8940 |
| ctcttaggtt tacccgccaa tatatcctgt caaacactga tagtttaaac tgaaggcggg | 9000 |
| aaacgacaat ctgatcatga gcggagaatt aagggagtca cgttatgacc cccgccgatg | 9060 |
| acgcgggaca agccgtttta cgtttggaac tgacagaacc gcaacgctgc aggaattggc | 9120 |
| cgcagcggcc atttaaatca attgggcgcg ccgaattcga gctcggtac | 9169 |

<210> SEQ ID NO 16
<211> LENGTH: 5912
<212> TYPE: DNA
<213> ORGANISM: Artificial
<220> FEATURE:
<223> OTHER INFORMATION: Artificial intermediate plasmid encoding
      gamma-zein-galA fusion with 9 base linker
<220> FEATURE:
<221> NAME/KEY: misc_feature
<222> LOCATION: (1)..(5912)
<223> OTHER INFORMATION: The sequence presented is of a circular
      molecule

<400> SEQUENCE: 16

| | |
|---|---|
| caagatctgt tctgcacaaa gtggagtagt cagtcatcga tcaggaacca gacaccagac | 60 |
| ttttattcat acagtgaagt gaagtgaagt gcagtgcagt gagttgctgg ttttttgtaca | 120 |
| acttagtatg tatttgtatt tgtaaaatac ttctatcaat aaaatttcta attcctaaaa | 180 |
| ccaaaatcca gtgggtaccg aattcactgg ccgtcgtttt acaacgtcgt gactgggaaa | 240 |
| accctggcgt tacccaactt aatcgccttg cagcacatcc cctttcgcc agctggcgta | 300 |
| atagcgaaga ggcccgcacc gatcgccctt cccaacagtt gcgcagcctg aatggcgaat | 360 |
| ggcgcctgat gcggtatttt ctccttacgc atctgtgcgg tatttcacac cgcatatggt | 420 |
| gcactctcag tacaatctgc tctgatgccg catagttaag ccagccccga cacccgccaa | 480 |

```
cacccgctga cgcgccctga cgggcttgtc tgctcccggc atccgcttac agacaagctg    540
tgaccgtctc cgggagctgc atgtgtcaga ggttttcacc gtcatcaccg aaacgcgcga    600
gacgaaaggg cctcgtgata cgcctatttt tataggttaa tgtcatgata ataatggttt    660
cttagacgtc aggtggcact tttcggggaa atgtgcgcgg aacccctatt tgtttatttt    720
tctaaataca ttcaaatatg tatccgctca tgagacaata accctgataa atgcttcaat    780
ggcgcgccgc ggccgcttaa gaatattgaa aaggaagag tatgagtatt caacatttcc    840
gtgtcgccct tattccctttt tttgcggcat tttgccttcc tgttttttgct cacccagaaa    900 cgctggtgaa agtaaaagat gctgaagatc agttgggtgc acgagtgggt tacatcgaac    960
tggatctcaa cagcggtaag atccttgaga gttttcgccc cgaagaacgt tttccaatga   1020
tgagcacttt taaagttctg ctatgtggcg cggtattatc ccgtattgac gccgggcaag   1080
agcaactcgg tcgccgcata cactattctc agaatgactt ggttgagtac tcaccagtca   1140
cagaaaagca tcttacggat ggcatgacag taagagaatt atgcagtgct gccataacca   1200
tgagtgataa cactgcggcc aacttacttc tgacaacgat cggaggaccg aaggagctaa   1260 ccgcttttttt gcacaacatg ggggatcatg taactcgcct tgatcgttgg gaaccggagc   1320
tgaatgaagc cataccaaac gacgagcgtg acaccacgat gcctgtagca atggcaacaa   1380
cgttgcgcaa actattaact ggcgaactac ttactctagc ttcccggcaa caattaatag   1440
actggatgga ggcggataaa gttgcaggac cacttctgcg ctcggccctt ccggctggct   1500
ggtttattgc tgataaatct ggagccggtg agcgtgggtc tcgcggtatc attgcagcac   1560
tggggccaga tggtaagccc tcccgtatcg tagttatcta cacgacgggg agtcaggcaa   1620
ctatggatga acgaaataga cagatcgctg agataggtgc ctcactgatt aagcattggt   1680
aactgtcaga ccaagtttac tcatatatac tttagattga tttaaaactt cattttttaat   1740 ttaaaaggat ctaggtgaag atcctttttg ataatctcat gaccaaaatc ccttaacgtg   1800
agttttcgtt ccactgagcg tcagaccccg tagaaaagat caaaggatct tcttgagatc   1860 cttttttttct gcgcgtaatc tgctgcttgc aaacaaaaaa accaccgcta ccagcggtgg   1920
tttgtttgcc ggatcaagag ctaccaactc tttttccgaa ggtaactggc ttcagcagag   1980
cgcagatacc aaatactgtc cttctagtgt agccgtagtt aggccaccac ttcaagaact   2040
ctgtagcacc gcctacatac ctcgctctgc taatcctgtt accagtggct gctgccagtg   2100
gcgataagtc gtgtcttacc gggttggact caagacgata gttaccggat aaggcgcagc   2160
ggtcgggctg aacggggggt tcgtgcacac agcccagctt ggagcgaacg acctacaccg   2220
aactgagata cctacagcgt gagctatgag aaagcgccac gcttcccgaa gggagaaagg   2280
cggacaggta tccggtaagc ggcagggtcg aacaggaga gcgcacgagg gagcttccag   2340
ggggaaacgc ctggtatctt tatagtcctg tcgggtttcg ccacctctga cttgagcgtc   2400
gatttttgtg atgctcgtca ggggggcgga gcctatggaa aaacgccagc aacgcggcct   2460
ttttacggtt cctggccttt tgctggcctt tgctcacat gttctttcct gcgttatccc   2520
ctgattctgt ggataaccgt attaccgcct ttgagtgagc tgataccgct cgccgcagcc   2580
gaacgaccga gcgcagcgag tcagtgagcg aggaagcgga agagcttaag cggccgcggc   2640
gcgccgccca atacgcaaac cgcctctccc cgcgcgttgg ccgattcatt aatgcagctg   2700
gcacgacagg tttcccgact ggaaagcggg cagtgagcgc aacgcaatta atgtgagtta   2760
gctcactcat taggcacccc aggctttaca ctttatgctt ccggctcgta tgttgtgtgg   2820
aattgtgagc ggataacaat ttcacacagg aaacagctat gaccatgatt acgccaagct   2880
```

-continued

```
tcgatcatcc aggtgcaacc gtataagtcc taaagtggtg aggaacacga acaaccatg    2940 cattggcatg taaagctcca agaatttgtt gtatccttaa caactcacag aacatcaacc   3000
aaaattgcac gtcaagggta ttgggtaaga acaatcaaa caaatcctct ctgtgtgcaa    3060
agaaacacgg tgagtcatgc cgagatcata ctcatctgat atacatgctt acagctcaca   3120
agacattaca aacaactcat attgcattac aaagatcgtt tcatgaaaaa taaaataggc   3180
cggacaggac aaaaatcctt gacgtgtaaa gtaaatttac aacaaaaaaa aagccatatg   3240
tcaagctaaa tctaattcgt tttacgtaga tcaacaacct gtagaaggca acaaaactga   3300
gccacgcaga agtacagaat gattccagat gaaccatcga cgtgctacgt aaagagagtg   3360
acgagtcata tacatttggc aagaaaccat gaagctgcct acagccgtct cggtggcata   3420
agaacacaag aaattgtgtt aattaatcaa agctataaat aacgctcgca tgcctgtgca   3480
cttctccatc accaccactg ggtcttcaga ccattagctt tatctactcc agagcgcaga   3540
agaacccgat cgacaggatc caccatgagg gtgttgctcg ttgccctcgc tctcctggct   3600
ctcgctgcga gcgccacctc cacgcataca agcggcggct gcggctgcca gccaccgccg   3660
ccggttcatc taccgccgcc ggtgcatctg ccacctccgg ttcacctgcc acctccggtg   3720
catctcccac cgccggtcca cctgccgccg ccggtccacc tgccaccgcc ggtccatgtg   3780
ccgccgccgg ttcatctgcc gccgccacca tgccactacc ctactcaacc gccccggcct   3840
cagcctcatc cccagccaca cccatgcccg tgccaacagc cgcatccaag cccgtgccag   3900
ctgcagggaa cctgcggcgt tggcagcacc ccgatcctgg gccagtgcgt cgagttcctg   3960
aggcatcagt gcagcccgac ggcgacgccc tactgctcgc ctcagtgcca gtcgttgcgg   4020
cagcagtgtt gccagcagct caggcaggtg gagccgcagc accgctacca ggcgatcttc   4080
ggcttggtcc tccagtccat cctgcagcag cagccgcaaa gcggccaggt cgcggggctg   4140
ttggcggcgc agatagcgca gcaactgacg gcgatgtgcg gcctgcagca gccgactcca   4200 tgccctacg ccgctgccgg cggtgtcccc cacggcggcg ccatggagat tttcggcaag   4260
accttccgcg agggccgctt cgtgctcaag gagaagaact tcaccgtgga gttcgccgtg   4320
gagaagatcc acctcggctg gaagatatcg ggccgcgtga agggctcgcc gggccgcctc   4380
gaggtgctcc gcaccaaggc cccggagaag gtgctcgtga caactggca gtcctggggc    4440 ccgtgccgcg tggtggacgc cttctccttc aagccgccgg agatcgaccc gaactggcgc   4500
tacaccgcat ccgtggtgcc ggacgtgctc gagcgcaacc tgcagtccga ctacttcgtg   4560
gccgaggagg gcaaggtgta cggcttcctc tcctccaaga tcgcccaccc gttcttcgcg   4620
gtggaggacg gcgagctggt ggcctacctc gagtacttcg acgtggagtt cgacgacttc   4680
gtgccgctgg agccgctcgt ggtgctcgag gacccgaaca ccccgctcct cctcgagaag   4740
tacgccgagc tggtgggcat ggagaacaac gcccgggtgc cgaagcacac gccgaccggc   4800
tggtgctcct ggtatcacta cttcctcgac ctcacctggg aggagaccct caagaacctc   4860
aagctcgcca agaacttccc gttcgaggtg ttccagatcg acgacgccta cgagaaggac   4920
atcggcgact ggctcgtgac ccgcggcgac ttccgtccg tggaggagat ggccaaggtg   4980
atcgccgaga acggcttcat ccccggcatc tggaccgccc cgttctccgt gtccgagact   5040
agtgacgtgt tcaacgagca cccggactgg gtggtgaagg agaacggcga gccgaagatg   5100
gcctaccgca actggaacaa gaagatttac gccctcgacc tctccaagga cgaggtgctc   5160
aactggctct tcgacctctt ctcctccctc cgcaagatgg gctaccgcta cttcaagatc   5220
gacttcctct tcgcgggcgc cgtgccgggg gagcgcaaga agaacatcac cccgatccag   5280
```

```
gccttccgca aggcatcga gaccatccgc aaggccgtgg gggaggactc cttcatcctc    5340
ggctgcggct ccccctcct cccggccgtg ggctgcgtgg atggcatgcg catcggcccg    5400
gacaccgccc cgttctgggg agagcacatc gaggacaacg gcgccccggc ggcccgctgg    5460
gccctccgca acgccatcac ccgctacttc atgcacgacc gcttctggct caacgacccg    5520
gactgcctca tcctccgcga ggagaagacc gacctcaccc agaaggagaa ggagctgtac    5580
tcctacacct gcggcgttct agacaacatg atcatcgagt ccgacgacct ctccctcgtg    5640
cgcgaccacg gcaagaaggt gctcaaggag accctcgagc tgctcggggg caggccgcgc    5700
gtgcagaaca tcatgtccga ggacctccgc tacgagatcg tgtcctcggg caccctctcc    5760
ggcaacgtga gatcgtggt ggacctcaac tcccgcgagt accacctcga aggagggc      5820 aagtcctccc tcaagaagcg cgtggtgaag cgggaggacg gcaggaactt ctacttctac    5880
gaggagggcg agcgcgagtg agttaacgag ct                                  5912
```

<210> SEQ ID NO 17
<211> LENGTH: 11888
<212> TYPE: DNA
<213> ORGANISM: Artificial
<220> FEATURE:
<223> OTHER INFORMATION: Artificial Agrobacterium binary vector based on pNOV2117 into which a Q-protein coding sequence has been inserted
<220> FEATURE:
<221> NAME/KEY: misc_feature
<222> LOCATION: (1)..(11888)
<223> OTHER INFORMATION: The sequence presented is of a circular molecule

<400> SEQUENCE: 17

```
cgcgccggta ccagcttgca tgcctgcagt gcagcgtgac ccggtcgtgc ccctctctag      60
agataatgag cattgcatgt ctaagttata aaaaattacc acatattttt tttgtcacac     120
ttgtttgaag tgcagtttat ctatctttat acatatattt aaactttact ctacgaataa     180
tataatctat agtactacaa taatatcagt gttttagaga atcatataaa tgaacagtta     240
gacatggtct aaaggacaat tgagtatttt gacaacagga ctctacagtt ttatctttt     300 agtgtgcatg tgttctcctt tttttttgca aatagcttca cctatataat acttcatcca     360
ttttattagt acatccattt agggtttagg gttaatggtt tttatagact aattttttta     420
gtacatctat tttattctat tttagcctct aaattaagaa aactaaaact ctatttagt     480 ttttttattt aataatttag atataaaata gaataaaata aagtgactaa aaattaaaca     540 aataccettt aagaaattaa aaaaactaag gaaacatttt tcttgtttcg agtagataat     600
gccagcctgt taaacgccgt cgacgagtct aacggacacc aaccagcgaa ccagcagcgt     660
cgcgtcgggc caagcgaagc agacggcacg gcatctctgt cgctgcctct ggaccctct     720 cgagagttcc gctccaccgt tggacttgct ccgctgtcgg catccagaaa ttgcgtggcg     780
gagcggcaga cgtgagccgg cacggcaggc ggcctcctcc tcctctcacg gcaccggcag     840
ctacggggga ttccttccc accgctcctt cgctttccct tcctcgcccg ccgtaataaa     900
tagacacccc ctccacaccc tctttcccca acctcgtgtt gttcggagcg cacacacaca     960
caaccagatc tcccccaaat ccacccgtcg gcacctccgc ttcaaggtac gccgctcgtc    1020 ctccccccc ccccctctct accttctcta gatcggcgtt ccgtccatg gttagggccc      1080 ggtagttcta cttctgttca tgtttgtgtt agatccgtgt ttgtgttaga tccgtgctgc    1140
tagcgttcgt acacggatgc gacctgtacg tcagacacgt tctgattgct aacttgccag    1200 tgttttctctt tggggaatcc tgggatggct ctagccgttc cgcagacggg atcgatttca    1260
```

```
tgattttttt tgtttcgttg catagggttt ggtttgccct tttcctttat ttcaatatat   1320
gccgtgcact tgtttgtcgg gtcatctttt catgctttt ttttgtcttgg ttgtgatgat   1380 gtggtctggt tgggcggtcg ttctagatcg gagtagaatt ctgtttcaaa ctacctggtg   1440
gatttattaa ttttggatct gtatgtgtgt gccatacata ttcatagtta cgaattgaag   1500
atgatggatg gaaatatcga tctaggatag gtatacatgt tgatgcgggt tttactgatg   1560
catatacaga gatgctttt gttcgcttgg ttgtgatgat gtggtgtggt tgggcggtcg   1620
ttcattcgtt ctagatcgga gtagaatact gtttcaaact acctggtgta tttattaatt   1680
ttggaactgt atgtgtgtgt catacatctt catagttacg agtttaagat ggatggaaat   1740
atcgatctag gataggtata catgttgatg tgggttttac tgatgcatat acatgatggc   1800
atatgcagca tctattcata tgctctaacc ttgagtacct atctattata ataaacaagt   1860
atgttttata attattttga tcttgatata cttggatgat ggcatatgca gcagctatat   1920
gtggattttt ttagccctgc cttcatacgc tatttatttg cttggtactg tttcttttgt   1980
cgatgctcac cctgttgttt ggtgttactt ctgcagggat ccccgatcat gcaaaaactc   2040
attaactcag tgcaaaacta tgcctggggc agcaaaacgg cgttgactga actttatggt   2100
atggaaaatc cgtccagcca gccgatggcc gagctgtgga tgggcgcaca tccgaaaagc   2160
agttcacgag tgcagaatgc cgccggagat atcgtttcac tgcgtgatgt gattgagagt   2220
gataaatcga ctctgctcgg agaggccgtt gccaaacgct ttggcgaact gcctttcctg   2280
ttcaaagtat tatgcgcagc acagccactc tccattcagg ttcatccaaa caaacacaat   2340
tctgaaatcg gttttgccaa agaaaatgcc gcaggtatcc cgatggatgc cgccgagcgt   2400
aactataaag atcctaacca caagccggag ctggtttttg cgctgacgcc tttccttgcg   2460
atgaacgcgt ttcgtgaatt ttccgagatt gtctccctac tccagccggt cgcaggtgca   2520
catccggcga ttgctcactt tttacaacag cctgatgccg aacgtttaag cgaactgttc   2580
gccagcctgt tgaatatgca gggtgaagaa aaatcccgcg cgctggcgat tttaaaatcg   2640
gccctcgata gccagcaggg tgaaccgtgg caaacgattc gtttaatttc tgaattttac   2700
ccggaagaca gcggtctgtt ctccccgcta ttgctgaatg tggtgaaatt gaaccctggc   2760
gaagcgatgt tcctgttcgc tgaaacaccg cacgcttacc tgcaaggcgt ggcgctggaa   2820
gtgatggcaa actccgataa cgtgctgcgt gcgggtctga cgcctaaata cattgatatt   2880
ccggaactgg ttgccaatgt gaaattcgaa gccaaaccgg ctaaccagtt gttgacccag   2940
ccggtgaaac aaggtgcaga actggacttc ccgattccag tggatgattt tgccttctcg   3000
ctgcatgacc ttagtgataa agaaaccacc attagccagc agagtgccgc cattttgttc   3060
tgcgtcgaag gcgatgcaac gttgtggaaa ggttctcagc agttacagct taaaccgggt   3120
gaatcagcgt ttattgccgc caacgaatca ccggtgactg tcaaaggcca cggccgttta   3180
gcgcgtgttt acaacaagct gtaagagctt actgaaaaaa ttaacatctc ttgctaagct   3240
gggagctcga tccgtcgacc tgcagatcgt tcaaacattt ggcaataaag tttcttaaga   3300
ttgaatcctg ttgccggtct tgcgatgatt atcatataat ttctgttgaa ttacgttaag   3360
catgtaataa ttaacatgta atgcatgacg ttatttatga gatgggtttt tatgattaga   3420
gtcccgcaat tatacattta atacgcgata gaaaacaaaa tatagcgcgc aaactaggat   3480
aaattatcgc gcgcggtgtc atctatgtta ctagatctgc tagccctgca ggaaatttac   3540
cggtgcccgg gcgccagca tggccgtatc cgcaatgtgt tattaagttg tctaagcgtc   3600
aatttgttta caccacaata tatcctgcca ccagccagcc aacagctccc cgaccggcag   3660
```

```
ctcggcacaa aatcaccact cgatacaggc agcccatcag aattaattct catgtttgac    3720
agcttatcat cgactgcacg gtgcaccaat gcttctggcg tcaggcagcc atcggaagct    3780
gtggtatggc tgtgcaggtc gtaaatcact gcataattcg tgtcgctcaa ggcgcactcc    3840
cgttctggat aatgtttttt gcgccgacat cataacggtt ctggcaaata ttctgaaatg    3900
agctgttgac aattaatcat ccggctcgta taatgtgtgg aattgtgagc ggataacaat    3960
ttcacacagg aaacagacca tgagggaagc gttgatcgcc gaagtatcga ctcaactatc    4020
agaggtagtt ggcgtcatcg agcgccatct cgaaccgacg ttgctggccg tacatttgta    4080
cggctccgca gtggatggcg gcctgaagcc acacagtgat attgatttgc tggttacggt    4140
gaccgtaagg cttgatgaaa caacgcggcg agctttgatc aacgaccttt tggaaacttc    4200
ggcttcccct ggagagagcg agattctccg cgctgtagaa gtcaccattg ttgtgcacga    4260
cgacatcatt ccgtggcgtt atccagctaa gcgcgaactg caatttggag aatggcagcg    4320
caatgacatt cttgcaggta tcttcgagcc agccacgatc gacattgatc tggctatctt    4380
gctgacaaaa gcaagagaac atagcgttgc cttggtaggt ccagcggcgg aggaactctt    4440
tgatccggtt cctgaacagg atctatttga ggcgctaaat gaaaccttaa cgctatggaa    4500
ctcgccgccc gactgggctg gcgatgagcg aaatgtagtg cttacgttgt cccgcatttg    4560
gtacagcgca gtaaccggca aaatcgcgcc gaaggatgtc gctgccgact gggcaatgga    4620
gcgcctgccg gcccagtatc agcccgtcat acttgaagct aggcaggctt atcttggaca    4680
agaagatcgc ttggcctcgc gcgcagatca gttggaagaa tttgttcact acgtgaaagg    4740
cgagatcacc aaagtagtcg gcaaataaag ctctagtgga tctccgtacc cccggggat    4800 ctggctcgcg gcggacgcac gacgccgggg cgagaccata ggcgatctcc taaatcaata    4860
gtagctgtaa cctcgaagcg tttcacttgt aacaacgatt gagaattttt gtcataaaat    4920
tgaaatactt ggttcgcatt tttgtcatcc gcggtcagcc gcaattctga cgaactgccc    4980
atttagctgg agatgattgt acatccttca cgtgaaaatt tctcaagcgc tgtgaacaag    5040
ggttcagatt ttagattgaa aggtgagccg ttgaaacacg ttcttcttgt cgatgacgac    5100
gtcgctatgc ggcatcttat tattgaatac cttacgatcc acgccttcaa agtgaccgcg    5160
gtagccgaca gcacccagtt cacaagagta ctctcttccg cgacggtcga tgtcgtggtt    5220
gttgatctaa atttaggtcg tgaagatggg ctcgagatcg ttcgtaatct ggcggcaaag    5280
tctgatattc caatcataat tatcagtggc gaccgccttg aggagacgga taaagttgtt    5340
gcactcgagc taggagcaag tgattttatc gctaagccgt tcagtatcag agagtttcta    5400
gcacgcattc gggttgcctt gcgcgtgcgc cccaacgttg tccgctccaa agaccgacgg    5460 tcttttttgtt ttactgactg gacacttaat ctcaggcaac gtcgcttgat gtccgaagct    5520
ggcggtgagg tgaaacttac ggcaggtgag ttcaatcttc tcctcgcgtt tttagagaaa    5580
ccccgcgacg ttctatcgcg cgagcaactt ctcattgcca gtcgagtacg cgacgaggag    5640
gtttatgaca ggagtataga tgttctcatt ttgaggctgc gccgcaaact tgaggcagat    5700
ccgtcaagcc ctcaactgat aaaaacagca gaggtgccg gttatttctt tgacgcggac    5760
gtgcaggttt cgcacggggg gacgatggca gcctgagcca attcccagat ccccgaggaa    5820
tcggcgtgag cggtcgcaaa ccatccggcc cggtacaaat cggcgcggcg ctgggtgatg    5880
acctggtgga gaagttgaag gccgcgcagg ccgcccagcg gcaacgcatc gaggcagaag    5940
cacgccccgg tgaatcgtgg caagcggccg ctgatcgaat ccgcaaagaa tcccggcaac    6000
cgccggcagc cggtgcgccg tcgattagga agccgcccaa gggcgacgag caaccagatt    6060
```

```
ttttcgttcc gatgctctat gacgtgggca cccgcgatag tcgcagcatc atggacgtgg   6120
ccgttttccg tctgtcgaag cgtgaccgac gagctggcga ggtgatccgc tacgagcttc   6180
cagacgggca cgtagaggtt tccgcagggc cggccggcat ggccagtgtg tgggattacg   6240
acctggtact gatggcggtt tcccatctaa ccgaatccat gaaccgatac cgggaaggga   6300
agggagacaa gcccggccgc gtgttccgtc cacacgttgc ggacgtactc aagttctgcc   6360
ggcgagccga tggcggaaag cagaaagacg acctggtaga aacctgcatt cggttaaaca   6420
ccacgcacgt tgccatgcag cgtacgaaga aggccaagaa cggccgcctg gtgacggtat   6480
ccgagggtga agccttgatt agccgctaca agatcgtaaa gagcgaaacc gggcggccgg   6540
agtacatcga gatcgagcta gctgattgga tgtaccgcga gatcacagaa ggcaagaacc   6600
cggacgtgct gacggttcac cccgattact ttttgatcga tcccggcatc ggccgttttc   6660
tctaccgcct ggcacgccgc gccgcaggca aggcagaagc cagatggttg ttcaagacga   6720
tctacgaacg cagtggcagc gccggagagt tcaagaagtt ctgtttcacc gtgcgcaagc   6780
tgatcgggtc aaatgacctg ccggagtacg atttgaagga ggaggcgggg caggctggcc   6840
cgatcctagt catgcgctac cgcaacctga tcgagggcga agcatccgcc ggttcctaat   6900
gtacggagca gatgctaggg caaattgccc tagcagggga aaaggtcga aaggtctct     6960
ttcctgtgga tagcacgtac attgggaacc caaagccgta cattgggaac cggaacccgt   7020
acattgggaa cccaaagccg tacattggga accggtcaca catgtaagtg actgatataa   7080
aagagaaaaa aggcgatttt tccgcctaaa actctttaaa acttattaaa actcttaaaa   7140
cccgcctggc ctgtgcataa ctgtctggcc agcgcacagc cgaagagctg caaaaagcgc   7200
ctacccttcg gtcgctgcgc tcctacgcc ccgccgcttc gcgtcggcct atcgcggccg    7260
ctggccgctc aaaaatggct ggcctacggc caggcaatct accagggcgc ggacaagccg   7320
cgccgtcgcc actcgaccgc cggcgctgag gtctgcctcg tgaagaaggt gttgctgact   7380
cataccaggc ctgaatcgcc ccatcatcca gccagaaagt gagggagcca cggttgatga   7440
gagctttgtt gtaggtggac cagttggtga tttttgaactt tgctttgcc acggaacggt   7500
ctgcgttgtc gggaagatgc gtgatctgat ccttcaactc agcaaaagtt cgatttattc   7560
aacaaagccg ccgtcccgtc aagtcagcgt aatgctctgc cagtgttaca accaattaac   7620
caattctgat tagaaaaact catcgagcat caaatgaaac tgcaatttat tcatatcagg   7680
attatcaata ccatattttt gaaaagccg tttctgtaat gaaggagaaa actcaccgag    7740
gcagttccat aggatggcaa gatcctggta tcggtctgcg attccgactc gtccaacatc   7800
aatacaacct attaatttcc cctcgtcaaa ataaggttta tcaagtgaga aatcaccatg   7860
agtgacgact gaatccggtg agaatggcaa agctctgca ttaatgaatc ggccaacgcg    7920
cggggagagg cggtttgcgt attgggcgct cttccgcttc ctcgctcact gactcgctgc   7980
gctcggtcgt tcggctgcgg cgagcggtat cagctcactc aaaggcggta atacggttat   8040
ccacagaatc aggggataac gcaggaaaga acatgtgagc aaaaggccag caaaaggcca   8100
ggaaccgtaa aaaggccgcg ttgctggcgt ttttccatag ctccgcccc cctgacgagc    8160
atcacaaaaa tcgacgctca agtcagaggt ggcgaaaccc gacaggacta taaagatacc   8220
aggcgtttcc ccctggaagc tccctcgtgc gctctcctgt tccgaccctg ccgcttaccg   8280
gatacctgtc cgcctttctc ccttcgggaa gcgtggcgct ttctcatagc tcacgctgta   8340
ggtatctcag ttcggtgtag gtcgttcgct ccaagctggg ctgtgtgcac gaaccccccg   8400
ttcagcccga ccgctgcgcc ttatccggta actatcgtct tgagtccaac ccggtaagac   8460
```

```
acgacttatc gccactggca gcagccactg gtaacaggat tagcagagcg aggtatgtag    8520
gcggtgctac agagttcttg aagtggtggc ctaactacgg ctacactaga agaacagtat    8580
ttggtatctg cgctctgctg aagccagtta ccttcggaaa aagagttggt agctcttgat    8640
ccggcaaaca aaccaccgct ggtagcggtg gttttttttgt ttgcaagcag cagattacgc    8700
gcagaaaaaa aggatctcaa gaagatcctt tgatcttttc tacggggtct gacgctcagt    8760
ggaacgaaaa ctcacgttaa gggattttgg tcatgagatt atcaaaaagg atcttcacct    8820
agatcctttt gatccggaat taattcctgt ggttggcatg cacatacaaa tggacgaacg    8880
gataaaccct ttcacgccct tttaaatatc cgattattct aataaacgct cttttctctt    8940
aggtttaccc gccaatatat cctgtcaaac actgatagtt taaactgaag gcgggaaacg    9000
acaatctgat catgagcgga gaattaaggg agtcacgtta tgacccccgc cgatgacgcg    9060
ggacaagccg ttttacgttt ggaactgaca gaaccgcaac gctgcaggaa ttggccgcag    9120
cggccattta aatcaattgg gcgcgccgcc caatacgcaa accgcctctc cccgcgcgtt    9180
ggccgattca ttaatgcagc tggcacgaca ggtttcccga ctggaaagcg ggcagtgagc    9240
gcaacgcaat taatgtgagt tagctcactc attaggcacc ccaggcttta cactttatgc    9300
ttccggctcg tatgttgtgt ggaattgtga gcggataaca atttcacaca ggaaacagct    9360
atgaccatga ttacgccaag cttcgatcat ccaggtgcaa ccgtataagt cctaaagtgg    9420
tgaggaacac gaaacaacca tgcattggca tgtaaagctc aagaatttg ttgtatcctt    9480 aacaactcac agaacatcaa ccaaaattgc acgtcaaggg tattgggtaa gaaacaatca    9540
aacaaatcct ctctgtgtgc aaagaaacac ggtgagtcat gccgagatca tactcatctg    9600
atatacatgc ttacagctca caagacatta caaacaactc atattgcatt acaaagatcg    9660
tttcatgaaa aataaaatag gccggacagg acaaaaatcc ttgacgtgta aagtaaattt    9720
acaacaaaaa aaaagccata tgtcaagcta aatctaattc gttttacgta gatcaacaac    9780
ctgtagaagg caacaaaact gagccacgca gaagtacaga atgattccag atgaaccatc    9840
gacgtgctac gtaaagagag tgacgagtca tatacatttg gcaagaaacc atgaagctgc    9900
ctacagccgt ctcggtggca taagaacaca agaaattgtg ttaattaatc aaagctataa    9960
ataacgctcg catgcctgtg cacttctcca tcaccaccac tgggtcttca gaccattagc   10020
tttatctact ccagagcgca gaagaacccg atcgacagga tccaccatga agctggtgct   10080
tgtggttctt gctttcattg ctttagtatc aagtgtttct tgtacacaga caggcggctg   10140
cagctgtggt caacaacaaa gccatgagca gcaacatcat ccacaacaac atcatccaca   10200
aaaacaacaa catcaaccac caccacaaca tcaccagcag cagcaacacc aacaacaaca   10260
agttcacatg caaccacaaa acatcagca acaacaagaa gttcatgttc aacaacaaca   10320
acaacaaccg cagcaccaac aacaacaaca acaacaacag caccaacaac aacatcaatg   10380
tgaaggccaa caacaacatc accaacaatc acaaggccat gtgcaacaac acgaacagag   10440
ccatgagcaa caccaaggac agagccatga gcaacaacat caacaacaat tccagggtca   10500
tgacaagcag caacaaccac aacagcctca gcaatatcag cagggccagg aaaaatcaca   10560
acagcaacaa tgtcattgcc aggagcagca acagactaca aggtgcagct ataactacta   10620
tagcagtagc tcaaatctaa aaaattgtca tgaattccta aggcagcagt gcagcccttt   10680
ggtaatgcct tttctccaat cacgtttgat acaaccaagt agctgccagg tattgcagca   10740
acaatgttgt catgatctta ggcagattga gccacaatac attcaccaag caatctacaa   10800
catggttcaa tccataatcc aggaggagca acaacaacaa ccatgtgagt tatgtggatc   10860
```

```
tcaacaagct actcaaagtg cggtggcaat cttgacagca gcacaatacc taccatcaat    10920
gtgcggcttg taccactcat actaccaaaa taatccatgc agcagcaatg acattagtgg    10980
tgtttgcaat tgaagaattg tgtctaccta gccgttatac tcatataacg gtgttaagca    11040
ataaagtacc atacattatg atgttaaaaa aaaaaaaaa aaagcggccg ccaccgcggt     11100
ggagctcaag atctgttctg cacaaagtgg agtagtcagt catcgatcag gaaccagaca    11160
ccagactttt attcatacag tgaagtgaag tgaagtgcag tgcagtgagt tgctggtttt    11220
tgtacaactt agtatgtatt tgtatttgta aatacttct atcaataaaa tttctaattc     11280
ctaaaaccaa atccagtgg gtaccgaatt cactggccgt cgttttacaa cgtcgtgact     11340
gggaaaaccc tggcgttacc caacttaatc gccttgcagc acatcccct tcgccagct     11400 ggcgtaatag cgaagaggcc cgcaccgatc gcccttccca acagttgcgc agcctgaatg    11460
gcgaatggcg cctgatgcgg tattttctcc ttacgcatct gtgcggtatt tcacaccgca    11520
tatggtgcac tctcagtaca atctgctctg atgccgcata gttaagccag ccccgacacc    11580
cgccaacacc cgctgacgcg ccctgacggg cttgtctgct cccggcatcc gcttacagac    11640
aagctgtgac cgtctccggg agctgcatgt gtcagaggtt ttcaccgtca tcaccgaaac    11700
gcgcgagacg aaagggcctc gtgatacgcc tatttttata ggttaatgtc atgataataa    11760
tggtttctta gacgtcaggt ggcactttc ggggaaatgt gcgcggaacc cctatttgtt     11820
tatttttcta aatacattca aatatgtatc cgctcatgag acaataaccc tgataaatgc    11880
ttcaatgg                                                              11888

<210> SEQ ID NO 18
<211> LENGTH: 5290
<212> TYPE: DNA
<213> ORGANISM: Artificial
<220> FEATURE:
<223> OTHER INFORMATION: Artificial intermediate plasmid encoding gamma
      zein promoter-gamma zein signal sequence-galA fusion
<220> FEATURE:
<221> NAME/KEY: misc_feature
<222> LOCATION: (1)..(5290)
<223> OTHER INFORMATION: The sequence presented is of a circular
      molecule

<400> SEQUENCE: 18
ctagatctgt tctgcacaaa gtggagtagt cagtcatcga tcaggaacca gacaccagac      60
ttttattcat acagtgaagt gaagtgaagt gcagtgcagt gagttgctgg ttttttgtaca    120 acttagtatg tatttgtatt tgtaaaatac ttctatcaat aaaatttcta attcctaaaa    180
ccaaaatcca gggtaccga attcactggc cgtcgtttta acgtcgtg actgggaaaa       240 ccctggcgtt acccaactta atcgccttgc agcacatccc cctttcgcca gctggcgtaa    300
tagcgaagag gcccgcaccg atcgcccttc ccaacagttg cgcagcctga atggcgaatg    360
gcgcctgatg cggtattttc tccttacgca tctgtgcggt atttcacacc gcatatggtg    420
cactctcagt acaatctgct ctgatgccgc atagttaagc cagccccgac acccgccaac    480
acccgctgac gcgccctgac gggcttgtct gctcccggca tccgcttaca gacaagctgt    540
gaccgtctcc gggagctgca tgtgtcagag gttttcaccg tcatcaccga acgcgcgag     600 acgaaagggc tcgtgatac gcctattttt ataggttaat gtcatgataa taatggtttc    660
ttagacgtca ggtggcactt ttcggggaaa tgtgcgcgga acccctattt gtttattttt    720
ctaaatacat tcaaatatgt atccgctcat gagacaataa ccctgataaa tgcttcaatg    780
gcgcgccgcg gccgcttaag aatattgaaa aaggaagagt atgagtattc aacatttccg    840
```

-continued

```
tgtcgccctt attccctttt ttgcggcatt ttgccttcct gttttgctc acccagaaac      900 gctggtgaaa gtaaagatg ctgaagatca gttgggtgca cgagtgggtt acatcgaact      960
ggatctcaac agcggtaaga tccttgagag ttttcgcccc gaagaacgtt ttccaatgat    1020
gagcactttt aaagttctgc tatgtggcgc ggtattatcc cgtattgacg ccgggcaaga    1080
gcaactcggt cgccgcatac actattctca gaatgacttg gttgagtact caccagtcac    1140
agaaaagcat cttacggatg gcatgacagt aagagaatta tgcagtgctg ccataaccat    1200
gagtgataac actgcggcca acttacttct gacaacgatc ggaggaccga aggagctaac    1260
cgcttttttg cacaacatgg gggatcatgt aactcgcctt gatcgttggg aaccggagct    1320
gaatgaagcc ataccaaacg acgagcgtga caccacgatg cctgtagcaa tggcaacaac    1380
gttgcgcaaa ctattaactg gcgaactact tactctagct tcccggcaac aattaataga    1440
ctggatggag gcggataaag ttgcaggacc acttctgcgc tcggcccttc cggctggctg    1500
gtttattgct gataaatctg gagccggtga gcgtgggtct cgcggtatca ttgcagcact    1560
ggggccagat ggtaagccct cccgtatcgt agttatctac acgacgggga gtcaggcaac    1620 tatgatgaa cgaaatagac agatcgctga gataggtgcc tcactgatta gcattggta    1680 actgtcagac caagtttact catatatact ttagattgat ttaaaacttc attttaatt    1740 taaaaggatc taggtgaaga tcctttttga atctcatg accaaaatcc cttaacgtga    1800
gttttcgttc cactgagcgt cagaccccgt agaaagatc aaaggatctt cttgagatcc    1860 ttttttctg cgcgtaatct gctgcttgca acaaaaaaa ccaccgctac cagcggtggt    1920
ttgtttgccg gatcaagagc taccaactct ttttccgaag gtaactggct tcagcagagc    1980
gcagatacca aatactgtcc ttctagtgta gccgtagtta ggccaccact tcaagaactc    2040
tgtagcaccg cctacatacc tcgctctgct aatcctgtta ccagtggctg ctgccagtgg    2100
cgataagtcg tgtcttaccg ggttggactc aagacgatag ttaccggata aggcgcagcg    2160
gtcgggctga acggggggtt cgtgcacaca gcccagcttg gagcgaacga cctacaccga    2220
actgagatac ctacagcgtg agctatgaga aagcgccacg cttcccgaag ggagaaaggc    2280
ggacaggtat ccggtaagcg gcagggtcgg aacaggagag cgcacgaggg agcttccagg    2340
gggaaacgcc tggtatcttt atagtcctgt cgggtttcgc cacctctgac ttgagcgtcg    2400
atttttgtga tgctcgtcag ggggcggag cctatgaaa aacgccagca acgcggcctt    2460
tttacggttc ctggcctttt gctggccttt tgctcacatg ttctttcctg cgttatcccc    2520
tgattctgtg gataaccgta ttaccgcctt tgagtgagct gataccgctc gccgcagccg    2580
aacgaccgag cgcagcgagt cagtgagcga ggaagcggaa gagcttaagc ggccgcggcg    2640
cgccgcccaa tacgcaaacc gcctctcccc gcgcgttggc cgattcatta atgcagctgg    2700
cacgacaggt ttcccgactg gaaagcgggc agtgagcgca acgcaattaa tgtgagttag    2760
ctcactcatt aggcacccca ggctttacac tttatgcttc cggctcgtat gttgtgtgga    2820
attgtgagcg gataacaatt tcacacagga acagctatg accatgatta cgccaagctt    2880
cgatcatcca ggtgcaaccg tataagtcct aaagtggtga ggaacacgaa acaaccatgc    2940
attggcatgt aaagctccaa gaatttgttg tatccttaac aactcacaga acatcaacca    3000
aaattgcacg tcaagggtat tgggtaagaa acaatcaaac aaatcctctc tgtgtgcaaa    3060
gaaacacggt gagtcatgcc gagatcatac tcatctgata tacatgctta cagctcacaa    3120
gacattacaa caactcata ttgcattaca agatcgtttt catgaaaaat aaaataggcc    3180
ggacaggaca aaaatccttg acgtgtaaag taaatttaca acaaaaaaaa agccatatgt    3240
```

-continued

```
caagctaaat ctaattcgtt ttacgtagat caacaacctg tagaaggcaa caaaactgag    3300
ccacgcagaa gtacagaatg attccagatg aaccatcgac gtgctacgta aagagagtga    3360
cgagtcatat acatttggca agaaaccatg aagctgccta cagccgtctc ggtggcataa    3420
gaacacaaga aattgtgtta attaatcaaa gctataaata acgctcgcat gcctgtgcac    3480
ttctccatca ccaccactgg gtcttcagac cattagcttt atctactcca gagcgcagaa    3540
gaacccgatc gacaggatcc accatgaggg tgttgctcgt tgccctcgct ctcctggctc    3600
tcgctgcgag cgccacctcc atggagattt tcggcaagac cttccgcgag ggccgcttcg    3660
tgctcaagga gaagaacttc accgtggagt cgccgtgga agatccac ctcggctgga    3720
agatatcggg ccgcgtgaag ggctcgccgg gccgcctcga ggtgctccgc accaaggccc    3780
cggagaaggt gctcgtgaac aactggcagt cctggggccc gtgccgcgtg gtggacgcct    3840
tctccttcaa gccgccggag atcgacccga actggcgcta caccgcatcc gtggtgccgg    3900
acgtgctcga gcgcaacctg cagtccgact acttcgtggc cgaggagggc aaggtgtacg    3960
gcttcctctc ctccaagatc gcccacccgt tcttcgcggt ggaggacggc gagctggtgg    4020
cctacctcga gtacttcgac gtggagttcg acgacttcgt gccgctggag ccgctcgtgg    4080
tgctcgagga cccgaacacc ccgctcctcc tcgagaagta cgccgagctg gtgggcatgg    4140
agaacaacgc ccgggtgccg aagcacacgc cgaccggctg gtgctcctgg tatcactact    4200
tcctcgacct cacctgggag gagaccctca agaacctcaa gctcgccaag aacttcccgt    4260
tcgaggtgtt ccagatcgac gacgcctacg agaaggacat cggcgactgg ctcgtgaccc    4320
gcggcgactt cccgtccgtg gaggagatgg ccaaggtgat cgccgagaac ggcttcatcc    4380
ccggcatctg gaccgccccg ttctccgtgt ccgagactag tgacgtgttc aacgagcacc    4440
cggactgggt ggtgaaggag aacggcgagc cgaagatggc ctaccgcaac tggaacaaga    4500
agatttacgc cctcgacctc tccaaggacg aggtgctcaa ctggctcttc gacctcttct    4560
cctccctccg caagatgggc taccgctact tcaagatcga cttcctcttc gcgggcgccg    4620
tgccgggggga gcgcaagaag aacatcaccc cgatccaggc cttccgcaag ggcatcgaga    4680
ccatccgcaa ggccgtgggg gaggactcct tcatcctcgg ctgcggctcc cccctcctcc    4740
cggccgtggg ctgcgtggat ggcatgcgca tcggcccgga caccgccccg ttctggggag    4800
agcacatcga ggacaacggc gccccggcgg cccgctgggc cctccgcaac gccatcaccc    4860
gctacttcat gcacgaccgc ttctggctca acgacccgga ctgcctcatc ctccgcgagg    4920
agaagaccga cctcacccag aaggagaagg agctgtactc ctacacctgc ggcgttctag    4980
acaacatgat catcgagtcc gacgacctct ccctcgtgcg cgaccacggc aagaaggtgc    5040
tcaaggagac cctcgagctg ctcggggggca ggccgcgcgt gcagaacatc atgtccgagg    5100
acctccgcta cgagatcgtg tcctcgggca ccctctccgg caacgtgaag atcgtggtgg    5160
acctcaactc ccgcgagtac cacctcgaga aggagggcaa gtcctccctc aagaagcgcg    5220
tggtgaagcg ggaggacggc aggaacttct acttctacga ggagggcgag cgcgagtgag    5280
ttaacgagct                                                           5290
```

PROMOTER FROM MAIZE PROLAMIN SEED STORAGE PROTEIN AND USES THEREOF

CROSS REFERENCE TO RELATED APPLICATIONS

This application claims the benefit of U.S. Provisional Patent Application Ser. No. 60/551,286, filed Mar. 8, 2004, the disclosure of which is incorporated herein by reference in its entirety.

TECHNICAL FIELD

The presently disclosed subject matter relates generally to nucleic acids isolated from *Zea mays*. More particularly, the presently disclosed subject matter relates to nucleotide sequences encoding a member of the prolamin family of *Zea mays* cereal seed storage proteins, and to nucleotide sequences of a promoter of said prolamin family member. Also provided are methods of using the disclosed nucleic acid molecules in transgenic plants.

| Table of Abbreviations | |
|---|---|
| 2,4-D | 2,4-dichlorophenoxyacetic acid |
| AMV | alfalfa mosaic virus |
| β-ME | β-mercaptoethanol |
| BiP | human immunoglobulin heavy-chain binding polypeptide |
| bp | basepair(s) |
| CAB | chlorophyll a/b binding |
| CaMV | cauliflower mosaic virus |
| CDPK | maize calcium-dependent protein kinase |
| cM | centimorgan(s) |
| CMV | cytomegalovirus |
| DEAE | diethyl aminoethyl |
| DHFR | dihydrofolate reductase |
| DTT | dithiothreitol |
| EDTA | ethylene diamine tetraacetic acid |
| ELISA | enzyme-linked immunosorbent assay |
| EMCV | encephalomyocarditis virus |
| EPSP | 5-enol-pyruvyl shikimate-3-phosphate |
| ER | endoplasmic reticulum |
| EST | expressed sequence tag |
| GUS | β-glucuronidase |
| HEPES | N-(2-hydroxyethyl)piperazine-N'-(2-ethanesulfonic acid) |
| HSPs | high scoring sequence pairs |
| HSV-tk | Herpes Simplex Virus thymidine kinase |
| kb | kilobase(s) |
| $k_{cat}$ | catalytic constant |
| kDa | kilodalton(s) |
| $k_m$ | Michaelis constant |
| MCMV | maize chlorotic mottle virus |
| MDMV | maize dwarf mosaic virus |
| MTL | metallothionein-like |
| ORF | open reading frame |
| PAGE | polyacrylamide gel electrophoresis |
| PEG | polyethylene glycol |
| PEPC | phosphoenol carboxylase |
| pgk | phosphoglycerate kinase |
| Protox | protoporphyrinogen oxidase |
| psi | pounds per square inch |
| RFLPs | restriction fragment length polymorphisms |
| RUBISCO | ribulose-1,5-bisphosphate carboxylase/oxygenase |
| SDS | sodium dodecyl sulfate |
| SDS-PAGE | sodium dodecyl sulfate polyacrylamide gel electrophoresis |
| SSC | standard saline citrate |
| SSPE | standard saline-phosphate-EDTA |
| TEV | tobacco etch virus |
| $T_m$ | thermal melting point |

| Table of Abbreviations -continued | |
|---|---|
| TMTD | tetramethylthiuram disulfide |
| TMV | tobacco mosaic virus |

| Amino Acid Abbreviations, Codes, and Functionally Equivalent Codons | | | |
|---|---|---|---|
| Amino Acid | 3-Letter | 1-Letter | Codons |
| Alanine | Ala | A | GCA; GCC; GCG; GCU |
| Arginine | Arg | R | AGA; AGG; CGA; CGC; CGG; CGU |
| Asparagine | Asn | N | AAC; AAU |
| Aspartic; Acid | Asp | D | GAC; GAU |
| Cysteine | Cys | C | UGC; UGU |
| Glutamic; acid | Glu | E | GAA; GAG |
| Glutamine | Gln | Q | CAA; CAG |
| Glycine | Gly | G | GGA; GGC; GGG; GGU |
| Histidine | His | H | CAC; CAU |
| Isoleucine | Ile | I | AUA; AUC; AUU |
| Leucine | Leu | L | UUA; UUG; CUA; CUC; CUG; CUU |
| Lysine | Lys | K | AAA; AAG |
| Methionine; | Met | M | AUG |
| Phenylalanine | Phe | F | UUC; UUU |
| Proline | Pro | P | CCA; CCC; CCG; CCU |
| Serine | Ser | S | ACG; AGU; UCA; UCC; UCG; UCU |
| Threonine | Thr | T | ACA; ACC; ACG; ACU |
| Tryptophan | Trp | W | UGG |
| Tyrosine | Tyr | Y | UAC; UAU |
| Valine | Val | V | GUA; GUC; GUG; GUU |

BACKGROUND

An objective of crop trait functional genomics is to identify crop trait genes of interest, for example, genes capable of conferring useful agronomic traits in crop plants. Such agronomic traits include, but are not limited to, enhanced yield, whether in quantity or quality; enhanced nutrient acquisition and metabolic efficiency; enhanced or altered nutrient composition of plant tissues used for food, feed, fiber, or processing; enhanced utility for agricultural or industrial processing; enhanced resistance to plant diseases; enhanced tolerance of adverse environmental conditions including, but not limited to, drought, excessive cold, excessive heat, or excessive soil salinity or extreme acidity or alkalinity; and alterations in plant architecture or development, including changes in developmental timing. The deployment of such identified trait genes by either transgenic or non-transgenic approaches can materially improve crop plants for the benefit of agriculture.

Cereals are the most important crop plants on the planet in terms of both human and animal consumption. Genomic synteny (conservation of gene order within large chromosomal segments) is observed in rice, maize, wheat, barley, rye, oats, and other agriculturally important monocots including sorghum (see e.g., Kellogg, 1998; Song et al., 2001, and references therein), which facilitates the mapping and isolation of orthologous genes from diverse cereal species based on the sequence of a single cereal gene. Rice has the smallest (about 420 Mb) genome among the cereal grains, and has recently been a major focus of public and private genomic and EST sequencing efforts. See Goff et al., 2002.

The identification of genes that are important for crop development is an ongoing effort in the agricultural community. Additional information can also be derived from the analysis of the genomes of various important plants. For example, the identification of regulatory elements that control the expression of genes can also lead to the ability to manipulate the plant genome to express polypeptides of interest in specific tissues. In particular, certain plants are becoming the organisms of choice for large-scale production of commercially important proteins such as enzymes. This strategy takes advantage of the fact that during seed development, endosperm cells synthesize large amounts of storage proteins of the zein family, which are deposited in structures known as protein bodies derived from the endoplasmic reticulum. These protein bodies cofractionate with the gluten fraction produced in corn wet milling. The potential therefore exists to generate large quantities of recombinant enzymes in a form associated with gluten or in a more pure form following release of the recombinant enzyme activity from the gluten-associated or immobilized state.

What are needed, then, are new methods and reagents for expressing heterologous nucleotide sequences in plant cells. To meet these needs, the presently disclosed subject matter provides in some embodiments a promoter sequence for directing expression of heterologous nucleotide sequences in plant cells. Also provided are methods for expressing heterologous nucleotide sequences in plant cells using the disclosed promoter.

The presently disclosed subject matter addresses these problems associated with the expression of nucleotide sequences in transgenic plants, as well as other problems.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides methods for expressing a nucleotide sequence in a plant. In some embodiments, the method comprises (a) operably linking the nucleotide sequence to a promoter comprising SEQ ID NO: 6 to produce an expression cassette; and (b) generating a transgenic plant comprising the expression cassette, whereby the nucleotide sequence is expressed in the plant. In some embodiments, the generating comprises transforming a plant cell with the expression cassette and regenerating the plant from the transformed plant cell. In some embodiments, the generating comprises homologously recombining the nucleotide sequence into an endogenous genetic locus under the control of a promoter comprising SEQ ID NO: 6. In some embodiments, the transforming is by biolistic transformation of a vector comprising the expression cassette. In some embodiments, the vector is a binary *Agrobacterium* expression vector.

In some embodiments, the nucleotide sequence encodes a polypeptide selected from the group consisting of carbohydrases, cellulases, hemicellulases, pectinases, isomerases, lyases, proteases, heat shock proteins, chaperonins, phytases, insecticidal proteins, antimicrobial proteins, a-amylases, glucoamylases, glucanases, glucosidases, xylanases, ferulic acid esterases, galactosidases, pectinases, and chymosin.

The presently disclosed subject matter also provides methods for expressing a nucleotide sequence in a plant. In some embodiments, the method comprises (a) operably linking the nucleotide sequence to a plant promoter, the nucleotide sequence comprising SEQ ID NO: 1 to produce an expression cassette; and (b) generating a transgenic plant comprising the expression cassette, whereby the nucleotide sequence is expressed in the plant. In some embodiments, the generating comprises transforming a plant cell with the expression cassette and regenerating the plant from the transformed plant cell. In some embodiments, the transforming is by biolistic transformation of a vector comprising the expression cassette. In some embodiments, the vector is a binary *Agrobacterium* expression vector.

The presently disclosed subject matter also provides methods for producing a heterologous polypeptide in a plant cell. In some embodiments, the method comprises (a) generating a plant cell comprising a nucleotide sequence encoding the heterologous polypeptide operably linked to SEQ ID NO: 6; and (b) expressing in the plant cell the nucleotide sequence encoding the heterologous polypeptide, whereby the heterologous polypeptide is produced in the plant cell. In some embodiments, the generating comprises transforming the plant cell with an expression cassette comprising the nucleotide sequence encoding the heterologous polypeptide. In some embodiments, the generating comprises homologously recombining the nucleotide sequence into an endogenous genetic locus under the control of a promoter comprising SEQ ID NO: 6 such that the nucleotide sequence becomes operably linked to SEQ ID NO: 6. In some embodiments, the transforming is by biolistic transformation of a vector comprising the expression cassette. In some embodiments, the vector is a binary *Agrobacterium* expression vector. In some embodiments, the instant method further comprises regenerating a plant from the plant cell. In some embodiments, the instant method further comprises isolating the polypeptide from the plant. In some embodiments, the polypeptide is located within a protein body of endoplasmic reticulum of the plant cell.

The methods and compositions of the presently disclosed subject matter can be used to produce a heterologous polypeptide of interest in a plant cell. In some embodiments, the nucleotide sequence encodes a polypeptide selected from the group consisting of carbohydrases, cellulases, hemicellulases, pectinases, isomerases, lyases, proteases, heat shock proteins, chaperonins, phytases, insecticidal proteins, antimicrobial proteins, a-amylases, glucoamylases, glucanases, glucosidases, xylanases, ferulic acid esterases, galactosidases, pectinases, and chymosin.

The presently disclosed subject matter also provides methods for targeting a protein of interest to a structure of a plant cell selected from the group consisting of endoplasmic reticulum (ER) and apoplast. In some embodiments, the method comprises (a) fusing a nucleic acid molecule encoding a signal sequence of a *Zea mays* Q protein in frame to a nucleotide sequence encoding the protein of interest, wherein the nucleic acid molecule encoding a signal sequence of a *Zea mays* Q protein and the nucleotide sequence encoding the protein of interest are operably linked to a promoter to produce a plant expression construct; and (b) transforming the plant cell with the plant expression construct, whereby the protein of interest is targeted to the structure.

The presently disclosed subject matter also provides methods for producing a plant seed with an increased nutritional value. In some embodiments, the method comprises (a) transforming a plant cell with an expression vector comprising a nucleotide sequence encoding SEQ ID NO: 2, or a fragment or derivative thereof; (b) regenerating a plant from the transformed plant cell; and (c) isolating a seed from the regenerated plant, whereby a seed with an increased nutritional value is produced. In some embodiments, the increased nutritional value is selected from the group consisting of an increased level of an essential amino acid, an improved amino acid balance, and an improved amino acid digestibility, when compared to a seed from a non-transformed plant of the same species.

The presently disclosed subject matter also provides methods for targeting a protein of interest to a protein body in a plant. In some embodiments, the method comprises (a) fusing a nucleic acid molecule encoding SEQ ID NO: 2, or a fragment or derivative thereof, in frame to a nucleotide sequence encoding the protein of interest, wherein the nucleic acid molecule encoding SEQ ID NO: 2, or the fragment or derivative thereof, and the nucleotide sequence encoding the protein of interest are operably linked to a promoter to produce a plant expression construct; and (b) transforming the plant cell with the plant expression construct, whereby the protein of interest is targeted to a protein body in the plant.

The presently disclosed subject matter also provides isolated nucleic acid molecules, expression cassettes, recombinant vectors, cells, and transgenic plants comprising the disclosed nucleic acid molecules and expression cassettes. In some embodiments, the nucleic acid molecules and expression cassettes comprise SEQ ID NO: 1, and in some embodiments the nucleic acid molecules and expression cassettes comprise SEQ ID NO: 6. In some embodiments, the expression cassette is expressed in seed and a polypeptide encoded by the expression cassette is located within a protein body of endoplasmic reticulum of a cell of the seed.

The methods and compositions of the presently disclosed subject matter can be used with any plant species. In some embodiments, the plant is a monocot. In some embodiments, the monocot is selected from the group consisting of rice, maize, wheat, barley, oats, rye, millet, sorghum, triticale, secale, einkorn, spelt, emmer, teff, milo, flax, gramma grass, *Tripsacum*, and teosinte. In some embodiments, the plant is selected from the group consisting of rice, wheat, barley, rye, maize, potato, canola, soybean, sunflower, carrot, sweet potato, sugarbeet, bean, pea, chicory, lettuce, cabbage, cauliflower, broccoli, turnip, radish, spinach, asparagus, onion, garlic, eggplant, pepper, celery, squash, pumpkin, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane. In some embodiments, the plant is maize.

In some embodiments of the presently disclosed subject matter, the expression cassette is expressed in a tissue selected from the group consisting of the epidermis, root, vascular tissue, meristem, cambium, cortex, pith, leaf, flower, seed, and combinations thereof. In some embodiments, the expression cassette is expressed in a seed and a polypeptide encoded by the nucleotide sequence is located within a protein body of endoplasmic reticulum of a cell of the seed.

Accordingly, it is an object of the presently disclosed subject matter to provide reagents and methods for expressing heterologous sequences in plant cells. This and other objects are achieved in whole or in part by the presently disclosed subject matter.

An object of the presently disclosed subject matter having been stated hereinabove, and which are addressed in whole or in part by the presently disclosed subject matter, other objects will become evident as the description proceeds when taken in connection with the accompanying drawings as best described hereinbelow.

BRIEF DESCRIPTION OF THE SEQUENCE LISTING

Figure 1:
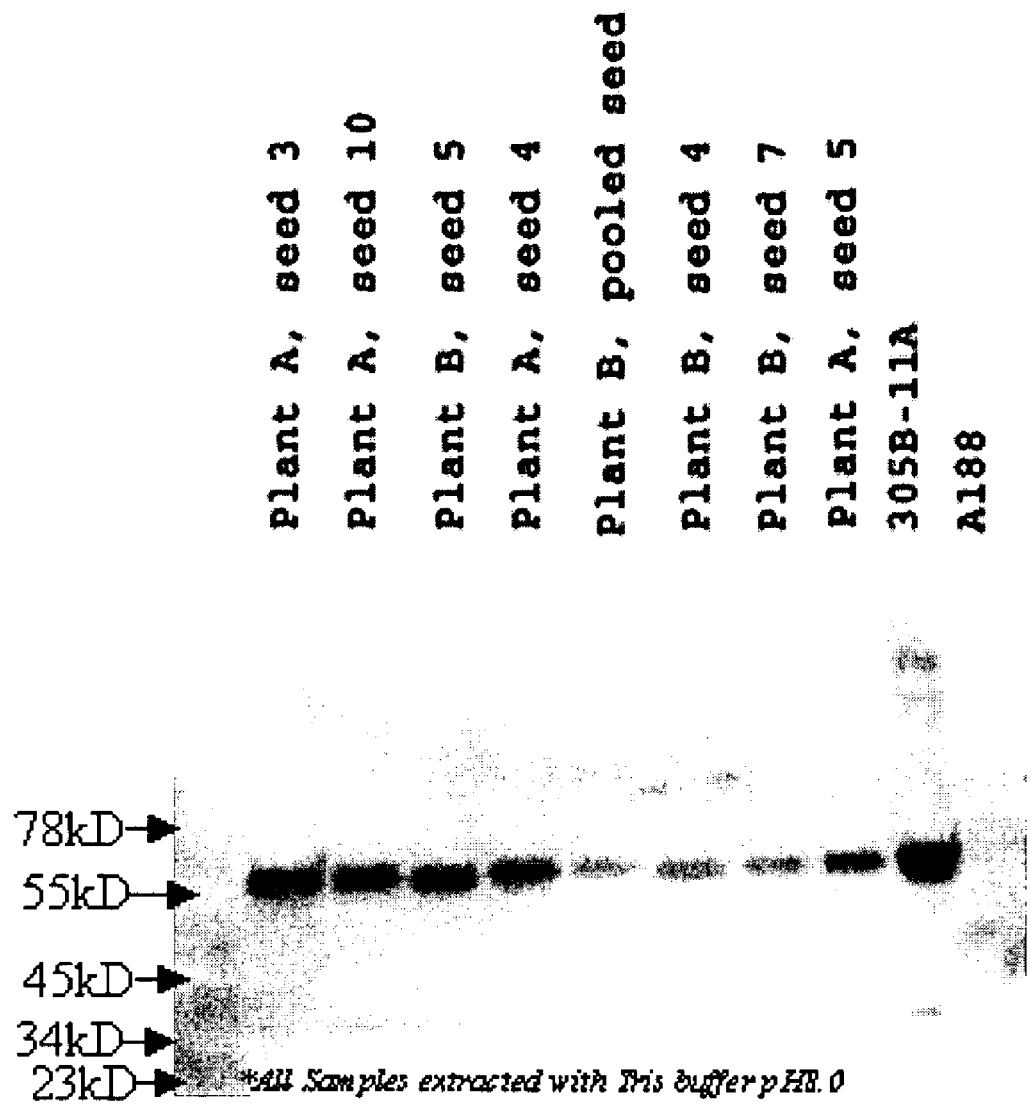
FIG. 1 depicts Western blot analysis of flour extracts using antisera to purified Nov9x phytase. The first lane on the blot depicts the positions of molecular weight standards (labeled on left). A188 is an extract of seed from non-transgenic corn. Nov9x phytase (predicted molecular weight 47 kDa) is identified as the prominent band migrating in the region of the 55 kDa standard. Nov9x phytase was not detected in the negative control (i.e. A188) corn flour extract.

SEQ ID NO: 1 is a nucleotide sequence of the open reading frame of the Q protein gene.

SEQ ID NO: 2 is an amino acid sequence encoded by SEQ ID NO: 1.

SEQ ID NO: 3 is a nucleotide sequence from the Q protein cDNA that was employed in genomic walking experiments to identify the promoter of the Q protein gene (SEQ ID NO: 6).

SEQ ID NOs: 4 and 5 are the nucleotide sequences of two Q-protein-specific primers that were employed in the genomic walking experiments.

SEQ ID NO: 6 is the nucleotide sequence of a promoter from the Q protein gene that is capable of directing expression of operably linked nucleotide sequences.

SEQ ID NO: 7 is a partial N-terminal amino acid sequence of an abundant 27 kDa protein isolated from maize endosperm, which matches the amino-terminus of the 28 kDa maize glutelin-2 (γ-zein; GENBANK® Accession No. P04706).

SEQ ID NO: 8 is a partial N-terminal amino acid sequence of the abundant 55 kDa protein isolated from maize endosperm.

SEQ ID NO: 9 is the amino acid sequence of the V5 epitope tag derived from the P and V proteins of the paramyxovirus of simian virus 5 (SV5).

SEQ ID NO: 10 is the amino acid sequence of a pentapeptide epitope tag.

SEQ ID NO: 11 is a C-terminal hexapeptide sequence present on recombinant Nov9x phytase.

SEQ ID NO: 12 is the amino acid sequence of the gene product of the phytase expression cassette.

SEQ ID NO: 13 is a nucleotide sequence of a *Zea mays* γ-zein promoter to which 5' Hind III and a 3' BamH I recognition sequences have been added.

SEQ ID NO: 14 is a nucleotide sequence of pNOV4061, an expression construct encoding a Nov9x phytase with a gamma zein signal sequence under the control of the gamma zein promoter.

SEQ ID NO: 15 is a nucleotide sequence of pNOV2117, an *Agrobacterium* binary vector encoding an *E. coli* manA phosphomannose isomerase polypeptide under the transcriptional control of a maize ubiquitin promoter.

SEQ ID NO: 16 is a nucleotide sequence of pNOV4325, an intermediate plasmid encoding a γ-zein-galA fusion protein separated by a 9 nucleotide linker.

SEQ ID NO: 17 is a nucleotide sequence of pNOV4349, an *Agrobacterium* binary vector based on pNOV2117 into which a Q-protein coding sequence has been inserted.

SEQ ID NO: 18 is a nucleotide sequence of pNOV4328, an intermediate plasmid encoding a γ-zein signal sequence/galA fusion protein under the transcriptional control of a γ-zein promoter.

DETAILED DESCRIPTION

The presently disclosed subject matter will be now be described more fully hereinafter with reference to the accompanying Examples, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

All publications, patent applications, patents, and other references cited herein are incorporated by reference in their entireties.

I. General Considerations

A 55 kDa maize protein (designated Q protein) was identified, and appears to belong to the prolamin family of cereal seed storage proteins. The protein is released from endosperm flour in the presence of dithiothreitol (DTT) and is the second most abundant protein in these extracts after γ-zein, which by itself constitutes about 15% of endosperm protein. An expressed sequence tag (EST) sequence encoding a portion of the protein was retrieved from the GEN-BANK® database. Using oligonucleotide primers derived from the EST sequence, two overlapping cDNA clones were amplified. The combined clones encode a polypeptide chain of 308 residues including a predicted signal peptide of 19 residues. The deduced sequence of the mature protein is 289 amino acids and includes 104 Gln and 13 Glu. The combined percentage of Gln and Glu residues is 40%, more than twice that reported for other zeins. The predicted sequence also includes 5 Lys, an amino acid that is completely lacking in all other zeins except 6-zein, which has just one. The γ-zein protein accumulates on the periphery of protein bodies, and the co-fractionation of the 55 kDa Q protein and γ-zein suggests that both proteins accumulate in this region.

Previous efforts aimed at increasing Lys content of zeins for improved nutrition involved the insertion of 1–2 Lys residues into α-zein (Wallace et al., 1988) and up to 10 Lys residues into γ-zein (Torrent et al., 1987). The modified zeins accumulated in structures resembling protein bodies when synthesized in transient expression systems using either *Xenopus* oocytes or maize endosperm. However, both α-zein and γ-zein lack Lys and contain only 1–4 acidic amino acids that might otherwise serve to neutralize positively charge residues. By contrast, the deduced sequence of the 55 kDa Q protein contains a total of 16 acidic residues. The presence of 5 Lys in the 55 kDa protein and its apparent localization at or near the surface of protein bodies suggests that its native conformation can tolerate substitution of additional Lys residues.

II. Definitions

Unless otherwise defined, all technical and scientific terms used herein have the same meaning as commonly understood by one of ordinary skill in the art to which the presently disclosed subject matter pertains. For clarity of the present specification, certain definitions are presented hereinbelow.

Following long-standing patent law convention, the terms "a", "an", and "the" refer to "one or more" when used in this application, including in the claims. Thus, the phrases "a cell" and "the cell" refer to one or more cells, unless the context is clearly to the contrary.

As used herein, the terms "associated with" and "operably linked" refer to two nucleotide sequences that are related physically or functionally. For example, a promoter or regulatory DNA sequence is said to be "associated with" a DNA sequence that encodes an RNA or a polypeptide if the two sequences are operably linked, or situated such that the regulator DNA sequence will affect the expression level of the coding or structural DNA sequence.

As used herein, the term "chimera" refers to a polypeptide that comprises domains or other features that are derived from different polypeptides or are in a position relative to each other that is not naturally occurring.

As used herein, the term "chimeric construct" refers to a recombinant nucleic acid molecule in which a promoter or regulatory nucleotide sequence is operably linked to, or associated with, a nucleotide sequence that codes for an mRNA or which is expressed as a polypeptide, such that the regulatory nucleotide sequence is able to regulate transcription or expression of the associated nucleotide sequence. The regulatory nucleotide sequence of the chimeric construct is not normally operably linked to the associated nucleotide sequence as found in nature.

As used herein, the terms "coding sequence" and "open reading frame" (ORF) are used interchangeably and refer to a nucleotide sequence that is transcribed into RNA such as mRNA, rRNA, tRNA, snRNA, sense RNA, or antisense RNA. In some embodiments, the RNA is then translated in vivo or in vitro to produce a polypeptide. In some embodiments, an ORF of a maize Q protein comprises SEQ ID NO: 1.

As used herein, the term "complementary" refers to two nucleotide sequences that comprise antiparallel nucleotide sequences capable of pairing with one another upon formation of hydrogen bonds between the complementary base residues in the antiparallel nucleotide sequences. As is known in the art, the nucleotide sequences of two complementary strands are the reverse complement of each other when each is viewed in the 5' to 3' direction.

As is also known in the art, two sequences that hybridize to each other under a given set of conditions do not necessarily have to be 100% fully complementary. As used herein, the terms "fully complementary" and "100% complementary" refer to sequences for which the complementary regions are 100% in Watson-Crick base-pairing: i.e., that no mismatches occur within the complementary regions. However, as is often the case with recombinant molecules (for example, cDNAs) that are cloned into cloning vectors, certain of these molecules can have non-complementary overhangs on either the 5' or 3' ends that result from the cloning event. In such a situation, it is understood that the region of 100% or full complementarity excludes any sequences that are added to the recombinant molecule (typically at the ends) solely as a result of, or to facilitate, the cloning event. Such sequences are, for example, polylinker sequences, linkers with restriction enzyme recognition sites, etc.

As used herein, the terms "domain" and "feature", when used in reference to a polypeptide or amino acid sequence, refers to a subsequence of an amino acid sequence that has a particular biological function. Domains and features that have a particular biological function include, but are not limited to, a signal sequence, a ligand binding domain, a nucleic acid binding domain, a catalytic domain, a substrate binding domain, and a polypeptide-polypeptide interacting domain. Similarly, when used herein in reference to a nucleotide sequence, a "domain", or "feature" is that subsequence of the nucleotide sequence that encodes a domain or feature of a polypeptide.

As used herein, the term "expression cassette" refers to a nucleic acid molecule capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually encodes a polypeptide of interest but can also encode a functional RNA of interest, for example antisense RNA or a non-translated RNA, in the sense or antisense direction. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression. Typically, however, at least one component of the expression cassette is heterologous with respect to the host; for example, a particular DNA sequence of the expression cassette does not occur naturally in the host cell and was introduced into the host cell or an ancestor of the host cell by a transformation event. The expression of the nucleotide sequence in the expression cassette can be under the control of a promoter (for example, the Q protein promoter of SEQ ID NO: 6), and in some embodiments, a promoter that initiates transcription only when the host cell is exposed to some particular external stimulus. In the case of a multicellular organism such as a plant, the promoter can also be specific to a particular tissue, organ, or stage of development (for example, a plant seed).

As used herein, the term "fragment" refers to a sequence that comprises a subset of another sequence. When used in the context of a nucleic acid or amino acid sequence, the terms "fragment" and "subsequence" are used interchangeably. A fragment of a nucleotide sequence can be any number of nucleotides that is less than that found in another nucleotide sequence, and thus includes, but is not limited to, the sequences of an exon or intron, a promoter, an enhancer, an origin of replication, a 5' or 3' untranslated region, a coding region, and a polypeptide binding domain. It is understood that a fragment or subsequence can also comprise less than the entirety of a nucleotide sequence, for example, a portion of an exon or intron, promoter, enhancer, etc. Similarly, a fragment or subsequence of an amino acid sequence can be any number of residues that is less than that found in a naturally occurring polypeptide, and thus includes, but is not limited to, domains, features, repeats, etc. Also similarly, it is understood that a fragment or subsequence of an amino acid sequence need not comprise the entirety of the amino acid sequence of the domain, feature, repeat, etc. A fragment can also be a "functional fragment", in which the fragment retains a specific biological function of the nucleotide sequence or amino acid sequence of interest. For example, a functional fragment of a transcription factor can include, but is not limited to, a DNA binding domain, a transactivating domain, or both. Similarly, a functional fragment of a receptor tyrosine kinase can include, but is not limited to, a ligand binding domain, a kinase domain, an ATP binding domain, and combinations thereof.

As used herein, the term "gene" is used broadly to refer to any segment of DNA associated with a biological function. Thus, genes include, but are not limited to, coding sequences and/or the regulatory sequences required for their expression. Genes can also include non-expressed DNA segments that, for example, form recognition sequences for a polypeptide. Genes can be obtained from a variety of sources, including cloning from a source of interest or synthesizing from known or predicted sequence information, and can include sequences designed to have desired parameters.

The terms "heterologous" and "recombinant", when used herein to refer to a nucleotide sequence (e.g. a DNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling or other recombinant techniques. The terms also include non-naturally occurring multiple copies of a naturally occurring DNA sequence. Thus, the terms refer to a DNA segment that is foreign to the host cell, or naturally occurring in the host cell but in a position or form within the host cell in which the element is not ordinarily found in nature. Similarly, when used in the context of a polypeptide or amino acid sequence, a heterologous polypeptide or amino acid sequence is a polypeptide or amino acid sequence that originates from a source foreign to the particular host cell (e.g., is generated from a heterologous coding sequence) or, if from the same source, is modified from its original form. Thus, heterologous DNA segments can be expressed to yield heterologous polypeptides.

A "homologous" nucleotide (or amino acid) sequence is a nucleotide (or amino acid) sequence naturally associated with a host cell into which it is introduced and that is present in the chromosomal or extrachromosomal position in which it is normally found in nature.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. The phrase "bind(s) substantially" refers to complementary hybridization between a probe nucleic acid and a target nucleic acid and embraces minor mismatches that can be accommodated by reducing the stringency of the hybridization media to achieve the desired detection of the target nucleotide sequence.

As used herein, the terms "mutation" and "mutant" carry their traditional connotations and refer to a change, inherited, naturally occurring, or introduced, in a nucleic acid or polypeptide sequence, and are used in their senses as generally known to those of skill in the art.

As used herein, the term "inhibitor" refers to a chemical substance that inactivates or decreases the biological activity of a polypeptide such as a biosynthetic and catalytic activity, receptor, signal transduction polypeptide, structural gene product, or transport polypeptide. The term "herbicide" (or "herbicidal compound") is used herein to define an inhibitor applied to a plant at any stage of development, whereby the herbicide inhibits the growth of the plant or kills the plant.

As used herein, the term "isolated", when used in the context of an isolated DNA molecule or an isolated polypeptide, is a DNA molecule or polypeptide that, by the hand of man, exists apart from its native environment and is therefore not a product of nature. An isolated DNA molecule or polypeptide can exist in a purified form or can exist in a non-native environment such as, for example, in a transgenic host cell.

As used herein, the term "mature polypeptide" refers to a polypeptide from which the transit peptide, signal peptide, and/or propeptide portions have been removed.

As used herein, the term "minimal promoter" refers to the smallest piece of a promoter, such as a TATA element, that can support any transcription. A minimal promoter typically has greatly reduced promoter activity in the absence of upstream or downstream activation. In the presence of a suitable transcription factor, a minimal promoter can function to permit transcription.

As used herein, the terms "cell", "cell line", and "cell culture" are used interchangeably, and all such designations include progeny. Thus, the words "transformants" and "transformed cells" include the primary subject cell and cultures derived therefrom without regard for the number of transfers and/or rounds of cell division that the originally manipulated cell or cells might have experienced. It is also understood that all progeny might not be precisely identical in DNA content, due to deliberate or inadvertent mutations. Mutant progeny that have the same function or biological activity as screened for in the originally transformed cell are encompassed by the terms. Where distinct designations are intended, it will be clear from the context.

As used herein, the term "native" refers to a gene that is naturally present in the genome of an untransformed plant cell. Similarly, when used in the context of a polypeptide, a "native polypeptide" is a polypeptide that is encoded by a native gene of an untransformed plant cell's genome.

As used herein, the term "naturally occurring" refers to an object that is found in nature as distinct from being artificially produced by man. For example, a polypeptide or nucleotide sequence that is present in an organism in its natural state, which has not been intentionally modified or isolated by man in the laboratory, is naturally occurring. As such, a polypeptide or nucleotide sequence is considered "non-naturally occurring" if it is encoded by or present within a recombinant molecule, even if the amino acid or nucleotide sequence is identical to an amino acid or nucleotide sequence found in nature.

As used herein, the term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleotide sequence also implicitly encompasses conservatively modified variants thereof (e.g. degenerate codon substitutions) and complementary sequences and as well as the sequence explicitly disclosed. Specifically, degenerate codon substitutions can be achieved by generating sequences in which the third position of one or more (or all) selected codons is substituted with mixed-base and/or deoxyinosine residues (Batzer et al., 1991; Ohtsuka et al., 1985; Rossolini et al., 1994). The terms "nucleic acid" or "nucleotide sequence" can also be used interchangeably with gene, cDNA, and mRNA encoded by a gene.

As used herein, the term "orthologs" refers to genes in different species that encode protein that perform the same biological function. For example, the glucose-6-phosphate dehydrogenase genes from, for example, sorghum and rice, are orthologs. Typically, orthologous nucleotide sequences are characterized by a high degree of sequence similarity (for example, at least about 90% sequence identity). A nucleotide sequence of an ortholog in one species (for example, rice) can be used to isolate the nucleotide sequence of the ortholog in another species (for example, sorghum) using standard molecular biology techniques. This can be accomplished, for example, using techniques described in more detail below (see also Sambrook & Russell, 2001 for a discussion of hybridization conditions that can be used to isolate closely related sequences).

As used herein, the phrase "percent identical", in the context of two nucleic acid or polypeptide sequences, refers to two or more sequences or subsequences that have in some embodiments 60% (e.g., 60, 63, 65, 67, or 69%), in some embodiments 70% (e.g., 70, 73, 75, 77, or 79%), in some embodiments 80% (e.g., 80, 83, 85, 87, or 89%), in some embodiments 90% (e.g., 90, 93, 95, or 97), and in some embodiments at least 99% nucleotide or amino acid residue identity, respectively, when compared and aligned for maximum correspondence, as measured using one of the following sequence comparison algorithms or by visual inspection. The percent identity exists in some embodiments over a region of the sequences that is at least about 50 residues in length, in some embodiments over a region of at least about 100 residues, and In some embodiments, the percent identity exists over at least about 150 residues. In some embodiments, the percent identity exists over the entire length of the sequences.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm disclosed in Smith & Waterman, 1981, by the homology alignment algorithm disclosed in Needleman & Wunsch, 1970, by the search for similarity method disclosed in Pearson & Lipman, 1988, by computerized implementations of these algorithms (GAP, BESTFIT, FASTA, and TFASTA in the GCG® WISCONSIN PACKAGE®, available from Accelrys, Inc., San Diego, Calif., United States of America), or by visual inspection. See generally, Ausubel et al., 2002; Ausubel et al., 2003.

One example of an algorithm that is suitable for determining percent sequence identity and sequence similarity is the BLAST algorithm, which is described in Altschul et al., 1990. Software for performing BLAST analysis is publicly available through the website of the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. See generally, Altschul et al., 1990. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, orthe end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N==4, and a comparison of both strands. For amino acid sequences, the BLASTP program uses as defaults a wordlength (W) of 3, an expectation (E) of 10, and the BLOSUM62 scoring matrix. See Henikoff & Henikoff, 1992.

In addition to calculating percent sequence identity, the BLAST algorithm also performs a statistical analysis of the similarity between two sequences (see e.g., Karlin & Altschul, 1993). One measure of similarity provided by the BLAST algorithm is the smallest sum probability (P(N)), which provides an indication of the probability by which a match between two nucleotide or amino acid sequences would occur by chance. For example, a test nucleotide sequence is considered similar to a reference sequence if the smallest sum probability in a comparison of the test nucleotide sequence to the reference nucleotide sequence is in some embodiments less than about 0.1, in some embodiments less than about 0.01, and in some embodiments less than about 0.001.

As used herein, the terms "Q protein", "55 kDa protein", "55 kDa Q protein", and "55 kDa maize protein" are used interchangeably and refer to a polypeptide comprising the amino acid sequence of SEQ ID NO: 2, and variants, fragments, and domains thereof. A representative open reading frame for this polypeptide sequence has been identified, and has the nucleotide sequence provided in SEQ ID NO: 1. Additionally, a region of the maize promoter that controls transcription of this coding sequence in maize, referred to alternatively herein as the "Q protein gene promoter", the "promoter from the Q protein gene", etc., has been identified, and comprises the nucleotide sequence presented in SEQ ID NO: 6.

As used herein, the term "shuffled nucleic acid" refers to a recombinant nucleic acid molecule in which the nucleotide sequence comprises a plurality of nucleotide sequence fragments, wherein at least one of the fragments corresponds to a region of a nucleotide sequence listed in SEQ ID NO: 1, and wherein at least two of the plurality of sequence fragments are in an order, from 5' to 3', which is not an order in which the plurality of fragments naturally occur in a nucleic acid.

The term "substantially identical", in the context of two nucleotide or amino acid sequences, refers to two or more sequences or subsequences that have in some embodiments at least about 60% nucleotide or amino acid identity (e.g., 60, 63, 65, 67, or 69% nucleotide or amino acid identity), in some embodiments at least about 70% nucleotide or amino acid identity (e.g., 70, 73, 75, 78, or 79% nucleotide or amino acid identity), in some embodiments at least about 80% nucleotide or amino acid identity (e.g., 80, 83, 85, 88, or 89% nucleotide or amino acid identity), and in some embodiments at least about 90% nucleotide or amino acid identity (e.g., 90, 93, 95, 98, or 99% nucleotide or amino acid identity), when compared and aligned for maximum correspondence, as measured using one of the above-referenced sequence comparison algorithms or by visual inspection. In some embodiments, the substantial identity exists in nucleotide or amino acid sequences of at least 50 residues, in some embodiments in nucleotide or amino acid sequence of at least about 100 residues, in some embodiments in nucleotide or amino acid sequences of at least about 150 residues, and in some embodiments in nucleotide or amino acid sequences comprising complete coding sequences or complete amino acid sequences.

In one aspect, polymorphic sequences can be substantially identical sequences. The term "polymorphic" refers to the two or more genetically determined alternative sequences or alleles in a population. An allelic difference can be as small as one base pair. Nonetheless, one of ordinary skill in the art would recognize that the polymorphic sequences correspond to the same gene.

Another indication that two nucleotide sequences are substantially identical is that the two molecules specifically or substantially hybridize to each other under conditions of medium or high stringency. In the context of nucleic acid hybridization, two nucleotide sequences being compared can be designated a "probe sequence" and a "target sequence". A "probe sequence" is a reference nucleic acid molecule, and a "target sequence" is a test nucleic acid molecule, often found within a heterogeneous population of nucleic acid molecules. A "target sequence" is synonymous with a "test sequence".

An exemplary nucleotide sequence employed for hybridization studies or assays includes probe sequences that are complementary to or mimic in some embodiments at least an about 14 to 40 nucleotide sequence of a nucleic acid molecule of the presently disclosed subject matter. In some embodiments, probes comprise 14 to 20 nucleotides, or even longer where desired, such as 30, 40, 50, 60, 100, 200, 300, or 500 nucleotides or up to the full length (for example, the full complement) of any of the nucleotide sequence set forth in the SEQ ID NO: 1. Such fragments can be readily prepared by, for example, directly synthesizing the fragment by chemical synthesis, by application of nucleic acid amplification technology, or by introducing selected sequences into recombinant vectors for recombinant production.

The phrase "hybridizing substantially to" refers to complementary hybridization between a probe nucleic acid molecule and a target nucleic acid molecule and embraces minor mismatches (for example, polymorphisms) that can be accommodated by reducing the stringency of the hybridization and/or wash media to achieve the desired hybridization.

"Stringent hybridization conditions" and "stringent hybridization wash conditions" in the context of nucleic acid hybridization experiments such as Southern and Northern blot analysis are both sequence- and environment-dependent. Longer sequences hybridize specifically at higher temperatures. An extensive guide to the hybridization of nucleic acids is found in Tijssen, 1993. Generally, high stringency hybridization and wash conditions are selected to be about 5° C. lower than the thermal melting point ($T_m$) for the specific sequence at a defined ionic strength and pH. Typically, under "highly stringent conditions" a probe will hybridize specifically to its target subsequence, but to no other sequences. Similarly, medium stringency hybridization and wash conditions are selected to be more than about 5° C. lower than the $T_m$ for the specific sequence at a defined ionic strength and pH. Exemplary medium stringency conditions include hybridizations and washes as for high stringency conditions, except that the temperatures for the hybridization and washes are in some embodiments 8° C., in some embodiments 10° C., in some embodiments 12° C., and in some embodiments 15° C. lower than the $T_m$ for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of highly stringent hybridization conditions for Southern or Northern Blot analysis of complementary nucleic acids having more than about 100 complementary residues is overnight hybridization in 6× standard saline citrate (SSC) or standard saline-phosphate-EDTA (SSPE) at 65° C. (or at 42° C. if 50% formamide is included in the hybridization buffer) containing 5× Denhardt's reagent, 0.5% sodium dodecyl sulfate (SDS), 1 µg/ml poly(A), and 100 µg/ml salmon sperm DNA (50× Denhardt's reagent is 1% (w/v) Ficoll 400, 1% (w/v) polyvinylpyrrolidone, and 1% (w/v) bovine serum albumin; see Sambrook and Russell, 2001, for alternative hybridization and wash conditions and solutions that can be used for the same). An example of highly stringent wash conditions is 15 minutes in 0.1×SSC, 0.1% (w/v) SDS at 65° C. Another example of highly stringent wash conditions is 15 minutes in 0.2×SSC buffer at 65° C. Often, a high stringency wash is preceded by a lower stringency wash to remove background probe signal. An example of medium stringency wash conditions for a duplex of more than about 100 nucleotides is 15 minutes in 1×SSC at 45–55° C. Another example of medium stringency wash for a duplex of more than about 100 nucleotides is 15 minutes in 4–6×SSC at 40° C. For short probes (e.g., about 10 to 50 nucleotides), stringent conditions typically involve salt concentrations of less than about 1 M $Na^+$ ion, typically about 0.01 to 1 M $Na^+$ ion concentration (or other salts) at pH 7.0–8.3, and the temperature is typically at least about 30° C. Stringent conditions can also be achieved with the addition of destabilizing agents such as formamide. In general, a signal to noise ratio of 2-fold (or higher) than that observed for an unrelated probe in the particular hybridization assay indicates detection of a specific hybridization.

The following are examples of hybridization and wash conditions that can be used to clone homologous nucleotide sequences that are substantially identical to reference nucleotide sequences of the presently disclosed subject matter: in some embodiments, a probe and target sequence hybridizes in 7% SDS, 0.5M $NaPO_4$, 1 mm ethylene diamine tetraacetic acid (EDTA) at 50° C. followed by washing in 2×SSC, 0.1% SDS at 50° C.; in some embodiments, a probe and target sequence hybridize in 7% SDS, 0.5 M $NaPO_4$, 1 mm EDTA at 50° C. followed by washing in 1×SSC, 0.1% SDS at 50° C.; in some embodiments, a probe and target sequence hybridize in 7% SDS, 0.5 M $NaPO_4$, 1 mm EDTA at 50° C. followed by washing in 0.5×SSC, 0.1% SDS at 50° C.; in some embodiments, a probe and target sequence hybridize in 7% SDS, 0.5 M $NaPO_4$, 1 mm EDTA at 50° C. followed by washing in 0.1×SSC, 0.1% SDS at 50° C.; in some embodiments, a probe and target sequence hybridize in 7% SDS, 0.5 M $NaPO_4$, 1 mm EDTA at 50° C. followed by washing in 0.1×SSC, 0.1% SDS at 55° C.; in some embodiments, a probe and target sequence hybridize in 7% SDS, 0.5 M $NaPO_4$, 1 mm EDTA at 50° C. followed by washing in 0.1×SSC, 0.1% SDS at 60° C.; and in some embodiments, a probe and target sequence hybridize in 7% SDS, 0.5 M $NaPO_4$, 1 mm EDTA at 50° C. followed by washing in 0.1×SSC, 0.1% SDS at 65° C. In some embodiments, hybridization conditions comprise hybridization in a roller tube for at least 12 hours at 42° C. in 7% SDS, 0.5 M $NaPO_4$, 1 mm EDTA.

As used herein, the term "pre-polypeptide" refers to a polypeptide that is normally targeted to a cellular organelle, such as a chloroplast, and still comprises a transit peptide.

As used herein, the term "purified", when applied to a nucleic acid or polypeptide, denotes that the nucleic acid or polypeptide is essentially free of other cellular components with which it is associated in the natural state. It can be in a homogeneous state although it can be in either a dry or aqueous solution. Purity and homogeneity are typically determined using analytical chemistry techniques such as polyacrylamide gel electrophoresis or high performance liquid chromatography. A polypeptide that is the predominant species present in a preparation is substantially purified. The term "purified" denotes that a nucleic acid or polypeptide gives rise to essentially one band in an electrophoretic gel. Particularly, it means that the nucleic acid or polypeptide is in some embodiments at least about 50% pure, in some embodiments at least about 85% pure, and in some embodiments at least about 99% pure.

Two nucleic acids are "recombined" when sequences from each of the two nucleic acids are combined in a progeny nucleic acid. Two sequences are "directly" recombined when both of the nucleic acids are substrates for recombination. Two sequences are "indirectly recombined" when the sequences are recombined using an intermediate such as a cross-over oligonucleotide. For indirect recombination, no more than one of the sequences is an actual substrate for recombination, and in some cases, neither sequence is a substrate for recombination.

As used herein, the term "regulatory elements" refers to nucleotide sequences involved in controlling the expression of a nucleotide sequence. Regulatory elements can comprise a promoter operably linked to the nucleotide sequence of interest and termination signals. Regulatory sequences also include enhancers and silencers. They also typically encompass sequences required for proper translation of the nucleotide sequence.

As used herein, the term "transformation" refers to a process for introducing heterologous DNA into a plant cell, plant tissue, or plant. Transformed plant cells, plant tissue, or plants are understood to encompass not only the end product of a transformation process, but also transgenic progeny thereof.

As used herein, the terms "transformed", "transgenic", and "recombinant" refer to a host cell or organism such as a bacterium or a plant cell (e.g., a plant) into which a heterologous nucleic acid molecule has been introduced. The nucleic acid molecule can be stably integrated into the genome of the host or the nucleic acid molecule can also be present as an extrachromosomal molecule. Such an extra-chromosomal molecule can be auto-replicating. Transformed cells, tissues, or plants are understood to encompass not only the end product of a transformation process, but also transgenic progeny thereof. A "non-transformed," "non-transgenic", or "non-recombinant" host refers to a wild-type organism, e.g., a bacterium or plant, which does not contain the heterologous nucleic acid molecule.

As used herein, the term "heterologous" as it relates to a nucleotide sequence (or an amino acid sequence encoded thereby) refers not only to a nucleic acid or amino acid sequence that is derived from a species other than the species into which it is introduced, but also refers to a nucleotide sequence from the same species that is manipulated in the genome of a cell or organism of that species such that the genome contains some man made alteration.

Thus, the term "transgenic" refers not only to a cell of *Zea mays*, for example, that comprises a nucleic acid molecule that is not naturally occurring in *Zea mays*, but also includes a cell of *Zea mays*, for example, that comprises a nucleic acid molecule all or parts of which are naturally occurring in *Zea mays*, but have been modified in some form such that the genome of the transgenic plant is identifiably different from that of a naturally occurring *Zea mays*. In some embodiments, the modification comprises introducing one or more additional copies of a *Zea mays* nucleotide sequence into a *Zea mays* cell. In some embodiments, the modification comprises "knocking in" a heterologous nucleotide sequence into the Q protein gene, such that the heterologous nucleotide sequence becomes operably linked to the endogenous Q protein gene promoter.

III. Nucleic Acid Molecules and Polypeptides

III.A. Nucleic Acid Molecules

Embodiments of the presently disclosed subject matter encompass isolated nucleic acid molecules corresponding to members of the prolamin family of *Zea mays* cereal seed storage proteins, and a nucleotide sequence from the promoter region of one such family member that can be used to control expression of operably linked nucleotide sequences. In some embodiments, an isolated nucleic acid molecule of the presently disclosed subject matter comprises a nucleotide sequence that hybridizes under highly stringent conditions of hybridization of 65° C. in 6×SSC, followed by a final washing step of at least 15 minutes at 65° C. in 0.1×SSC to a nucleotide sequence as set forth in SEQ ID NO: 1, or a fragment, domain, or feature thereof. In some embodiments, an isolated nucleic acid molecule of the presently disclosed subject matter comprises a nucleotide sequence having substantial identity to a nucleotide sequence that hybridizes under highly stringent conditions of hybridization of 65° C. in 6×SSC, followed by a final washing step of at least 15 minutes at 65° C. in 0.1×SSC to a nucleotide sequence as set forth in SEQ ID NO: 1, or a fragment, domain, or feature thereof. In some embodiments, the presently disclosed subject matter encompasses an isolated nucleic acid molecule comprising a nucleotide sequence that is complementary to, or the reverse complement of, a nucleotide sequence that hybridizes under highly stringent conditions of hybridization of 65° C. in 6×SSC, followed by a final washing step of at least 15 minutes at 65° C. in 0.1×SSC to a nucleotide sequence listed in SEQ ID NO: 1, or a fragment, domain, or feature thereof. Some embodiments of the presently disclosed subject matter encompass an isolated nucleic acid molecule comprising a nucleotide sequence that is complementary to, or the reverse complement of, a nucleotide sequence that has substantial identity to, or is capable of hybridizing to, a nucleotide sequence that hybridizes under highly stringent conditions of hybridization of 65° C. in 6×SSC, followed by a final washing step of at least 15 minutes at 65° C. in 0.1×SSC to a nucleotide sequence listed in SEQ ID NO: 1, or a fragment, domain, or feature thereof.

In some embodiments, the substantial identity is at least about 60% identity (e.g., 60, 63, 65, 67, or 69% identity), in some embodiments at least about 70% identity (e.g., 70, 73, 75, 77, or 79% identity), in some embodiments about 80% identity (e.g., 80, 83, 85, 87, or 89% identity), in some embodiments about 90% identity (e.g., 90 or 93% identity), in some embodiments about 95% identity, in some embodiments about 97% identity, and in some embodiments at least about 99% identity to the nucleotide sequence listed in SEQ ID NO: 1, or a fragment, domain, or feature thereof.

In some embodiments, the nucleotide sequence having substantial identity comprises an allelic variant of the nucleotide sequence that hybridizes under highly stringent conditions of hybridization of 65° C. in 6×SSC, followed by a final washing step of at least 15 minutes at 65° C. in 0.1×SSC to a nucleotide sequence listed in SEQ ID NO: 1, or a fragment, domain, or feature thereof. In some embodiments, the nucleotide sequence having substantial identity comprises a naturally occurring variant. In some embodiments, the nucleotide sequence having substantial identity comprises a polymorphic variant of the nucleotide sequence that hybridizes under highly stringent conditions of hybridization of 65° C. in 6×SSC, followed by a final washing step of at least 15 minutes at 65° C. in 0.1×SSC to a nucleotide sequence listed in SEQ ID NO: 1, or a fragment, domain, or feature thereof.

In some embodiments, the nucleic acid having substantial identity comprises a deletion or insertion of at least one nucleotide. In some embodiments, the deletion or insertion comprises less than about thirty nucleotides. In some embodiments, the deletion or insertion comprises less than about five nucleotides. In some embodiments, the sequence of the isolated nucleic acid having substantial identity comprises a substitution in at least one codon. In some embodiments, the substitution is conservative.

In some embodiments, the isolated nucleic acid comprises a plurality of regions having a nucleotide sequence that hybridizes under highly stringent conditions of hybridization of 65° C. in 6×SSC, followed by a final washing step of at least 15 minutes at 65° C. in 0.1×SSC to a nucleotide sequence listed in SEQ ID NO: 1, or an exon, domain, or feature thereof.

In some embodiments, the sequence having substantial identity to the nucleotide sequence that hybridizes under highly stringent conditions of hybridization of 65° C. in 6×SSC, followed by a final washing step of at least 15 minutes at 65° C. in 0.1×SSC to a nucleotide sequence listed in SEQ ID NO: 1, or a fragment, domain, or feature thereof, is from a plant. In some embodiments, the plant is a dicot. In some embodiments, the plant is a gymnosperm. In some embodiments, the plant is a monocot. In some embodiments, the monocot is a cereal. In some embodiments, the cereal can be, for example, maize, wheat, barley, oats, rye, millet, sorghum, triticale, secale, einkorn, spelt, emmer, teff, milo, flax, gramma grass, *Tripsacum* sp., or teosinte. In some embodiments, the cereal is rice.

In some embodiments, the nucleic acid is expressed in a specific location or tissue of a plant. In some embodiments, the location or tissue includes, but is not limited to, epidermis, root, vascular tissue, meristem, cambium, cortex, pith, leaf, flower, see, and combinations thereof. In some embodiments, the location or tissue is a seed. In some embodiments, the location or tissue is a protein body of a seed.

Embodiments of the presently disclosed subject matter also relate to a shuffled nucleic acid molecule comprising a plurality of nucleotide sequence fragments, wherein at least one of the fragments corresponds to a region of a nucleotide sequence that hybridizes under highly stringent conditions of hybridization of 65° C. in 6×SSC, followed by a final washing step of at least 15 minutes at 65° C. in 0.1×SSC to a nucleotide sequence listed in SEQ ID NO: 1, and wherein at least two of the plurality of sequence fragments are in an order, from 5' to 3', which is not an order in which the plurality of fragments naturally occur. In some embodiments, all of the fragments in a shuffled nucleic acid comprising a plurality of nucleotide sequence fragments are from a single gene. In some embodiments, the plurality of fragments is derived from at least two different genes. In some embodiments, the shuffled nucleic acid is operably linked to a promoter sequence. In some embodiments, the shuffled nucleic acid comprises a chimeric polynucleotide comprising a promoter sequence operably linked to the shuffled nucleic acid. In some embodiments, the shuffled nucleic acid is contained within a host cell.

III.B. Identifying, Cloning, and Sequencing cDNAs

The cloning and sequencing of the cDNAs of the presently disclosed subject matter is accomplished using techniques known in the art. See generally, Sambrook & Russell, 2001; Silhavy et al., 1984; Ausubel et al., 2002; Ausubel et al., 2003; Reiter et al., 1992; Schultz et al., 1998.

The isolated nucleic acids and polypeptides of the presently disclosed subject matter are usable over a range of plants—monocots and dicots—in particular monocots such as sorghum, rice, wheat, barley, and maize. In some embodiments, the monocot is a cereal. In some embodiments, the cereal can be, for example, maize, wheat, barley, oats, rye, millet, sorghum, triticale, secale, einkorn, spelt, emmer, teff, milo, flax, gramma grass, *Tripsacum* sp., or teosinte. In some embodiments, the cereal is maize. Other plant genera relevant to the presently disclosed subject matter include, but are not limited to, *Cucurbita, Rosa, Vitis, Juglans, Gragaria, Lotus, Medicago, Onobrychis, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium*, and *Triticum*.

The presently disclosed subject matter also provides a method for genotyping a plant or plant part comprising a nucleic acid molecule of the presently disclosed subject matter. Optionally, the plant is a monocot such as, but not limited to, sorghum, rice, maize, or wheat. Genotyping provides a methodology for distinguishing homologs of a chromosome pair and can be used to differentiate segregants in a plant population. Molecular marker methods can be used in phylogenetic studies, characterizing genetic relationships among crop varieties, identifying crosses or somatic hybrids, localizing chromosomal segments affecting monogenic traits, mapping based cloning, and the study of quantitative inheritance (see Clark, 1997; Paterson, 1996).

The method for genotyping can employ any number of molecular marker analytical techniques including, but not limited to, restriction length polymorphisms (RFLPs). As is well known in the art, RFLPs are produced by differences in the DNA restriction fragment lengths resulting from nucleotide differences between alleles of the same gene. Thus, the presently disclosed subject matter provides a method for following segregation of a gene or nucleic acid of the presently disclosed subject matter or chromosomal sequences genetically linked by using RFLP analysis. Linked chromosomal sequences are in some embodiments within 50 centimorgans (cM), in some embodiments within 40 cM, in some embodiments within 30 cM, in some embodiments within 20 cM, in some embodiments within 10 cM, and in some embodiments within 5, 3, 2, or 1 cM of the nucleic acid of the presently disclosed subject matter.

Embodiments of the presently disclosed subject matter also relate to an isolated nucleic acid molecule comprising a nucleotide sequence, its complement (for example, its full complement), or its reverse complement (for example, its full reverse complement), the nucleotide sequence encoding a polypeptide (for example, a biologically active polypeptide or biologically active fragment). In some embodiments, the nucleotide sequence encodes a polypeptide that is an ortholog of a polypeptide comprising a polypeptide sequence listed in SEQ ID NO: 2, or a fragment, domain, repeat, feature, or chimera thereof. In some embodiments, the nucleotide sequence encodes a polypeptide that is an ortholog of a polypeptide comprising a polypeptide sequence having substantial identity to a polypeptide sequence listed in SEQ ID NO: 2, or a fragment, domain, repeat, feature, or chimera thereof. In some embodiments, the nucleotide sequence encodes a polypeptide that is an ortholog of a polypeptide comprising a polypeptide sequence encoded by a nucleotide sequence identical to or having substantial identity to a nucleotide sequence listed in SEQ ID NO: 1, or a fragment, domain, orfeature thereof, or a sequence complementary thereto. In some embodiments, the nucleotide sequence encodes a polypeptide comprising a polypeptide sequence encoded by a nucleotide sequence that hybridizes under highly stringent conditions of hybridization of 65° C. in 6×SSC, followed by a final washing step of at least 15 minutes at 65° C. in 0.1×SSC to a nucleotide sequence listed in SEQ ID NO: 1, or to a sequence complementary thereto. In some embodiments, the nucleotide sequence encodes a functional fragment of a polypeptide of the presently disclosed subject matter.

In some embodiments, the isolated nucleic acid comprises a polypeptide-encoding sequence. In some embodiments, the polypeptide-encoding sequence encodes a polypeptide that is an ortholog of a polypeptide comprising a polypeptide sequence listed in SEQ ID NO: 2, or a fragment thereof. In some embodiments, the polypeptide is a plant polypeptide. In some embodiments, the plant is a dicot. In some embodiments, the plant is a gymnosperm. In some embodiments, the plant is a monocot. In some embodiments, the monocot is a cereal. In some embodiments, the cereal includes, but is not limited to, maize, wheat, barley, oats, rye, millet, sorghum, triticale, secale, einkorn, spelt, emmer, teff, miloflax, gramma grass, *Tripsacum*, and teosinte. In some embodiments, the cereal is maize.

Embodiments of the presently disclosed subject matter also relate to an isolated nucleic acid molecule comprising a nucleotide sequence, its complement (for example, its full complement), or its reverse complement (for example, its full reverse complement), encoding a polypeptide selected from a group comprising one or more of:

(a) a polypeptide sequence encoded by a nucleotide sequence that hybridizes under highly stringent conditions of hybridization of 65° C. in 6×SSC, followed by a final washing step of at least 15 minutes at 65° C. in 0.1×SSC to a nucleotide sequence listed in SEQ ID NO: 1, or a fragment, domain, or feature thereof, or a sequence complementary thereto; and (b) a functional fragment of (a).

In some embodiments, the polypeptide having substantial identity comprises an allelic variant of a polypeptide that is an ortholog of a polypeptide having an amino acid sequence listed in SEQ ID NO: 2, or a fragment, domain, repeat, feature, or chimera thereof. In some embodiments, the isolated nucleic acid comprises a plurality of regions from the polypeptide sequence encoded by a nucleotide sequence that hybridizes under highly stringent conditions of hybridization of 65° C. in 6×SSC, followed by a final washing step of at least 15 minutes at 65° C. in 0.1×SSC to a nucleotide sequence listed in SEQ ID NO: 1, or a fragment, domain, or feature thereof, or a sequence complementary thereto.

III.C. Polypeptides

The presently disclosed subject matter further relates to isolated polypeptides that are orthologs of the polypeptide comprising the amino acid sequences set forth in SEQ ID NO: 2, including biologically active polypeptides. In some embodiments, the polypeptide comprises a polypeptide sequence of an ortholog of a polypeptide listed in SEQ ID NO: 2. In some embodiments, the polypeptide comprises a functional fragment or domain of an ortholog of a polypeptide comprising a polypeptide sequence listed in SEQ ID NO: 2. In some embodiments, the polypeptide comprises a chimera of an ortholog of the polypeptide sequence listed in SEQ ID NO: 2, where the chimera can comprise functional polypeptide motifs, including domains, repeats, post-translational modification sites, or other features. In some embodiments, the polypeptide is a plant polypeptide. In some embodiments, the plant is a dicot. In some embodiments, the plant is a gymnosperm. In some embodiments, the plant is a monocot. In some embodiments, the monocot is a cereal. In some embodiments, the cereal is, for example, maize, wheat, barley, oats, rye, millet, sorghum, triticale, secale, einkorn, spelt, emmer, teff, milo, flax, gramma grass, *Tripsacum*, or teosinte. In some embodiments, the cereal is maize.

In some embodiments, the polypeptide is expressed in a specific location or tissue of a plant. In some embodiments, the location or tissue includes, but is not limited to, epidermis, root, vascular tissue, meristem, cambium, cortex, pith, leaf, flower, seed, and combinations thereof. In some embodiments, the location or tissue is a seed. In some embodiments, the location or tissue is a protein body of a seed.

In some embodiments, isolated polypeptides comprise the amino acid sequences of orthologs of the polypeptides comprising the amino acid sequence set forth in SEQ ID NO: 2, and variants having conservative amino acid modifications. The term "conservative modified variants" refers to polypeptides that can be encoded by nucleotide sequences having degenerate codon substitutions wherein at least one position of one or more selected (or all) codons is substituted with mixed-base and/or deoxyinosine residues (Batzer et al., 1991; Ohtsuka et al., 1985; Rossolini et al., 1994). Additionally, one skilled in the art will recognize that individual substitutions, deletions, or additions to a nucleic acid, peptide, polypeptide, or polypeptide sequence that alters, adds, or deletes a single amino acid or a small percentage of amino acids in the encoded sequence is a "conservative modification" where the modification results in the substitution of an amino acid with a chemically similar amino acid. Conservative modified variants provide similar biological activity as the unmodified polypeptide. Conservative substitution tables listing functionally similar amino acids are known in the art. See Creighton, 1984.

The term "conservatively modified variant" also refers to a peptide having an amino acid residue sequence substantially identical to a sequence of a polypeptide of the presently disclosed subject matter in which one or more residues have been conservatively substituted with a functionally similar residue. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

Amino acid substitutions, such as those which might be employed in modifying the polypeptides described herein, are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all of similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents. Other biologically functionally equivalent changes will be appreciated by those of skill in the art.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (4.5).

The importance of the hydropathic amino acid index in conferring interactive biological function on a protein is generally understood in the art (Kyte & Doolittle, 1982, incorporated herein by reference). It is known that certain amino acids can be substituted for other amino acids having a similar hydropathic index or score and still retain a similar biological activity. In making changes based upon the hydropathic index, substitutions of amino acids can involve amino acids for which the hydropathic indices are in some embodiments within ±2 of the original value, in some embodiments within ±1 of the original value, and in some embodiments within ±0.5 of the original value.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, substitutions of amino acids can involve amino acids for which the hydrophilicity values are in some embodiments within ±2 of the original value, in some embodiments within ±1 of the original value, and in some embodiments within +0.5 of the original value.

While discussion has focused on functionally equivalent polypeptides arising from amino acid changes, it will be appreciated that these changes can be effected by alteration of the encoding DNA, taking into consideration also that the genetic code is degenerate and that two or more codons can code for the same amino acid.

In some embodiments, the sequence having substantial identity contains a deletion or insertion of at least one amino acid. In some embodiments, the deletion or insertion is of less than about ten amino acids. In some embodiments, the deletion or insertion is of less than about three amino acids.

In some embodiments, the sequence having substantial identity encodes a substitution in at least one amino acid.

Embodiments of the presently disclosed subject matter also provide an isolated polypeptide comprising a polypeptide sequence selected from the group consisting of:

(a) a polypeptide sequence having substantial identity to a polypeptide sequence listed in SEQ ID NO: 2, or a domain or feature thereof;

(b) a polypeptide sequence encoded by a nucleotide sequence identical to or having substantial identity to a nucleotide sequence that hybridizes under highly stringent conditions of hybridization of 65° C. in 6×SSC, followed by a final washing step of at least 15 minutes at 65° C. in 0.1×SSC to a nucleotide sequence listed in SEQ ID NO: 1, or an exon, domain, or feature thereof, or a sequence complementary thereto; and (c) a functional fragment of (a) or (b).

In some embodiments, a polypeptide having substantial identity to a polypeptide sequence listed in SEQ ID NO: 2, or a domain or feature thereof, is an allelic variant of the polypeptide sequence listed in SEQ ID NO: 2. In some embodiments, a polypeptide having substantial identity to a polypeptide sequence listed in SEQ ID NO: 2, or a domain or feature thereof, is a naturally occurring variant of the polypeptide sequence listed in SEQ ID NO: 2. In some embodiments, a polypeptide having substantial identity to a polypeptide sequence listed in SEQ ID NO: 2, or a domain or feature thereof, is a polymorphic variant of the polypeptide sequence listed in SEQ ID NO: 2.

In some embodiments, the polypeptide is an ortholog of a polypeptide comprising the amino acid sequence listed in SEQ ID NO: 2. In some embodiments, the polypeptide is a functional fragment or domain of an ortholog of a polypeptide comprising the amino acid sequence listed in SEQ ID NOs: 2. In some embodiments, the polypeptide is a chimera, where the chimera comprises a functional polypeptide domain, including, but not limited to, a domain, a repeat, a post-translational modification site, and combinations thereof. In some embodiments, the polypeptide is a plant polypeptide. In some embodiments, the plant is a dicot. In some embodiments, the plant is a gymnosperm. In some embodiments, the plant is a monocot. In some embodiments, the monocot is a cereal. In some embodiments, the cereal can be, for example, maize, wheat, barley, oats, rye, millet, sorghum, triticale, secale, einkorn, spelt, emmer, teff, milo, flax, gramma grass, *Tripsacum*, or *teosinte*. In some embodiments, the cereal is maize.

In some embodiments, the polypeptide is expressed in a specific location or tissue of a plant. In some embodiments, the location or tissue includes, but is not limited to, epidermis, vascular tissue, meristem, cambium, cortex, or pith. In some embodiments, the location or tissue is leaf or sheath, root, flower, and developing ovule or seed. In some embodiments, the location or tissue can be, for example, epidermis, root, vascular tissue, meristem, cambium, cortex, pith, leaf, or flower. In some embodiments, the location or tissue is a seed.

In some embodiments, the polypeptide sequence is encoded by a nucleotide sequence that hybridizes under highly stringent conditions of hybridization of 65° C. in 6×SSC, followed by a final washing step of at least 15 minutes at 65° C. in 0.1×SSC to the nucleotide sequence of SEQ ID NO: 1, or a fragment, domain, or feature thereof or a sequence complementary thereto, wherein the nucleotide sequence includes a deletion or insertion of at least one nucleotide. In some embodiments, the deletion or insertion is of less than about thirty nucleotides. In some embodiments, the deletion or insertion is of less than about five nucleotides. In some embodiments, the polypeptide sequence encoded by a nucleotide sequence that hybridizes under highly stringent conditions of hybridization of 65° C. in 6×SSC, followed by a final washing step of at least 15 minutes at 65° C. in 0.1×SSC to the nucleotide sequence of SEQ ID NO: 1, or a fragment, domain, or feature thereof or a sequence complementary thereto, includes a substitution of at least one codon. In some embodiments, the substitution is conservative. In some embodiments, the polypeptide sequences having substantial identity to the polypeptide sequence of SEQ ID NO: 2, or a fragment, domain, repeat, feature, or chimera thereof, includes a deletion or insertion of at least one amino acid.

The polypeptides of the presently disclosed subject matter, fragments thereof, or variants thereof, can comprise any number of contiguous amino acid residues from a polypeptide of the presently disclosed subject matter, wherein the number of residues is selected from the group of integers consisting of from 10 to the number of residues in a full-length polypeptide of the presently disclosed subject matter. In some embodiments, the portion or fragment of the polypeptide is a functional polypeptide. The presently disclosed subject matter includes active polypeptides having specific activity of at least in some embodiments 20%, in some embodiments 30%, in some embodiments 40%, in some embodiments 50%, in some embodiments 60%, in some embodiments 70%, in some embodiments 80%, in some embodiments 90%, and in some embodiments 95% that of the native (non-synthetic) endogenous polypeptide. Further, the substrate specificity ($k_{cat}/K_m$) can be substantially identical to the native (non-synthetic), endogenous polypeptide. Typically the $K_m$ will be at least in some embodiments 30%, in some embodiments 40%, in some embodiments 50% of the native, endogenous polypeptide; and in some embodiments at least 60%, in some embodiments 70%, in some embodiments 80%, and in some embodiments 90% of the native, endogenous polypeptide. Methods of assaying and quantifying measures of activity and substrate specificity are well known to those of skill in the art.

The isolated polypeptides of the presently disclosed subject matter can elicit production of an antibody specifically reactive to a polypeptide of the presently disclosed subject matter when presented as an immunogen. Therefore, the polypeptides of the presently disclosed subject matter can be employed as immunogens for constructing antibodies immunoreactive to a polypeptide of the presently disclosed subject matter for such purposes including, but not limited to, immunoassays or polypeptide purification techniques. Immunoassays for determining binding are well known to those of skill in the art and include, but are not limited to, enzyme-linked immunosorbent assays (ELISA) and competitive immunoassays.

Embodiments of the presently disclosed subject matter also relate to chimeric polypeptides encoded by the isolated nucleic acid molecules of the present disclosure including a chimeric polypeptide containing a polypeptide sequence encoded by an isolated nucleic acid containing a nucleotide sequence selected from the group consisting of:
  (a) a nucleotide sequence that hybridizes under highly stringent conditions of hybridization of 65° C. in 6×SSC, followed by a final washing step of at least 15 minutes at 65° C. in 0.1×SSC to a nucleotide sequence listed in SEQ ID NO: 1, or an exon, domain, or feature thereof;
  (b) a nucleotide sequence complementary (for example, fully complementary) to (a); and
  (c) a nucleotide sequence which is the reverse complement (for example, full reverse complement) of (a);
  (d) or a functional fragment thereof.

IV. Controlling and Altering the Expression of Nucleic Acid Molecules

IV.A. General Considerations

One aspect of the presently disclosed subject matter provides compositions and methods for altering (i.e. increasing or decreasing) the level of nucleic acid molecules and/or polypeptides of the presently disclosed subject matter in plants. In particular, the nucleic acid molecules and polypeptides of the presently disclosed subject matter are expressed constitutively, temporally, or spatially (e.g. at developmental stages), in certain tissues, and/or quantities, which are uncharacteristic of non-recombinantly engineered plants. Therefore, the presently disclosed subject matter provides utility in such exemplary applications as altering the specified characteristics identified above.

The isolated nucleic acid molecules of the presently disclosed subject matter are useful for expressing a polypeptide of the presently disclosed subject matter in a recombinantly engineered cell such as a bacterial, yeast, insect, mammalian, or plant cell. Expressing cells can produce the polypeptide in a non-natural condition (e.g. in quantity, composition, location, and/or time) because they have been genetically altered to do so. Those skilled in the art are knowledgeable in the numerous expression systems available for expression of nucleic acids encoding a polypeptide of the presently disclosed subject matter.

Embodiments of the presently disclosed subject matter provide an expression cassette comprising a promoter sequence operably linked to an isolated nucleic acid, the isolated nucleic acid comprising:
  (a) a nucleotide sequence that hybridizes under highly stringent conditions of hybridization of 65° C. in 6×SSC, followed by a final washing step of at least 15 minutes at 65° C. in 0.1×SSC to a nucleotide sequence listed in SEQ ID NO: 1, or a fragment, domain, or feature thereof;
  (b) a nucleotide sequence complementary (for example, fully complementary) to (a); and
  (c) a nucleotide sequence that is the reverse complement (for example, the full reverse complement) of (a).

Further encompassed within the presently disclosed subject matter is a recombinant vector comprising an expression cassette according to the embodiments of the presently disclosed subject matter. Also encompassed are plant cells comprising expression cassettes according to the present disclosure, and plants comprising these plant cells. In some embodiments, the plant is a dicot. In some embodiments, the plant is a gymnosperm. In some embodiments, the plant is a monocot. In some embodiments, the monocot is a cereal. In some embodiments, the cereal is, for example, maize, wheat, barley, oats, rye, millet, sorghum, triticale, secale, einkorn, spelt, emmer, teff, milo, flax, gramma grass, *Tripsacum* or *teosinte*. In some embodiments, the cereal is maize.

In some embodiments, the expression cassette is expressed throughout the plant. In some embodiments, the expression cassette is expressed in a specific location or tissue of a plant. In some embodiments, the location or tissue includes, but is not limited to, epidermis, root, vascular tissue, meristem, cambium, cortex, pith, leaf, flower, seed, and combinations thereof. In some embodiments, the location or tissue is a seed. In some embodiments, the location or tissue is a protein body of a seed.

Embodiments of the presently disclosed subject matter also relate to an expression vector comprising a nucleic acid molecule selected from the group consisting of:
  (a) a nucleic acid encoding a polypeptide as listed in SEQ ID NO: 2, or ortholog thereof;
  (b) a fragment, domain, or featured region of a nucleotide sequence that hybridizes under highly stringent conditions of hybridization of 65° C. in 6×SSC, followed by a final washing step of at least 15 minutes at 65° C. in 0.1×SSC to a nucleotide sequence listed in SEQ ID NO: 1; and
  (c) a complete nucleotide sequence that hybridizes under highly stringent conditions of hybridization of 65° C. in 6×SSC, followed by a final washing step of at least 15 minutes at 65° C. in 0.1×SSC to a nucleotide sequence listed in SEQ ID NO: 1, or a fragment thereof, in combination with a heterologous sequence.

In some embodiments, the expression vector comprises one or more elements including, but not limited to, a promoter-enhancer sequence, a selection marker sequence, an origin of replication, an epitope tag-encoding sequence, and an affinity purification tag-encoding sequence. In some embodiments, the promoter-enhancer sequence comprises, for example, the cauliflower mosaic virus (CaMV) 35S promoter, the CaMV 19S promoter, the tobacco PR-1a promoter, the ubiquitin promoter, or the phaseolin promoter. In some embodiments, the promoter is operable in plants, and in some embodiments, the promoter is a constitutive or inducible promoter. In some embodiments, the selection marker sequence encodes an antibiotic resistance gene. In some embodiments, the epitope tag sequence encodes the V5 epitope tag (GKPIPNPLLGLDST; SEQ ID NO: 9; Southern et al., 1991), the peptide FHHTT (SEQ ID NO: 10), hemaglutinin, or glutathione-5-transferase. In some embodiments the affinity purification tag sequence encodes a polyamino acid sequence or a polypeptide. In some embodiments, the polyamino acid sequence comprises polyhistidine. In some embodiments, the polypeptide is chitin-binding domain or glutathione-5-transferase. In some embodiments, the affinity purification tag sequence comprises an intein encoding sequence.

In some embodiments, the expression vector comprises a eukaryotic expression vector, and in some embodiments, the expression vector comprises a prokaryotic expression vector. In some embodiments, the eukaryotic expression vector comprises a tissue-specific promoter. In some embodiments, the expression vector is operable in plants.

Embodiments of the presently disclosed subject matter also relate to a cell comprising a nucleic acid construct comprising an expression vector and a nucleic acid comprising a nucleic acid encoding a polypeptide that is an ortholog of a polypeptide as listed in SEQ ID NO: 2, or a nucleotide sequence that hybridizes under highly stringent conditions of hybridization of 65° C. in 6×SSC, followed by a final washing step of at least 15 minutes at 65° C. in 0.1×SSC to a nucleotide sequence listed in SEQ ID NO: 1, or a subsequence thereof, in combination with a heterologous sequence.

In some embodiments, the cell is a bacterial cell, a fungal cell, a plant cell, or an animal cell. In some embodiments, the polypeptide is expressed in a specific location or tissue of a plant. In some embodiments, the location or tissue includes, but is not limited to, epidermis, root, vascular tissue, meristem, cambium, cortex, pith, leaf, flower, seed, and combinations thereof. In some embodiments, the location or tissue is a seed.

Prokaryotic cells including, but not limited to, *Escherichia coli* and other microbial strains known to those in the art, can be used a host cells. Methods for expressing polypeptides in prokaryotic cells are well known to those in the art and can be found in many laboratory manuals such as Sambrook & Russell, 2001. A variety of promoters, ribosome binding sites, and operators to control expression are available to those skilled in the art, as are selectable markers such as antibiotic resistance genes. The type of vector is chosen to allow for optimal growth and expression in the selected cell type.

A variety of eukaryotic expression systems are available such as, for example, yeast, insect cell lines, plant cells, and mammalian cells. Expression and synthesis of heterologous polypeptides in yeast is well known (see Sherman et al., 1982). Yeast strains widely used for production of eukaryotic polypeptides are *Saccharomyces cerevisiae* and *Pichia pastoris*, and vectors, strains, and protocols for expression are available from commercial suppliers (e.g., Invitrogen Corp., Carlsbad, Calif., United States of America).

Mammalian cell systems can be transformed with expression vectors for production of polypeptides. Suitable host cell lines available to those in the art include, but are not limited to, the HEK293, BHK21, and CHO cells lines. Expression vectors for these cells can include expression control sequences such as an origin of replication, a promoter, (e.g., the CMV promoter, a Herpes Simplex Virus thymidine kinase (HSV-tk) promoter or phosphoglycerate kinase (pgk) promoter), an enhancer, and polypeptide processing sites such as ribosome binding sites, RNA splice sites, polyadenylation sites, and transcription terminator sequences. Other animal cell lines useful for the production of polypeptides are available commercially or from depositories such as the American Type Culture Collection (Manassas, Va., United States of America).

Expression vectors for expressing polypeptides in insect cells are usually derived from baculovirus or other viruses known in the art. A number of suitable insect cell lines are available including, but not limited to, mosquito larvae, silkworm, armyworm (for example, *Spodoptera frugiperda*), moth, and *Drosophila* cell lines.

Methods of transforming animal and lower eukaryotic cells are known. Numerous methods can be used to introduce heterologous DNA into eukaryotic cells including, but not limited to, calcium phosphate precipitation, fusion of the recipient cell with bacterial protoplasts containing the DNA, treatment of the recipient cells with liposomes containing the DNA, DEAE dextran, electroporation, biolistics, and microinjection of the DNA directly into the cells. Transformed cells are cultured using means well known in the art (see Kuchler, 1997).

Once a polypeptide of the presently disclosed subject matter is expressed it can be isolated and purified from the expressing cells using methods known to those skilled in the art. The purification process can be monitored using Western blot techniques, radioimmunoassay, or other standard immunoassay techniques. Polypeptide purification techniques are commonly known and used by those skilled in the art (see Scopes, 1982; Deutscher, 1990).

Embodiments of the presently disclosed subject matter provide a method for producing a recombinant polypeptide in which the expression vector comprise one or more elements including, but not limited to, a promoter-enhancer sequence, a selection marker sequence, an origin of replication, an epitope tag-encoding sequence, and an affinity purification tag-encoding sequence. In some embodiments, the nucleic acid construct comprises an epitope tag-encoding sequence and the isolating step employs an antibody specific for the epitope tag. In some embodiments, the nucleic acid construct comprises a polyamino acid-encoding sequence and the isolating step employs a resin comprising a polyamino acid binding substance, in some embodiments where the polyamino acid is polyhistidine and the polyamino acid binding resin is nickel-charged agarose resin. In some embodiments, the nucleic acid construct comprises a polypeptide-encoding sequence and the isolating step employs a resin comprising a polypeptide binding substance. In some embodiments, the polypeptide is a chitin-binding domain and the resin contains chitin-sepharose.

The polypeptides of the presently disclosed subject matter can be synthesized using non-cellular synthetic methods known to those in the art. Techniques for solid phase synthesis are disclosed in Barany & Merrifield, 1980; Merrifield et al., 1963; Stewart & Young, 1984.

The presently disclosed subject matter further provides a method for modifying (i.e. increasing or decreasing) the concentration or composition of a polypeptide of the presently disclosed subject matter in a plant or part thereof. Modification can be effected by increasing or decreasing the concentration and/or the composition (i.e. the ration of the polypeptides of the presently disclosed subject matter) in a plant. The method comprises introducing into a plant cell an expression cassette comprising a nucleic acid molecule of the presently disclosed subject matter as disclosed above to obtain a transformed plant cell or tissue, and culturing the transformed plant cell or tissue. The nucleic acid molecule can be under the regulation of a constitutive or inducible promoter. The method can further comprise inducing or repressing expression of a nucleic acid molecule of a sequence in the plant for a time sufficient to modify the concentration and/or composition in the plant or plant part.

A plant or plant part having modified expression of a nucleic acid molecule of the presently disclosed subject matter can be analyzed and selected using methods known to those skilled in the art including, but not limited to, Southern blotting, DNA sequencing, or PCR analysis using primers specific to the nucleic acid molecule and detecting amplicons produced therefrom.

In general, a concentration or composition is increased or decreased by at least in some embodiments 5%, in some embodiments 10%, in some embodiments 20%, in some embodiments 30%, in some embodiments 40%, in some embodiments 50%, in some embodiments 60%, in some embodiments 70%, in some embodiments 80%, and in some embodiments 90% relative to a native control plant, plant part, or cell lacking the expression cassette.

IV.B. Homologous Recombination

In some embodiments, at least one genomic copy corresponding to a nucleotide sequence of the presently disclosed subject matter is modified in the genome of the plant by homologous recombination as further illustrated in Paszkowski et al., 1988. This technique uses the ability of homologous sequences to recognize each other and to exchange nucleotide sequences between respective nucleic acid molecules by a process known in the art as homologous recombination. Homologous recombination can occur between the chromosomal copy of a nucleotide sequence in a cell and an incoming copy of the nucleotide sequence introduced in the cell by transformation. Specific modifications are thus accurately introduced in the chromosomal copy of the nucleotide sequence. In some embodiments, the regulatory elements of the nucleotide sequence of the presently disclosed subject matter are modified. Such regulatory elements are easily obtainable by screening a genomic library using the nucleotide sequence of the presently disclosed subject matter, or a portion thereof, as a probe. The existing regulatory elements are replaced by different regulatory elements, thus altering expression of the nucleotide sequence, or they are mutated or deleted, thus abolishing the expression of the nucleotide sequence. In some embodiments, the nucleotide sequence is modified by deletion of a part of the nucleotide sequence or the entire nucleotide sequence, or by mutation. Expression of a mutated polypeptide in a plant cell is also provided in the presently disclosed subject matter. Recent refinements of this technique to disrupt endogenous plant genes have been disclosed (Kempin et al., 1997 and Miao & Lam, 1995).

In some embodiments, a mutation in the chromosomal copy of a nucleotide sequence is introduced by transforming a cell with a chimeric oligonucleotide composed of a contiguous stretch of RNA and DNA residues in a duplex conformation with double hairpin caps on the ends. An additional feature of the oligonucleotide is for example the presence of 2'-O-methylation at the RNA residues. The RNA/DNA sequence is designed to align with the sequence of a chromosomal copy of a nucleotide sequence of the presently disclosed subject matter and to contain the desired nucleotide change. For example, this technique is further illustrated in U.S. Pat. No. 5,501,967 and Zhu et al., 1999.

IV.C. Overexpression in a Plant Cell

In some embodiments, a nucleotide sequence of the presently disclosed subject matter encoding a polypeptide is over-expressed. Examples of nucleic acid molecules and expression cassettes for over-expression of a nucleic acid molecule of the presently disclosed subject matter are disclosed above. Methods known to those skilled in the art of over-expression of nucleic acid molecules are also encompassed by the presently disclosed subject matter.

In some embodiments, the expression of the nucleotide sequence of the presently disclosed subject matter is altered in every cell of a plant. This can be obtained, for example, though homologous recombination or by insertion into a chromosome. This can also be obtained, for example, by expressing a sense or antisense RNA, zinc finger polypeptide or ribozyme under the control of a promoter capable of expressing the sense or antisense RNA, zinc finger polypeptide, or ribozyme in every cell of a plant. Constitutive, inducible, tissue-specific, or developmentally-regulated expression are also within the scope of the presently disclosed subject matter and result in a constitutive, inducible, tissue-specific, or developmentally-regulated alteration of the expression of a nucleotide sequence of the presently disclosed subject matter in the plant cell. Constructs for expression of the sense or antisense RNA, zinc finger polypeptide, or ribozyme, or for over-expression of a nucleotide sequence of the presently disclosed subject matter, can be prepared and transformed into a plant cell according to the teachings of the presently disclosed subject matter, for example, as disclosed herein.

IV.D. Construction of Plant Expression Vectors

Coding sequences intended for expression in transgenic plants can be first assembled in expression cassettes operably linked to a suitable promoter expressible in plants. The expression cassettes can also comprise any further sequences required or selected for the expression of the transgene. Such sequences include, but are not limited to, transcription terminators, extraneous sequences to enhance expression such as introns, vital sequences, and sequences intended for the targeting of the gene product to specific organelles and cell compartments. These expression cassettes can then be easily transferred to the plant transformation vectors disclosed below. The following is a description of various components of typical expression cassettes.

IV.D.1. Promoters

The selection of the promoter used in expression cassettes can determine the spatial and temporal expression pattern of the transgene in the transgenic plant. Selected promoters can express transgenes in specific cell types (for example, leaf epidermal cells, mesophyll cells, root cortex cells, and/or endosperm cells) or in specific tissues or organs (for example, roots, leaves, flowers, and/or seeds) and the selection can reflect the desired location for accumulation of the gene product. Alternatively, the selected promoter can drive expression of the gene under various inducing conditions. Promoters vary in their strengths; i.e., their abilities to promote transcription. Depending upon the host cell system utilized, any one of a number of suitable promoters can be used, including the gene's native promoter. The following are non-limiting examples of promoters that can be used in expression cassettes.

IV.D.1.a. Constitutive Expression: the Ubiquitin Promoter

Ubiquitin is a gene product known to accumulate in many cell types and its promoter has been cloned from several species for use in transgenic plants (e.g. sunflower—Binet et al., 1991; maize—Christensen & Quail, 1989; and *Arabidopsis*—Callis et al., 1990; Norris et al., 1993). The maize ubiquitin promoter has been developed in transgenic monocot systems and its sequence and vectors constructed for monocot transformation are disclosed in the patent publication EP 0 342 926 (to Lubrizol) which is herein incorporated by reference. Taylor et al., 1993, describes a vector (pAHC25) that comprises the maize ubiquitin promoter and first intron and its high activity in cell suspensions of numerous monocotyledons when introduced via microprojectile bombardment. The *Arabidopsis* ubiquitin promoter is suitable for use with the nucleotide sequences of the presently disclosed subject matter. The ubiquitin promoter is suitable for gene expression in transgenic plants, both monocotyledons and dicotyledons. Suitable vectors are derivatives of pAHC25 or any of the transformation vectors disclosed herein, modified by the introduction of the appropriate ubiquitin promoter and/or intron sequences.

IV.D.1.b. Constitutive Expression: the CaMV 35S Promoter

Construction of the plasmid pCGN1761 is disclosed in the published patent application EP 0 392 225 (Example 23), which is hereby incorporated by reference. pCGN1761 contains the "double" CaMV 35S promoter and the tml transcriptional terminator with a unique EcoRI site between the promoter and the terminator and has a pUC-type backbone. A derivative of pCGN1761 is constructed which has a modified polylinker that includes Not[and XhoI sites in addition to the existing EcoRI site. This derivative is designated pCGN1761ENX. pCGN1761ENX is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by Hind III, Sph I, Sal I, and Xba I sites 5' to the promoter and Xba I, BamH I and Bgl I sites 3' to the terminator for transfer to transformation vectors such as those disclosed below. Furthermore, the double 35S promoter fragment can be removed by 5' excision with Hind III, Sph I, Sal I, Xba I, or Pst I, and 3' excision with any of the polylinker restriction sites (EcoR I, Not I or Xho I) for replacement with another promoter. If desired, modifications around the cloning sites can be made by the introduction of sequences that can enhance translation. This is particularly useful when overexpression is desired. For example, pCGN1761ENX can be modified by optimization of the translational initiation site as disclosed in Example 37 of U.S. Pat. No. 5,639,949, incorporated herein by reference.

IV.D.1.c. Constitutive Expression: the Actin Promoter

Several isoforms of actin are known to be expressed in most cell types and consequently the actin promoter can be used as a constitutive promoter. In particular, the promoter from the rice ActI gene has been cloned and characterized (McElroy et al., 1990). A 1.3 kilobase (kb) fragment of the promoter was found to contain all the regulatory elements required for expression in rice protoplasts. Furthermore, numerous expression vectors based on the ActI promoter have been constructed specifically for use in monocotyledons (McElroy et al., 1991). These incorporate the ActI-intron 1, AdhI 5' flanking sequence (from the maize alcohol dehydrogenase gene) and AdhI-intron 1 and sequence from the CaMV 35S promoter. Vectors showing highest expression were fusions of 35S and ActI intron or the ActI 5' flanking sequence and the ActI intron. Optimization of sequences around the initiating ATG (of the β-glucuronidase (GUS) reporter gene) also enhanced expression. The promoter expression cassettes disclosed in McElroy et al., 1991, can be easily modified for gene expression and are particularly suitable for use in monocotyledonous hosts. For example, promoter-containing fragments are removed from the McElroy constructions and used to replace the double 35S promoter in pCGN 1761ENX, which is then available for the insertion of specific gene sequences. The fusion genes thus constructed can then be transferred to appropriate transformation vectors. In a separate report, the rice ActI promoter with its first intron has also been found to direct high expression in cultured barley cells (Chibbar et al., 1993).

IV.D.1.d. Inducible Expression: PR-1 Promoters

The double 35S promoter in pCGN1761ENX can be replaced with any other promoter of choice that will result in suitably high expression levels. By way of example, one of the chemically regulatable promoters disclosed in U.S. Pat. No. 5,614,395, such as the tobacco PR-1a promoter, can replace the double 35S promoter. Alternately, the *Arabidopsis* PR-1 promoter disclosed in Lebel et al., 1998, can be used. The promoter of choice can be excised from its source by restriction enzymes, but can alternatively be PCR-amplified using primers that carry appropriate terminal restriction sites. Should PCR-amplification be undertaken, the promoter can be re-sequenced to check for amplification errors after the cloning of the amplified promoter in the target vector. The chemically/pathogen regulatable tobacco PR-1a promoter is cleaved from plasmid pCIB1004 (for construction, see example 21 of EP 0 332 104, which is hereby incorporated by reference) and transferred to plasmid pCGN1761ENX (Uknes et al., 1992). pCIB1004 is cleaved with Nco I and the resulting 3' overhang of the linearized fragment is rendered blunt by treatment with T4 DNA polymerase. The fragment is then cleaved with Hind III and the resultant PR-1a promoter-containing fragment is gel purified and cloned into pCGN1761ENX from which the double 35S promoter has been removed. This is accomplished by cleavage with Xho I and blunting with T4 polymerase, followed by cleavage with Hind III, and isolation of the larger vector-terminator containing fragment into which the pCIB1004 promoter fragment is cloned. This generates a pCGN1761ENX derivative with the PR-1 a promoter and the tml terminator and an intervening polylinkerwith unique EcoR I and Not I sites. The selected coding sequence can be inserted into this vector, and the fusion products (i.e. promoter-gene-terminator) can subsequently be transferred to any selected transformation vector, including those disclosed herein. Various chemical regulators can be employed to induce expression of the selected coding sequence in the plants transformed according to the presently disclosed subject matter, including the benzothiadiazole, isonicotinic acid, and salicylic acid compounds disclosed in U.S. Pat. Nos. 5,523,311 and 5,614,395.

IV.D.1.e. Inducible Expression: an Ethanol-Inducible Promoter

A promoter inducible by certain alcohols or ketones, such as ethanol, can also be used to confer inducible expression of a coding sequence of the presently disclosed subject matter. Such a promoter is for example the alcA gene promoter from *Aspergillus nidulans* (Caddick et al., 1998). In *A. nidulans*, the alcA gene encodes alcohol dehydrogenase I, the expression of which is regulated by the AlcR transcription factors in presence of the chemical inducer. For the purposes of the presently disclosed subject matter, the CAT coding sequences in plasmid palcA:CAT comprising a alcA gene promoter sequence fused to a minimal 35S promoter (Caddick et al., 1998) are replaced by a coding sequence of the presently disclosed subject matter to form an expression cassette having the coding sequence under the control of the alcA gene promoter. This is carried out using methods known in the art.

IV.D.1.f. Inducible Expression: a Glucocorticoid-Inducible Promoter

Induction of expression of a nucleotide sequence of the presently disclosed subject matter using systems based on steroid hormones is also provided. For example, a glucocorticoid-mediated induction system is used (Aoyama & Chua, 1997) and gene expression is induced by application of a glucocorticoid, for example a synthetic glucocorticoid, for example dexamethasone, at a concentration ranging in some embodiments from 0.1 mM to 1 mM, and in some embodiments from 10 mM to 100 mM. For the purposes of the presently disclosed subject matter, the luciferase gene sequences Aoyama & Chua, 1997 are replaced by a nucleotide sequence of the presently disclosed subject matterto form an expression cassette having a nucleotide sequence of the presently disclosed subject matter under the control of six copies of the GAL4 upstream activating sequences fused to the 35S minimal promoter. This is carried out using methods known in the art. The trans-acting factor comprises the GAL4 DNA-binding domain (Keegan et al., 1986) fused to the transactivating domain of the herpes viral polypeptide VP16 (Triezenberg et al., 1988) fused to the hormone-binding domain of the rat glucocorticoid receptor (Picard et al., 1988). The expression of the fusion polypeptide is controlled either by a promoter known in the art or disclosed herein. A plant comprising an expression cassette comprising a nucleotide sequence of the presently disclosed subject matter fused to the 6× GAL4/minimal promoter is also provided. Thus, tissue- or organ-specificity of the fusion polypeptide is achieved leading to inducible tissue- or organ-specificity of the nucleotide sequence to be expressed.

IV.D.1.g. Root Specific Expression

Another pattern of gene expression is root expression. A suitable root promoter is the promoter of the maize metallothionein-like (MTL) gene disclosed in de Framond, 1991, and also in U.S. Pat. No. 5,466,785, each of which is incorporated herein by reference. This "MTL" promoter is transferred to a suitable vector such as pCGN1761ENX for the insertion of a selected gene and subsequent transfer of the entire promoter-gene-terminator cassette to a transformation vector of interest.

IV.D.1.h. Wound-Inducible Promoters

Wound-inducible promoters can also be suitable for gene expression. Numerous such promoters have been disclosed (e.g. Xu et al., 1993; Logemann et al., 1989; Rohrmeier & Lehle, 1993; Firek et al., 1993; Warner et al., 1993) and all are suitable for use with the presently disclosed subject matter. Logemann et al., describe the 5' upstream sequences of the dicotyledonous potato wun1 gene. Xu et al. show that a wound-inducible promoter from the dicotyledon potato (pin2) is active in the monocotyledon rice. Further, Rohrmeier & Lehle describe the cloning of the maize Wip1 cDNA that is wound induced and which can be used to isolate the cognate promoter using standard techniques. Similarly, Firek et al. and Warner et al. have disclosed a wound-induced gene from the monocotyledon *Asparagus officinalis*, which is expressed at local wound and pathogen invasion sites. Using cloning techniques well known in the art, these promoters can be transferred to suitable vectors, fused to the genes pertaining to the presently disclosed subject matter, and used to express these genes at the sites of plant wounding.

IV.D.1.i. Pith-Preferred Expression

PCT International Publication WO 93/07278, which is herein incorporated by reference, describes the isolation of the maize trpA gene, which is preferentially expressed in pith cells. The gene sequence and promoter extending up to −1726 basepairs (bp) from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

IV.D.1.j. Leaf-Specific Expression

A maize gene encoding phosphoenol carboxylase (PEPC) has been disclosed by Hudspeth & Grula, 1989. Using standard molecular biological techniques, the promoter for this gene can be used to drive the expression of any gene in a leaf-specific manner in transgenic plants.

IV.D.1.k. Pollen-Specific Expression

WO 93/07278 describes the isolation of the maize calcium-dependent protein kinase (CDPK) gene that is expressed in pollen cells. The gene sequence and promoter extend up to 1400 basepairs (bp) from the start of transcription. Using standard molecular biological techniques, this promoter or parts thereof can be transferred to a vector such as pCGN1761 where it can replace the 35S promoter and be used to drive the expression of a nucleotide sequence of the presently disclosed subject matter in a pollen-specific manner.

IV.D.1.l. Seed-Specific Expression

In some embodiments, nucleic acid molecules of the presently disclosed subject matter can be expressed in the seed, and/or in a protein body present within a seed. As disclosed herein, a nucleotide sequence isolated from the Q protein gene, SEQ ID NO: 6, can be used to direct expression of heterologous sequences in the seeds of plants. Using standard molecular biological techniques, this promoter or parts thereof can be transferred to a vector such as pCGN1761 where it can replace the 35S promoter and be used to drive the expression of a nucleotide sequence of the presently disclosed subject matter in a seed-specific manner.

IV.D.2. Transcriptional Terminators

A variety of transcriptional terminators are available for use in expression cassettes. These are responsible for termination of transcription and correct mRNA polyadenylation. Appropriate transcriptional terminators are those that are known to function in plants and include the CaMV 35S terminator, the tml terminator, the nopaline synthase terminator, and the pea rbcS E9 terminator. These can be used in both monocotyledons and dicotyledons. In addition, a gene's native transcription terminator can be used.

IV.D.3. Sequences for the Enhancement or Regulation of Expression

Numerous sequences have been found to enhance gene expression from within the transcriptional unit and these sequences can be used in conjunction with the genes of the presently disclosed subject matter to increase their expression in transgenic plants.

Various intron sequences have been shown to enhance expression, particularly in monocotyledonous cells. For example, the introns of the maize AdhI gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., 1987). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV; the "W-sequence"), Maize Chlorotic Mottle Virus (MCMV), and Alfalfa Mosaic Virus (AMV) have been shown to be effective in enhancing expression (see e.g. Gallie et al., 1987; Skuzeski et al., 1990). Other leader sequences known in the art include, but are not limited to, picornavirus leaders, for example, encephalomyocarditis virus (EMCV) leader (5' noncoding region; see Elroy-Stein et al., 1989); potyvirus leaders, for example, from Tobacco Etch Virus (TEV; see Allison et al., 1986); Maize Dwarf Mosaic Virus (MDMV; see Kong & Steinbiss 1998); human immunoglobulin heavy-chain binding polypeptide (BiP) leader (Macejak & Sarnow, 1991); untranslated leader from the coat polypeptide mRNA of alfalfa mosaic virus (AMV; RNA 4; see Jobling & Gehrke, 1987); tobacco mosaic virus (TMV) leader (Gallie et al., 1989); and Maize Chlorotic Mottle Virus (MCMV) leader (Lommel et al., 1991). See also, Della-Cioppa et al., 1987.

In addition to incorporating one or more of the aforementioned elements into the 5' regulatory region of a target expression cassette of the presently disclosed subject matter, other elements can also be incorporated. Such elements include, but are not limited to, a minimal promoter. By minimal promoter it is intended that the basal promoter elements are inactive or nearly so in the absence of upstream or downstream activation. Such a promoter has low background activity in plants when there is no transactivator present or when enhancer or response element binding sites are absent. One minimal promoter that is particularly useful for target genes in plants is the Bz1 minimal promoter, which is obtained from the bronze1 gene of maize. The Bz1 core promoter is obtained from the "myc" mutant Bz1-luciferase construct pBz1 LucR98 via cleavage at the NheI site located at positions −53 to −58 (Roth et al., 1991). The derived Bz1 core promoter fragment thus extends from positions −53 to +227 and includes the Bz1 intron-1 in the 5' untranslated region. Also useful for the presently disclosed subject matter is a minimal promoter created by use of a synthetic TATA element. The TATA element allows recognition of the promoter by RNA polymerase factors and confers a basal level of gene expression in the absence of activation (see generally, Mukumoto et al., 1993; Green, 2000.

IV.D.4. Targeting of the Gene Product within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various polypeptides that is cleaved during chloroplast import to yield the mature polypeptides (see e.g., Comai et al., 1988). These signal sequences can be fused to heterologous gene products to affect the import of heterologous products into the chloroplast (Van den Broeck et al., 1985). DNA encoding for appropriate signal sequences can be isolated from the 5' end of the cDNAs encoding the ribulose-1,5-bisphosphate carboxylase/oxygenase (RUBISCO) polypeptide, the chlorophyll a/b binding (CAB) polypeptide, the 5-enol-pyruvyl shikimate-3-phosphate (EPSP) synthase enzyme, the GS2 polypeptide and many other polypeptides which are known to be chloroplast localized. See also, the section entitled "Expression With Chloroplast Targeting" in Example 37 of U.S. Pat. No. 5,639,949, herein incorporated by reference.

Other gene products can be localized to other organelles such as the mitochondrion and the peroxisome (e.g. Unger et al., 1989). The cDNAs encoding these products can also be manipulated to effect the targeting of heterologous gene products to these organelles. Examples of such sequences are the nuclear-encoded ATPases and specific aspartate amino transferase isoforms for mitochondria. Targeting cellular polypeptide bodies has been disclosed by Rogers et al., 1985.

In addition, sequences have been characterized that control the targeting of gene products to other cell compartments. Amino terminal sequences are responsible for targeting to the endoplasmic reticulum (ER), the apoplast, and extracellular secretion from aleurone cells (Koehler & Ho, 1990). Additionally, amino terminal sequences in conjunction with carboxy terminal sequences are responsible for vacuolar targeting of gene products (Shinshi et al., 1990).

By the fusion of the appropriate targeting sequences disclosed above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected can include the known cleavage site, and the fusion constructed can take into account any amino acids after the cleavage site that are required for cleavage. In some cases this requirement can be fulfilled by the addition of a small number of amino acids between the cleavage site and the transgene ATG or, alternatively, replacement of some amino acids within the transgene sequence. Fusions constructed for chloroplast import can be tested for efficacy of chloroplast uptake by in vitro translation of in vitro transcribed constructions followed by in vitro chloroplast uptake using techniques disclosed by Bartlett et al., 1982 and Wasmann et al., 1986. These construction techniques are well known in the art and are equally applicable to mitochondria and peroxisomes.

And finally, using a nucleotide sequence comprising the Q protein promoter (SEQ ID NO: 6), seed-specific expression of a heterologous sequence can be accomplished. Thus, an expression construct comprising a heterologous coding sequence operably linked to SEQ ID NO: 6 can be employed to direct expression of the nucleotide sequence in the seed, and in some embodiments, can be used to produce protein bodies comprising the polypeptide encoded by the heterologous coding sequence.

The above-disclosed mechanisms for cellular targeting can be utilized not only in conjunction with their cognate promoters, but also in conjunction with heterologous promoters so as to effect a specific cell-targeting goal under the transcriptional regulation of a promoter that has an expression pattern different from that of the promoter from which the targeting signal derives.

IV.E. Construction of Plant Transformation Vectors

Numerous transformation vectors available for plant transformation are known to those of ordinary skill in the plant transformation art, and the genes pertinent to the presently disclosed subject matter can be used in conjunction with any such vectors. The selection of vector will depend upon the selected transformation technique and the target species for transformation. For certain target species, different antibiotic or herbicide selection markers might be employed. Selection markers used routinely in transformation include the nptII gene, which confers resistance to kanamycin and related antibiotics (Messing & Vieira, 1982; Bevan et al., 1983); the bar gene, which confers resistance to the herbicide phosphinothricin (White et al., 1990; Spencer et al., 1990); the hph gene, which confers resistance to the antibiotic hygromycin (Blochinger & Diggelmann, 1984); the dhfr gene, which confers resistance to methotrexate (Bourouis & Jarry, 1983); the EPSP synthase gene, which confers resistance to glyphosate (U.S. Pat. Nos.

4,940,935 and 5,188,642); and the mannose-6-phosphate isomerase gene, which provides the ability to metabolize mannose (U.S. Pat. Nos. 5,767,378 and 5,994,629).

IV.E.1. Vectors Suitable for *Agrobacterium* Transformation

Many vectors are available for transformation using *Agrobacterium tumefaciens*. These typically carry at least one T-DNA border sequence and include vectors such as pBIN19 (Bevan, 1984). Below, the construction of two typical vectors suitable for *Agrobacterium* transformation is disclosed.

IV.E.1.a. PCIB200 and PCIB2001

The binary vectors pCIB200 and pCIB2001 are used for the construction of recombinant vectors for use with *Agrobacterium* and are constructed in the following manner. pTJS75kan is created by Nar I digestion of pTJS75 (Schmidhauser & Helinski, 1985) allowing excision of the tetracycline-resistance gene, followed by insertion of an Acc I fragment from pUC4K carrying an NPTII sequence (Messing & Vieira, 1982: Bevan et al., 1983: McBride & Summerfelt. 1990). Xho I linkers are ligated to the EcoRV fragment of PCIB7 which contains the left and right T-DNA borders, a plant selectable nos/nptII chimeric gene and the pUC polylinker (Rothstein et al., 1987), and the Xho I-digested fragment are cloned into Sal I-digested pTJS75kan to create pCIB200 (see also EP 0 332 104, example 19). pCIB200 contains the following unique polylinker restriction sites: EcoR I, Sst I, Kpn 1, Bgl II, Xba I, and Sal I. pCIB2001 is a derivative of pCIB200 created by the insertion into the polylinker of additional restriction sites. Unique restriction sites in the polylinker of pCIB2001 are EcoR I, Sst I, Kpn I, Bgl II, Xba I, Sal I, Mlu I, Bcl I, Avr II, Apa I, Hpa I, and Stu I. pCIB2001, in addition to containing these unique restriction sites, also has plant and bacterial kanamycin selection, left and right T-DNA borders for *Agrobacterium*-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

IV.E.1.b. pCIB10 and Hygromycin Selection Derivatives Thereof

The binary vector pCIB10 contains a gene encoding kanamycin resistance for selection in plants, T-DNA right and left border sequences, and incorporates sequences from the wide host-range plasmid pRK252 allowing it to replicate in both *E. coli* and *Agrobacterium*. Its construction is disclosed by Rothstein et al., 1987. Various derivatives of pCIB10 can be constructed which incorporate the gene for hygromycin B phosphotransferase disclosed by Gritz & Davies, 1983. These derivatives enable selection of transgenic plant cells on hygromycin only (pCIB743), or hygromycin and kanamycin (pCIB715, pCIB717).

IV.E.2. Vectors Suitable for non-*Argrobacterium* Transformation

Transformation without the use of *Agrobacterium tumefaciens* circumvents the requirement for T-DNA sequences in the chosen transformation vector, and consequently vectors lacking these sequences can be utilized in addition to vectors such as the ones disclosed above that contain T-DNA sequences. Transformation techniques that do not rely on *Agrobacterium* include transformation via particle bombardment, protoplast uptake (e.g. polyethylene glycol (PEG) and electroporation), and microinjection. The choice of vector depends largely on the species being transformed. Below, the construction of typical vectors suitable for non-*Agrobacterium* transformation is disclosed.

IV.E.2.a. PCIB3064 pCIB3064 is a pUC-derived vector suitable for direct gene transfer techniques in combination with selection by the herbicide BASTA® (glufosinate ammonium or phosphinothricin). The plasmid pCIB246 comprises the CaMV 35S promoter in operational fusion to the *E. coli* β-glucuronidase (GUS) gene and the CaMV 35S transcriptional terminator and is disclosed in the PCT International Publication WO 93/07278. The 35S promoter of this vector contains two ATG sequences 5' of the start site. These sites are mutated using standard PCR techniques in such a way as to remove the ATGs and generate the restriction sites Ssp I and Pvu II. The new restriction sites are 96 and 37 bp away from the unique Sal I site and 101 and 42 bp away from the actual start site. The resultant derivative of pCIB246 is designated pCIB3025. The GUS gene is then excised from pCIB3025 by digestion with Sal I and Sac I, the termini rendered blunt and religated to generate plasmid pCIB3060. The plasmid pJIT82 is obtained from the John Innes Centre, Norwich, England, and the 400 bp Sma I fragment containing the bar gene from *Streptomyces* viridochromogenes is excised and inserted into the Hpa I site of pCIB3060 (Thompson et al., 1987). This generated pCIB3064, which comprises the bar gene under the control of the CaMV 35S promoter and terminator for herbicide selection, a gene for ampicillin resistance (for selection in *E. coli*) and a polylinker with the unique sites Sph I, Pst I, Hind III, and BamH I. This vector is suitable for the cloning of plant expression cassettes containing their own regulatory signals.

IV.E.2.b. DSOG19 and DSOG35 pSOG35 is a transformation vector that utilizes the *E. coli* dihydrofolate reductase (DHFR) gene as a selectable marker conferring resistance to methotrexate. PCR is used to amplify the 35S promoter (~800 bp), intron 6 from the maize Adh1 gene (~550 bp), and 18 bp of the GUS untranslated leader sequence from pSOG 10. A 250-bp fragment encoding the *E. coli* dihydrofolate reductase type II gene is also amplified by PCR and these two PCR fragments are assembled with a Sac I-Pst I fragment from pB1221 (BD Biosciences Clontech, Palo Alto, Calif., United States of America) that comprises the pUC19 vector backbone and the nopaline synthase terminator. Assembly of these fragments generates pSOG19 that contains the 35S promoter in fusion with the intron 6 sequence, the GUS leader, the DHFR gene, and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have Hind III, Sph I, Pst I, and EcoR I sites available for the cloning of foreign substances.

IV.E.3. Vector Suitable for Chloroplast Transformation

For expression of a nucleotide sequence of the presently disclosed subject matter in plant plastids, plastid transformation vector pPH143 (PCT International Publication WO 97/32011, example 36) is used. The nucleotide sequence is inserted into pPH143 thereby replacing the protoporphyrinogen oxidase (Protox) coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to Protox inhibitors.

IV.F. Transformation

Once a nucleotide sequence of the presently disclosed subject matter has been cloned into an expression system, it is transformed into a plant cell. The receptor and target expression cassettes of the presently disclosed subject matter can be introduced into the plant cell in a number of art-recognized ways. Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

IV.F.1. Transformation of Dicotyledons

Transformation techniques for dicotyledons are well known in the art and include *Agrobacterium*-based techniques and techniques that do not require *Agrobacterium*. Non-*Agrobacterium* techniques involve the uptake of heterologous genetic material directly by protoplasts or cells. This can be accomplished by PEG or electroporation-mediated uptake, particle bombardment-mediated delivery, or microinjection. Examples of these techniques are disclosed in Paszkowski et al., 1984; Potrykus et al., 1985; Reich et al., 1986; and Klein et al., 1987. In each case the transformed cells are regenerated to whole plants using standard techniques known in the art.

*Agrobacterium*-mediated transformation is a useful technique for transformation of dicotyledons because of its high efficiency of transformation and its broad utility with many different species. *Agrobacterium* transformation typically involves the transfer of the binary vector carrying the foreign DNA of interest (e.g. pCIB200 or pCIB2001) to an appropriate *Agrobacterium* strain which can depend on the complement of vir genes carried by the host *Agrobacterium* strain either on a co-resident Ti plasmid or chromosomally (e.g. strain CIB542 for pCIB200 and pCIB2001 (Uknes et al., 1993). The transfer of the recombinant binary vector to *Agrobacterium* is accomplished by a triparental mating procedure using *E. coli* carrying the recombinant binary vector, a helper *E. coli* strain that carries a plasmid such as pRK2013 and which is able to mobilize the recombinant binary vector to the target *Agrobacterium* strain. Alternatively, the recombinant binary vector can be transferred to *Agrobacterium* by DNA transformation (Höfgen & Willmitzer, 1988).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050; 5,036,006; and 5,100,792; all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium, or a bacteriophage, each containing DNA sought to be introduced) can also be propelled into plant cell tissue.

IV.F.2. Transformation of Monocotyledons

Transformation of most monocotyledon species has now also become routine. Exemplary techniques include direct gene transfer into protoplasts using PEG or electroporation, and particle bombardment into callus tissue. Transformations can be undertaken with a single DNA species or multiple DNA species (i.e. co-transformation), and both these techniques are suitable for use with the presently disclosed subject matter. Co-transformation can have the advantage of avoiding complete vector construction and of generating transgenic plants with unlinked loci for the gene of interest and the selectable marker, enabling the removal of the selectable marker in subsequent generations, should this be regarded as desirable. However, a disadvantage of the use of co-transformation is the less than 100% frequency with which separate DNA species are integrated into the genome (Schocher et al., 1986).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al., 1990 and Fromm et al., 1990 have published techniques for transformation of A188-derived maize line using particle bombardment. Furthermore, WO 93/07278 and Koziel et al., 1993 describe techniques for the transformation of elite inbred lines of maize by particle bombardment. This technique utilizes immature maize embryos of 1.5–2.5 mm length excised from a maize ear 14–15 days after pollination and a PDS-1000/He Biolistic particle delivery device (Bio-Rad Laboratories, Hercules, Calif., United States of America) for bombardment.

Transformation of rice can also be undertaken by direct gene transfer techniques utilizing protoplasts or particle bombardment. Protoplast-mediated transformation has been disclosed for Japonica-types and Indica-types (Zhang et al., 1988; Shimamoto et al., 1989; Datta et al., 1990) of rice. Both types are also routinely transformable using particle bombardment (Christou et al., 1991). Furthermore, WO 93/21335 describes techniques for the transformation of rice via electroporation. Casas et al., 1993 discloses the production of transgenic sorghum plants by microprojectile bombardment.

European Patent Application EP 0 332 581 describes techniques for the generation, transformation, and regeneration of *Pooideae* protoplasts. These techniques allow the transformation of *Dactylis* and wheat. Furthermore, wheat transformation has been disclosed in Vasil et al., 1992 using particle bombardment into cells of type C long-term regenerable callus, and also by Vasil et al., 1993 and Weeks et al., 1993 using particle bombardment of immature embryos and immature embryo-derived callus.

A representative technique for wheat transformation, however, involves the transformation of wheat by particle bombardment of immature embryos and includes either a high sucrose or a high maltose step prior to gene delivery. Prior to bombardment, embryos (0.75–1 mm in length) are plated onto MS medium with 3% sucrose (Murashige & Skoog, 1962) and 3 mg/l 2,4-dichlorophenoxyacetic acid (2,4-D) for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 hours and are then bombarded. Twenty embryos per target plate are typical, although not critical. An appropriate gene-carrying plasmid (such as pCIB3064 or pSG35) is precipitated onto micrometer size gold particles using standard procedures. Each plate of embryos is shot with biolistics device using a burst pressure of about 1000 pounds per square inch (psi) using a standard 80 mesh screen. After bombardment, the embryos are placed back into the dark to recover for about 24 hours (still on osmoticum). After 24 hours, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l BASTA® in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Transformation of monocotyledons using *Agrobacterium* has also been disclosed. See WO 94/00977 and U.S. Pat. No. 5,591,616, both of which are incorporated herein by reference. See also Negrotto et al., 2000, incorporated herein by reference. Zhao et al., 2000 specifically discloses transformation of sorghum with *Agrobacterium*. See also U.S. Pat. No. 6,369,298.

Rice (*Oryza sativa*) can be used for generating transgenic plants. Various rice cultivars can be used (Hiei et al., 1994; Dong et al., 1996; Hiei et al., 1997). Also, the various media constituents disclosed below can be either varied in quantity or substituted. Embryogenic responses are initiated and/or cultures are established from mature embryos by culturing on MS-CIM medium (MS basal salts, 4.3 g/liter; B5 vitamins (200×), 5 ml/liter; sucrose, 30 g/liter; proline, 500 mg/liter; glutamine, 500 mg/liter; casein hydrolysate, 300 mg/liter; 2,4-D (1 mg/ml), 2 ml/liter; pH adjusted to 5.8 with 1 N KOH; Phytagel, 3 g/liter). Either mature embryos at the initial stages of culture response or established culture lines are inoculated and co-cultivated with the *Agrobacterium tumefaciens* strain LBA4404 (*Agrobacterium*) containing the desired vector construction. *Agrobacterium* is cultured from glycerol stocks on solid YPC medium (plus 100 mg/L spectinomycin and any other appropriate antibiotic) for about 2 days at 28° C. *Agrobacterium* is re-suspended in liquid MS-CIM medium. The *Agrobacterium* culture is diluted to an $OD_{600}$ of 0.2–0.3 and acetosyringone is added to a final concentration of 200 µM. Acetosyringone is added before mixing the solution with the rice cultures to induce *Agrobacterium* for DNA transfer to the plant cells. For inoculation, the plant cultures are immersed in the bacterial suspension. The liquid bacterial suspension is removed and the inoculated cultures are placed on co-cultivation medium and incubated at 22° C. for two days. The cultures are then transferred to MS-CIM medium with ticarcillin (400 mg/liter) to inhibit the growth of *Agrobacterium*. For constructs utilizing the PMI selectable marker gene (Reed et al., 2001), cultures are transferred to selection medium containing mannose as a carbohydrate source (MS with 2% mannose, 300 mg/liter ticarcillin) after 7 days, and cultured for 3–4 weeks in the dark. Resistant colonies are then transferred to regeneration induction medium (MS with no 2,4-D, 0.5 mg/liter IAA, 1 mg/liter zeatin, 200 mg/liter TIMENTIN®, 2% mannose, and 3% sorbitol) and grown in the dark for 14 days. Proliferating colonies are then transferred to another round of regeneration induction media and moved to the light growth room. Regenerated shoots are transferred to GA7 containers with GA7-1 medium (MS with no hormones and 2% sorbitol) for 2 weeks and then moved to the greenhouse when they are large enough and have adequate roots. Plants are transplanted to soil in the greenhouse ($T_0$ generation) grown to maturity and the $T_1$ seed is harvested.

IV.F.3. Transformation of Plastids

Seeds of *Nicotiana tabacum* c.v. 'Xanthi nc' are germinated seven per plate in a 1" circular array on T agar medium and bombarded 12–14 days after sowing with 1 µm tungsten particles (M10, Bio-Rad Laboratories, Hercules, Calif., United States of America) coated with DNA from plasmids pPH143 and pPH145 essentially as disclosed (Svab & Maliga, 1993). Bombarded seedlings are incubated on T medium for two days after which leaves are excised and placed abaxial side up in bright light (350–500 µmmol photons/m²/s) on plates of RMOP medium (Svab et al., 1990) containing 500 µg/ml spectinomycin dihydrochloride (Sigma, St. Louis, Mo., United States of America). Resistant shoots appearing underneath the bleached leaves three to eight weeks after bombardment are subcloned onto the same selective medium, allowed to form callus, and secondary shoots isolated and subcloned.

Complete segregation of transformed plastid genome copies (homoplasmicity) in independent subclones is assessed by standard techniques of Southern blotting (Sambrook & Russell, 2001). BamH I/EcoR I-digested total cellular DNA (Mettler, 1987) is separated on 1% Tris-borate-EDTA (TBE) agarose gels, transferred to nylon membranes (Amersham Biosciences, Piscataway, N.J., United States of America) and probed with $^{32}$P-labeled random primed DNA sequences corresponding to a 0.7 kb BamH I/Hind III DNA fragment from pC8 containing a portion of the rps7/12 plastid targeting sequence. Homoplasmic shoots are rooted aseptically on spectinomycin-containing MS/IBA medium (McBride et al., 1994) and transferred to the greenhouse.

V. Plants, Breeding, and Seed Production

V.A. Plants

The presently disclosed subject matter also provides plants comprising the disclosed compositions. In some embodiments, the modification includes being enriched for an essential amino acid as a proportion of a polypeptide fraction of the plant. In some embodiments, the polypeptide fraction can be, for example, total seed polypeptide, soluble polypeptide, insoluble polypeptide, water-extractable polypeptide, and lipid-associated polypeptide. In some embodiments, the modification includes overexpression, underexpression, antisense modulation, sense suppression, inducible expression, inducible repression, or inducible modulation of a gene.

V.B. Breeding

The plants obtained via transformation with a nucleotide sequence of the presently disclosed subject matter can be any of a wide variety of plant species, including monocots and dicots; however, the plants used in the method for the presently disclosed subject matter are selected in some embodiments from the list of agronomically important target crops set forth hereinabove. The expression of a gene of the presently disclosed subject matter in combination with other characteristics important for production and quality can be incorporated into plant lines through breeding. Breeding approaches and techniques are known in the art. See e.g., Welsh, 1981; Wood, 1983; Mayo, 1987; Singh, 1986; Wricke & Weber, 1986.

The genetic properties engineered into the transgenic seeds and plants disclosed above are passed on by sexual reproduction or vegetative growth and can thus be maintained and propagated in progeny plants. Generally, the maintenance and propagation make use of known agricultural methods developed to fit specific purposes such as tilling, sowing, or harvesting. Specialized processes such as hydroponics or greenhouse technologies can also be applied. As the growing crop is vulnerable to attack and damage caused by insects or infections as well as to competition by weed plants, measures are undertaken to control weeds, plant diseases, insects, nematodes, and other adverse conditions to improve yield. These include mechanical measures such as tillage of the soil or removal of weeds and infected plants, as well as the application of agrochemicals such as herbicides, fungicides, gametocides, nematicides, growth regulants, ripening agents, and insecticides.

Depending on the desired properties, different breeding measures are taken. The relevant techniques are well known in the art and include, but are not limited to, hybridization, inbreeding, backcross breeding, multiline breeding, variety blend, interspecific hybridization, aneuploid techniques, etc. Hybridization techniques can also include the sterilization of plants to yield male or female sterile plants by mechanical, chemical, or biochemical means. Cross-pollination of a male sterile plant with pollen of a different line assures that the genome of the male sterile but female fertile plant will uniformly obtain properties of both parental lines. Thus, the transgenic seeds and plants according to the presently disclosed subject matter can be used for the breeding of improved plant lines that, for example, increase the effectiveness of conventional methods such as herbicide or pesticide treatment or allow one to dispense with said methods due to their modified genetic properties. Alternatively new crops with improved stress tolerance can be obtained, which, due to their optimized genetic "equipment", yield harvested product of better quality than products that were not able to tolerate comparable adverse developmental conditions (for example, drought).

V.C. Seed Production

Some embodiments of the presently disclosed subject matter also provide seed and isolated product from plants that comprise an expression cassette comprising a promoter sequence operably linked to an isolated nucleic acid, the nucleotide sequence being selected from the group consisting of:
  (a) a nucleotide sequence that hybridizes under highly stringent conditions of hybridization of 65° C. in 6×SSC, followed by a final washing step of at least 15 minutes at 65° C. in 0.1×SSC to a nucleotide sequence as set forth in SEQ ID NO: 1, or fragment, domain, or feature thereof;
  (b) a nucleotide sequence encoding a polypeptide that is an ortholog of a polypeptide of SEQ ID NO: 2, or a fragment, domain or feature thereof;
  (c) a nucleotide sequence complementary (for example, fully complementary) to (a) or (b); and
  (d) a nucleotide sequence that is the reverse complement (for example, its full reverse complement) of (a) or (b) according to the present disclosure.

In some embodiments the isolated product comprises an enzyme, a nutritional polypeptide, a structural polypeptide, an amino acid, a lipid, a fatty acid, a polysaccharide, a sugar, an alcohol, an alkaloid, a carotenoid, a propanoid, a steroid, a pigment, a vitamin, or a plant hormone.

Embodiments of the presently disclosed subject matter also relate to isolated products produced by expression of an isolated nucleic acid containing a nucleotide sequence selected from the group consisting of:
  (a) a nucleotide sequence that hybridizes under highly stringent conditions of hybridization of 65° C. in 6×SSC, followed by a final washing step of at least 15 minutes at 65° C. in 0.1×SSC to a nucleotide sequence as set forth in SEQ ID NO: 1, or a fragment, domain, or feature thereof;
  (b) a nucleotide sequence encoding a polypeptide that is an ortholog of a polypeptide listed in SEQ ID NO: 2, or a fragment, domain, or feature thereof;
  (c) a nucleotide sequence complementary (for example, fully complementary) to (a) or (b); and
  (d) a nucleotide sequence that is the reverse complement (for example, its full reverse complement) of (a) or (b) according to the present disclosure.

In some embodiments, the product is produced in a plant. In some embodiments, the product is produced in cell culture. In some embodiments, the product is produced in a cell-free system. In some embodiments, the product comprises an enzyme, a nutritional polypeptide, a structural polypeptide, an amino acid, a lipid, a fatty acid, a polysaccharide, a sugar, an alcohol, an alkaloid, a carotenoid, a propanoid, a steroid, a pigment, a vitamin, or a plant hormone. In some embodiments, the product is a polypeptide comprising an amino acid sequence listed in SEQ ID NO: 2, or ortholog thereof. In some embodiments, the polypeptide comprises an enzyme.

In seed production, germination quality, and uniformity of seeds are essential product characteristics. As it is difficult to keep a crop free from other crop and weed seeds, to control seedborne diseases, and to produce seed with good germination, fairly extensive and well-defined seed production practices have been developed by seed producers who are experienced in the art of growing, conditioning, and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides, or mixtures thereof. Customarily used protectant coatings comprise compounds such as captan, carboxin, thiram (tetramethylthiuram disulfide; TMTD®; available from R. T. Vanderbilt Company, Inc., Norwalk, Conn., United States of America), methalaxyl (APRON XL®; available from Syngenta Corp., Wilmington, Del., United States of America), and pirimiphos-methyl (ACTELLIC®; available from Agriliance, LLC, St. Paul, Minn., United States of America). If desired, these compounds are formulated together with further carriers, surfactants, and/or application-promoting adjuvants customarily employed in the art of formulation to provide protection against damage caused by bacterial, fungal, or animal pests. The protectant coatings can be applied by impregnating propagation material with a liquid formulation or by coating with a combined wet or dry formulation. Other methods of application are also possible such as treatment directed at the buds or the fruit.

VI. Additional Applications

The presently disclosed subject matter also provides methods for targeting a protein of interest to a structure of a plant cell. In some embodiments, the structure is selected from the group including but not limited to endoplasmic reticulum (ER) and apoplast. In some embodiments, the method comprises (a) fusing a nucleic acid molecule encoding a signal sequence of a *Zea mays* Q protein in frame to a nucleotide sequence encoding the protein of interest, wherein the nucleic acid molecule encoding a signal sequence of a *Zea mays* Q protein and the nucleotide sequence encoding the protein of interest are operably linked to a promoter to produce a plant expression construct; and (b) transforming the plant cell with the plant expression construct, whereby the protein of interest is targeted to the structure. In some embodiments, the signal sequence corresponds to the first 19 amino acid of SEQ ID NO: 2.

As used herein, the term "protein of interest" refers to any polypeptide or polypeptide fragment for which the expression in a plant or plant cell would be desirable. Exemplary proteins of interest include, but are not limited to carbohydrases, cellulases, hemicellulases, pectinases, isomerases, lyases, proteases, heat shock proteins, chaperonins, phytases, insecticidal proteins, antimicrobial proteins, α-amylases, glucoamylases, glucanases, glucosidases, xylanases, ferulic acid esterases, galactosidases, pectinases, and chymosins. In some embodiments, the protein of interest is naturally occurring in the plant cell, but one or more extra copies of a nucleic acid sequence encoding the polypeptide of interest is provided as a transgene. In some embodiments, the protein of interest is heterologous to the plant or plant cell.

The presently disclosed subject matter also provides methods for producing a plant seed with an increased nutritional value. In some embodiments, the method comprises (a) transforming a plant cell with an expression vector comprising a nucleotide sequence encoding SEQ ID NO: 2, or a fragment or derivative thereof; (b) regenerating a plant from the transformed plant cell; and (c) isolating a seed from the regenerated plant, whereby a seed with an increased nutritional value is produced.

As used herein, the phrase "a seed with increased nutritional value" refers to a seed that has been modified such to contain a polypeptide that is not normally found in the seed or contains an elevated amount of a polypeptide that is normally found in the seed. In some embodiments, the polypeptide that is not normally found in the seed is a derivative of a protein that the seed normally contains. Such a derivative can be characterized, for example, by a modification of the amino acid sequence of a naturally occurring protein to include a higher content of one or more amino acids (for example, an increased proportion of one or more essential amino acids), an improved amino acid balance, and/or an improved amino acid digestibility when compared to a seed from a non-transformed plant of the same species. These modifications of the amino acid sequence can be accomplished by mutagenesis of a nucleotide sequence encoding the polypeptide using techniques that are known to the skilled artisan.

The presently disclosed subject matter also provides methods for targeting a protein of interest to a protein body in a plant. In some embodiments, the method comprises (a) fusing a nucleic acid molecule encoding SEQ ID NO: 2, or a fragment or derivative thereof, in frame to a nucleotide sequence encoding the protein of interest, wherein the nucleic acid molecule encoding SEQ ID NO: 2, or the fragment or derivative thereof, and the nucleotide sequence encoding the protein of interest are operably linked to a promoter to produce a plant expression construct; and (b) transforming the plant cell with the plant expression construct, whereby the protein of interest is targeted to a protein body in the plant. In some embodiments, the nucleic acid molecule encoding SEQ ID NO: 2, or a fragment or derivative thereof, which is fused in frame to a nucleotide sequence encoding the protein of interest includes a nucleotide sequence encoding a protease cleavage site between the nucleic acid molecule encoding SEQ ID NO: 2, or a fragment or derivative thereof, and the nucleotide sequence encoding the protein of interest.

Proteases for which a cleavage site can be introduced in the fusion protein, and the amino acid sequences of recognized cleavage sites, are known in the arts of molecular biology and protein expression, and include, but are not limited to Factor Xa, thrombin, the family of caspases, chymotrypsin, pepsin, tobacco etch virus protease, and trypsin. See Sambrook & Russell, 2001, and references cited therein, for a discussion of the use of proteases to cleave fusion proteins. The protease can be chosen based upon its recognition sequence, for example, based on the absence of the recognition sequence in the protein of interest, such that when the fusion protein is treated with the protease, the protein of interest will be released from the Q protein (or fragment or derivative thereof) intact. Additional purification steps that are known to the skilled artisan can then be used to purify the protein of interest. These techniques include affinity purification (if an antibody to the protein of interest is available), SDS-PAGE separation, size based chromatography, or any other method available to the skilled artisan.

EXAMPLES

The following Examples have been included to illustrate representative and exemplary modes of the presently disclosed subject matter. In light of the present disclosure and the general level of skill in the art, those of skill will appreciate that the following Examples are intended to be exemplary only and that numerous changes, modifications, and alterations can be employed without departing from the spirit and scope of the presently disclosed subject matter.

Standard recombinant DNA and molecular cloning techniques used here are well known in the art and are disclosed in Sambrook & Russell, 2001; Silhavy et al., 1984; Ausubel et al., 2002; Ausubel et al., 2003; Reiter et al., 1992; and Schultz et al., 1998.

Example 1

Isolation of Promoter/Genomic Clones Corresponding to the Q Protein Gene

The nucleotide sequence from the Q protein ORF (SEQ ID NO: 1) was used to design primers for genomic walking. A genomic clone corresponding to the Q protein cDNA was isolated via PCR utilizing maize libraries based on the GENOME WALKER™ kit (BD Biosciences Clontech, Palo Alto, Calif., United States of America) as template. GENOME WALKER™ adaptor-ligated maize genomic libraries were constructed using DNA from maize cultivar 6N615. Five different libraries were constructed, each comprising genomic DNA fragments generated by digestion with one of the following blunt end restriction enzymes: Dra I, EcoR V, Hinc II, Ssp I, or Stu I. GENOME WALKER™ libraries were screened utilizing one or more of the gene specific primers QP1 (SEQ ID NO: 4) and QP2 (SEQ ID NO: 5) with the adaptor primer supplied in the kit. PCR conditions were those suggested in BD Bioscience Clontech's user's manual. PCR products were fractionated on agarose gels, and the resulting product band was excised, subcloned into a TOPO® vector (Invitrogen Corp., Carlsbad, Calif., United States of America) and sequenced to verify the correct product. A 516 base pair genomic clone corresponding to the Q protein gene was cloned from the Dra I GENOME WALKER™ library.

Example 2

Activity of the Q Promoter

Transgenic maize plants were stably transformed with binary vector 11037 using *Agrobacterium*-mediated transformation. Vector 11037 is identical to pNOV4061 (SEQ ID NO: 14: see also PCT International Patent Application Publication WO 03/57248) with the exception that the γ-zein promoter found in the phytase expression cassette in pNOV4061 is replaced with the Q promoter (SEQ ID NO: 6) in vector 11037. The gene product of the phytase expression cassette in vector 11037 is presented in SEQ ID NO: 12, and is identical to SEQ ID NO: 6 of PCT International Patent Application Publication WO 03/57248. It includes the 19 amino acid signal sequence from the 27 kDa γ-zein (corresponds to the first 19 amino acids of SEQ ID NO: 12), Nov9x phytase, and the hexapeptide SEKDEL (SEQ ID NO: 11).

T1 seed were harvested from plants regenerated from maize tissue transformed with vector 11037. Seed were pulverized and soluble proteins were extracted from flour samples using extraction buffer (50 mM Tris-HCl, pH 8.0, 100 mM NaCl, 2 mM EDTA). Flour suspensions were incubated at room temperature for 60 minutes with agitation, and insoluble material was removed by centrifugation.

The measurement of phytase activity and detection of Nov9x phytase by Western blot analysis was performed as described in Example 3 of PCT WO 03/57248. All reagents and reaction conditions were as described in WO 03/57248, and all reagent volumes were adjusted proportionally. Briefly, the measurement of phytase activity is based on the detection of inorganic phosphate released from sodium phytate substrate by the hydrolytic action of phytase. Phytase assay procedures were adapted from the protocols of Wyss et al., 1999 and Engelen et al., 2001.

Phytase activity in flour samples from single kernels and pooled kernels was measured at pH 5.5 and 37° C. Assay results for eight samples of T1 seed harvested from two regenerated transgenic plants (plants A and B) are presented in Table 1. Sample 305B-11A represents the phytase activity extracted from a control corn flour sample containing Nov9x phytase. The samples were listed in order of decreasing phytase activity.

TABLE 1

Demonstration of Phytase Activity in Transgenic Corn Flour

| Sample[a] | Phytase Units per Gram of Corn Flour |
|---|---|
| 305B-11A (positive control) | 1775 |
| Plant A, seed #3 | 451 |
| Plant A, seed 10 | 392 |
| Plant B, seed 5 | 314 |
| Plant A, seed 4 | 292 |
| Plant B (pooled seed) | 291 |
| Plant B, seed 4 | 255 |
| Plant B, seed 7 | 204 |
| Plant A, seed 5 | 191 |

[a]Each sample was from a numbered, single seed, with the exception of the sample designated as a pooled seed, which corresponds to 10 T1 kernels pulverized together.

Flour extracts analyzed in Table 1 were also analyzed by Western blot analysis using antisera to purified Nov9x phytase as shown in FIG. 1. The first lane on the blot depicted in FIG. 1 indicates the positions of molecular weight standards (labeled on left). A188 is an extract of seed from non-transgenic corn. Nov9x phytase is identified as the prominent band migrating in the region of the 55 kDa standard. Nov9x phytase was not detected in the A188 corn flour extract.

Example 3

SDS-PAGE Analysis of Proteins Extracted from Seeds

Figure 2:
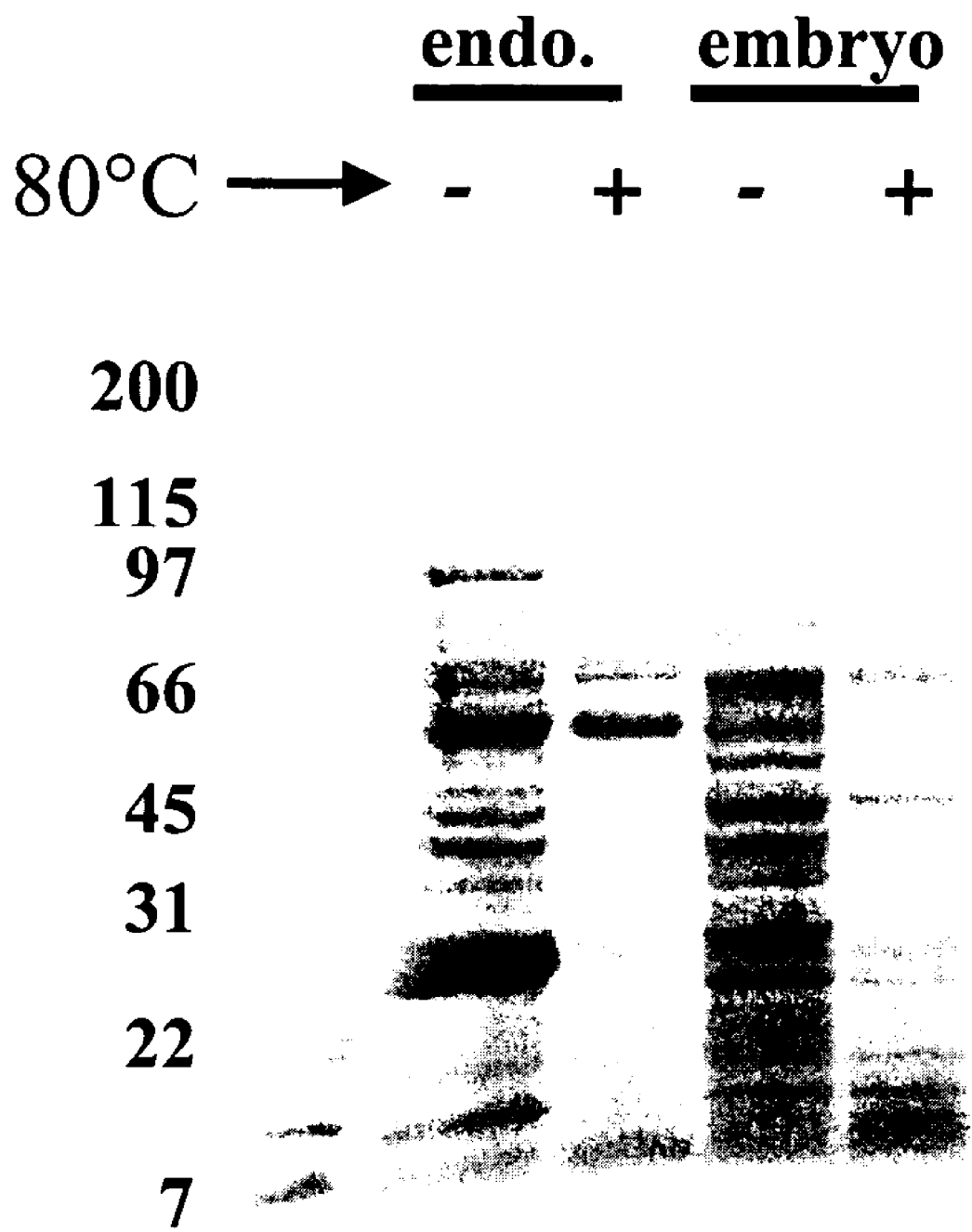
FIG. 2 depicts SDS-PAGE analysis of proteins extracted from endosperm flour (endo.) or from embryo paste (embryo) from non-transgenic corn. Samples were run before (−) and after (+) heating the extract to 80° C. for 20 minutes.

Dried kernels from Hi-II x A188 maize were soaked in distilled water at 4° C. overnight. Endosperm and embryos were separated and frozen at −80° C. Frozen tissue was pulverized using a KLECO tissue pulverizer (KLECO, Visalia, Calif., United States of America). Proteins were extracted from endosperm flour by addition of 500 μl extraction buffer (50 mM HEPES, pH 8, 2 mM EDTA, 100 mM NaCl, and 4 mM DTT) for every 100 mg flour. Samples were vortexed and rocked at room temperature for 40 minutes. Proteins were extracted from the embryo paste by addition of 2.5 ml extraction buffer for every 100 mg tissue. A portion of the soluble fraction was heated at 80° C. for 20 minutes, and aggregated proteins were removed by centrifugation. Samples of the extract before (−) and after (+) heating were analyzed by SDS-PAGE (see FIG. 2).

Discussion of Examples 1–3

A 55 kDa Protein is the second most abundant Protein released from endosperm flour in buffer and DTT. In the course of testing different conditions for extracting a recombinant thermostable enzyme from maize flour, an abundant endosperm protein of 55 kDa was identified that remained soluble during heating at 80° C. (Example 3, FIG. 2). The 55 kDa protein was the second most abundant protein released from endosperm flour in buffer containing 100 mM NaCl and 4 mM DTT. The most abundant protein in these extracts was the 27 kDa γ-zein, a maize prolamin that typically constitutes 15% of total endosperm protein.

A similar endosperm fraction was described by Vitale et al., 1982. They incubated protein bodies in the presence of DTT or β-ME and characterized proteins in the soluble fraction. The two most abundant proteins released from protein bodies under these conditions had molecular weights of 28,000 and 58,000. Proteins in this fraction were named "Reduced Soluble Proteins" or RSPs.

An EST in GENBANK® matches the first 20 codons of the 55 kDa protein and encodes a Polypeptide chain of 171 residues. The amino acid sequences at the amino-termini of the 27 kDa and 55 kDa proteins discussed above were determined. The partial sequence of the 27 kDa protein was THTSGGXXXQPPPPVHLLPP (SEQ ID NO: 7). This sequence matches the amino-terminus of the 28 kDa maize glutelin-2 (γ-zein; Prat et al., 1985; Boronat et al., 1986).

The partial sequence of the 55 kDa protein was TQTG-GCSCGQQQSHEQQHHP (SEQ ID NO: 8). A search of the PIR and SwissProt databases did not identify any matches to this sequence. However, when a back-translated DNA sequence was used to screen GENBANK®, the query sequence matched at each codon with an expressed sequence tag (EST) from an endosperm cDNA library (GENBANK® Accession No. A1812147). Translation of the EST sequence starting with the codon that corresponds to the amino-terminus of the 55 kDa protein yields a deduced polypeptide chain of 171 residues.

Cloning of two overlapping cDNAs that encode a protein of 289 residues (molecular weight 34,000). Oligonucleotide primers against the EST sequence were used to amplify a cDNA clone from a maize cDNA library. The predicted stop codon in the EST sequence was found to encode a Leu in the new clone, and the ORF continued to the end of the cloned sequence. A second cDNA clone that overlapped with the 3' end of the first was amplified from the same library. The new ORF encoded an additional 118 amino acids, for a total of 289. The calculated molecular weight of the deduced protein is 34,000. The discrepancy between the calculated molecular weight (34,000) and that estimated from SDS-PAGE analysis (55,000) could be due to unusual structural features related to the abundance of Gln residues. The amino acid composition of the deduced protein is shown in Table 2.

TABLE 2

Amino Acid Composition of Zeins

| Amino Acid | zein-α19 | zein-α22 | zein-β15 | zein-δ10 | zein-δ18 | zein-γ27 | SEQ ID NO: 2 |
|---|---|---|---|---|---|---|---|
| A | 29 | 34 | 23 | 7 | 9 | 10 | 6 |
| C | 2 | 1 | 7 | 5 | 3 | 15 | 16 |
| D | 0 | 0 | 1 | 1 | 0 | 0 | 3 |
| E | 1 | 2 | 3 | 0 | 0 | 2 | 13 |
| F | 13 | 8 | 0 | 5 | 5 | 2 | 3 |
| G | 5 | 2 | 14 | 4 | 5 | 13 | 11 |
| H | 2 | 3 | 0 | 3 | 3 | 16 | 29 |
| I | 9 | 11 | 1 | 3 | 8 | 4 | 8 |
| K | 0 | 0 | 0 | 0 | 1 | 0 | 5 |
| L | 43 | 42 | 16 | 15 | 13 | 19 | 11 |
| M | 0 | 5 | 18 | 29 | 53 | 1 | 4 |
| N | 10 | 13 | 3 | 3 | 3 | 0 | 8 |
| P | 23 | 22 | 14 | 20 | 35 | 51 | 16 |
| Q | 41 | 51 | 26 | 15 | 15 | 30 | 104 |
| R | 2 | 4 | 5 | 0 | 0 | 5 | 4 |
| S | 15 | 17 | 8 | 8 | 18 | 8 | 23 |
| T | 5 | 7 | 5 | 5 | 10 | 9 | 6 |
| V | 5 | 17 | 3 | 5 | 5 | 15 | 9 |
| W | 0 | 0 | 0 | 0 | 2 | 0 | 0 |
| Y | 8 | 7 | 14 | 1 | 2 | 4 | 10 |
| Total | 213 | 246 | 161 | 129 | 190 | 204 | 289 |

The amino acid sequence at the C-terminus shows homology to prolamins, the seed storage proteins of cereals. The amino acid sequence from residues 172–289 of the mature protein shows homology to prolamins of several cereals including maize, rice, and barley. Sequence identities range from 36–53% for stretches of 58–118 residues: 37% (44/116 residues) for a rice prolamin, 38% (46/118) for a maize zein, 36% (40/115) for the sorghum prolamin γ-kafirin, 53% (31/58) for oat avenin, and 55% (33/59) for barley B-hordein. Identity with 27 kDa γ-zein (glutelin-2) was 38% over a stretch of 119 residues (46 matches). The homologous region was limited to the C-terminal domain of γ-zein.

The amino acid compositions of the major zeins are included in Table 2 for comparison with the 55 kDa protein. The deduced sequence is remarkable by comparison to the other zeins with respect to relative levels of three amino acids: the deduced sequence contains 106 Gln, 13 Glu, and 5 Lys out of 289 total residues. All other zeins have 0 Lys, except for the 18 kDa 67-zein, which has just 1.

The percent composition of each amino acid in the deduced protein and other zeins is shown in Table 3. The 55 kDa protein contains 36% Gln. By comparison, the α-zeins are the next most Gln-rich prolamins and contain only 20% Gln. The 55 kDa protein also has the lowest Pro content of maize prolamins. The amino acid composition of the 58 kDa RSP characterized by Vitale et al., 1982 is displayed side-by-side with that for the 55 kDa protein.

TABLE 3

Percent Composition of Amino Acids in Zeins

| Amino Acid | zein-α19 | zein-α22 | zein-β15 | zein-δ10 | zein-δ18 | zein-γ27 | SEQ ID NO: 2 | 58 kD RSP |
|---|---|---|---|---|---|---|---|---|
| G | 2.3 | 0.8 | 8.7 | 3.1 | 2.6 | 6.4 | 3.8 | 4.9 |
| A | 13.6 | 13.8 | 14.3 | 5.4 | 4.7 | 4.9 | 2.1 | 3.5 |
| V | 2.3 | 6.9 | 1.9 | 3.9 | 2.6 | 7.4 | 3.1 | 5.1 |
| L | 20.2 | 17.1 | 9.9 | 11.6 | 6.8 | 9.3 | 3.8 | 4.7 |
| I | 4.2 | 4.5 | 0.6 | 2.3 | 4.2 | 2.0 | 2.8 | 2.2 |
| M | 0.0 | 2.0 | 11.2 | 22.5 | 17.9 | 0.5 | 1.4 | 1.3 |
| F | 6.1 | 3.3 | 0.0 | 3.9 | 2.6 | 1.0 | 1.0 | 1.9 |
| W | 0.0 | 0.0 | 0.0 | 0.0 | 1.1 | 0.0 | 0.0 | 0.0 |
| K | 0.0 | 0.0 | 0.0 | 0.0 | 0.5 | 0.0 | 1.7 | 2.6 |
| P | 10.8 | 8.9 | 8.7 | 15.5 | 18.4 | 25.0 | 5.5 | 4.7 |
| C | 0.9 | 0.4 | 4.3 | 3.9 | 1.6 | 7.4 | 5.5 | 4.4 |
| S | 7.0 | 6.9 | 5.0 | 6.2 | 9.5 | 3.9 | 8.0 | 7.3 |
| T | 2.3 | 2.8 | 3.1 | 3.9 | 5.3 | 4.4 | 2.1 | 2.5 |
| Y | 3.8 | 2.8 | 8.7 | 0.8 | 1.1 | 2.0 | 3.5 | 3.5 |
| N | 4.7 | 5.3 | 1.9 | 2.3 | 1.6 | 0.0 | 2.8 | 4.3 |
| D | 0.0 | 0.0 | 0.6 | 0.8 | 0.0 | 0.0 | 1.0 | |
| Q | 19.2 | 20.7 | 16.1 | 11.6 | 7.9 | 14.7 | 36.0 | 33.6 |
| E | 0.5 | 0.8 | 1.9 | 0.0 | 0.0 | 1.0 | 4.5 | |
| H | 0.9 | 1.2 | 0.0 | 2.3 | 1.6 | 7.8 | 10.0 | 11.0 |
| R | 0.9 | 1.6 | 3.1 | 0.0 | 0.0 | 2.5 | 1.4 | 2.1 |
| SUM | 100.0 | 100.0 | 100.0 | 100.0 | 100.0 | 100.0 | 100.0 | 99.6 |

Example 4

Accumulation of a Q Protein Fusion Protein in Transgenic Seed

Construct 11045 was a binary vector encoding a fusion protein of the full-length Q protein linked to an α-galactosidase enzyme from *T. maritima* with a tripeptide linker Gly-Gly-Ala. The gene encoding the fusion protein was operably linked to the promoter of the 27 kDa gamma-zein protein (SEQ ID NO: 13). Primers were designed to isolate a nucleotide sequence encoding the Q-protein from pNOV4349 (SEQ ID NO: 17, of which nucleotides 10061–10090 correspond to the Q-protein coding sequence) while adding a 9 bp sequence encoding the tripeptide linker to the 3' end. 3' Nco I, and 5' BamH I sites were added to the ends of the PCR product. The 953 bp PCR fragment was amplified from pNOV4349 and cut with BamH I and Nco I, then inserted into the 5227 bp BamH I/Nco I fragment from pNOV4325 (SEQ ID NO: 16; nucleotides 3565–5901 encode the α-galactosidase polypeptide). This plasmid was named pWIN010. Construct pWIN010 was then cut with Kpn I and Hind III, and the 3489 bp fragment was ligated to the 9154 bp Kpn I/Hind III fragment from binary vector pNOV2117 (SEQ ID NO: 15; see also PCT International Patent Application Publication WO 03/57248).

Transgenic maize plants were stably transformed with binary vector 11045 using *Agrobacterium*-mediated transformation. T1 seed were harvested from plants regenerated from maize tissue transformed with vector 11045. Seeds were pulverized and soluble proteins were extracted from flour samples using extraction buffer (50 mM Tris-HCl, pH 8.0, 100 mM NaCl, 2 mM EDTA). Flour suspensions were incubated at room temperature for 60 minutes with agitation, and insoluble material was removed by centrifugation. The corn flour samples were then analyzed for α-galactosidase activity. α-galactosidase activity results are presented in Table 4.

TABLE 4

α-galactosidase Activity in Trangenic Maize

| Sample ID | Construct | α-galactosidase units per g of flour |
|---|---|---|
| MD9L011883 | 11045 | 4.06 |
| MD9L011893 | 11045 | 9.31 |
| MD9L011901 | 11045 | 8.39 |
| MD9L011903 | 11045 | 9.28 |
| MD9L011912 | 11045 | 7.79 |
| Negative Corn Flour | (none) | −0.78 |

The measurement of α-galactosidase activity was based on the colorimetric assay involving the release of p-nitrophenol from p-nitrophenyl α-d-galactopyranoside as described in Liebl et al., 1998.

Figure 3:
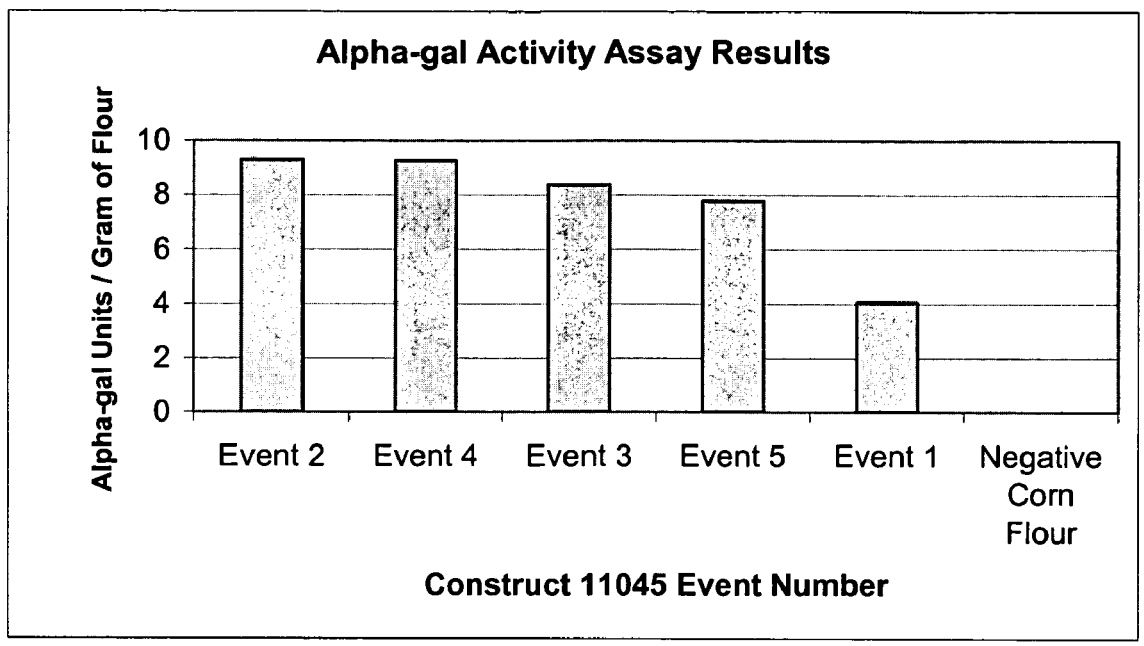
FIG. 3 is a bar graph depicting the results of assaying α-galactosidase activity in flour from transgenic corn seeds that contain a fusion protein including the Q protein amino acid sequence fused to α-galactosidase. Activity is expressed as α-galactosidase units per gram of flour from individual seeds.

As shown in Table 4, the α-galactosidase activity of transgenic maize containing construct 11045 encoding the Q-protein/α-galactosidase fusion protein showed an increase in α-galactosidase activity above the negative corn flour control. The levels ranged from 4 α-galactosidase units/gram offlourto 9 α-galactosidase units/gram of flour. The negative corn flour control has no α-galactosidase activity. These results are also presented in FIG. 3.

Example 5

The Q Protein Signal Sequence Directs Accumulation of a Fusion Protein to Transgenic Seed Binary vector 12173 was made by designing primers to isolate the Q protein signal sequence (amino acids 1–19 of SEQ ID NO: 2) from pNOV4349 while adding a 3' Nco I and a 5' BamH I site to the ends of the PCR product. The 80 bp PCR fragment was amplified from pNOV4349 and cut with BamH I and Nco I, then inserted into the 5226 bp BamH I/Nco I fragment from pNOV4328 (SEQ ID NO: 18; nucleotides 3621–5279 encode the α-galactosidase polypeptide). This plasmid was named pWIN013New. pWIN013New was then cut with Kpn I and Hind III, and the 2614 bp fragment was ligated to the 9154 bp Kpn I/Hind III fragment from binary vector pNOV2117 (SEQ ID NO: 15; see also PCT International Patent Application Publication WO 03/57248). This construct was named binary vector 12173. It encodes a fusion protein containing the 19 amino acid signal sequence from the Q protein (corresponds to the first 19 amino acid of SEQ ID NO: 2) fused to the α-galactosidase protein under the transcriptional control of a maize 27 kDa gamma zein promoter (SEQ ID NO: 13).

Transgenic maize plants were stably transformed with binary vector 12173 using *Agrobacterium*-mediated transformation. T1 seed were harvested from plants regenerated from maize tissue transformed with binary vector 12173. Seed were pulverized and soluble proteins were extracted from flour samples using extraction buffer (50 mM Tris-HCl, pH 8.0, 100 mM NaCl, 2 mM EDTA). Flour suspensions were incubated at room temperature for 60 minutes with agitation, and insoluble material was removed by centrifugation. The corn flour samples were then analyzed for α-galactosidase activity. α-galactosidase activity results are presented in Table 5.

TABLE 5

α-galactosidase Activity in Trangenic Maize

| Sample ID | Construct | α-galactosidase units per g flour |
|---|---|---|
| MD9L020749 | 12173 | 70.848 |
| MD9L020735 | 12173 | 68.175 |
| MD9L030752 | 12173 | 52.274 |
| MD9L020758 | 12173 | 43.160 |
| MD9L019976 | 12173 | 23.976 |
| MD9L019782 | 12173 | 11.877 |
| MD9L019766 | 12173 | 2.566 |
| Negative Corn Flour | N/A | −0.782 |

Figure 4:
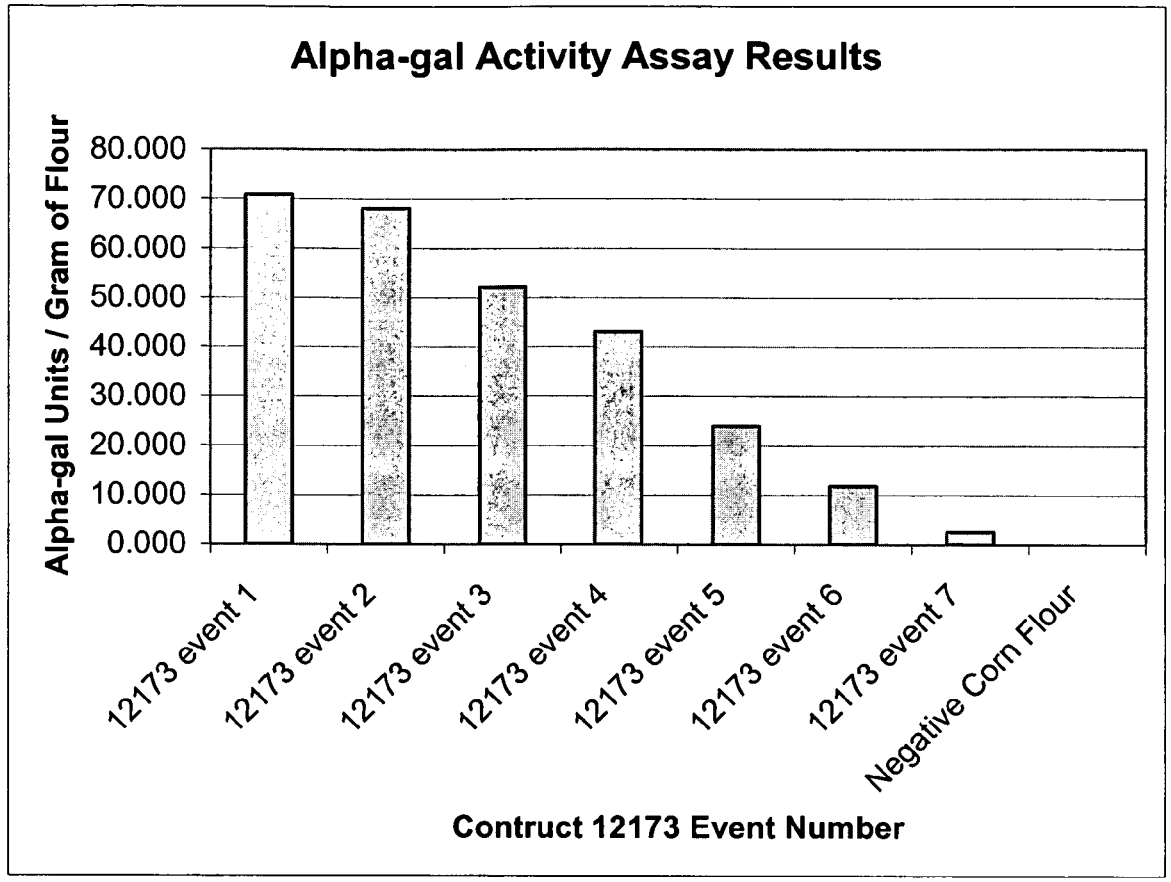
FIG. 4 is a bar graph depicting the results of assaying α-galactosidase activity in flour from transgenic corn seeds that contain a fusion protein including the Q protein signal sequence fused to α-galactosidase. Activity is expressed as α-galactosidase units per gram of flour from individual seeds.

The α-galactosidase activity resulting from the presence of construct 12173 containing the Q protein signal sequence showed the increased presence of the α-galactosidase protein. The levels ranged from 3 α-galactosidase units/gram of flour to 71 α-galactosidase units/gram of flour. The negative corn flour control had no α-galactosidase protein. These results are also presented in FIG. 4.

REFERENCES

The references listed below, as well as all references cited in the specification, are incorporated herein by reference in their entireties to the extent that they supplement, explain, provide a background for, or teach methodology, techniques, and/or compositions employed herein.

Allison R F, Johnston R E & Dougherty W G (1986) The nucleotide sequence of the coding region of tobacco etch virus genomic RNA: evidence for the synthesis of a single polyprotein. *Virology* 154:9–20.

Altschul S F, Gish W, Miller W, Myers E W & Lipman D J (1990) Basic Local Alignment Search Tool. *J Mol Biol* 215:403–410.

Aoyama T & Chua N-H (1997) A glucocorticoid-mediated transcriptional induction system in transgenic plants. *Plant J* 11:605–612.

Ausubel F M, Brent R, Kingston R E, Moore D D, Seidman J G, Smith J A & Struhl K (2002) *Short Protocols in Molecular Biology*, Fifth ed. Wiley, New York, N.Y., United States of America.

Ausubel F M, Brent R, Kingston R E, Moore D D, Seidman J G, Smith J A & Struhl K (2003) *Current Protocols in Molecular Biology*, John Wylie & Sons, Inc., New York, N.Y., United States of America.

Barany G & Merrifield R B (1980) Solid-Phase Peptide Synthesis, in *Peptides: Analysis, Synthesis, Biology, Vol. 2, Special Methods in Peptide Synthesis, Part A* (Gross E & Meienhofer J, eds) Academic Press, New York, N.Y., United States of America, pp. 3–284.

Bartlett S G, Grossman A R & Chua N-H (1982) in *Methods in Chloroplast Molecular Biology*, (Edelman M, Hallick R B & Chua N-H, eds.) Elsevier Biomedical Press, New York, N.Y., United States of America, pp. 1081–1091.

Batzer M A, Carlton J E & Deininger P L (1991) Enhanced evolutionary PCR using oligonucleotides with inosine at the 3'-terminus. *Nucleic Acid Res.* 19:5081.

Bevan M (1984) Binary *Agrobacterium* vectors for plant transformation. *Nucl. Acids Res* 12:8711–21.

Bevan M, Flavell R B & Chilton M D (1983) A chimeric antibiotic resistance gene as a selectable marker for plant cell transformation. *Nature* 304:184–187.

Binet M N Weil J H & Tessier L H (1991) Structure and expression of sunflower ubiquitin genes. *Plant Mol Biol* 17:395–407.

Blochinger K & Diggelmann H (1984) Hygromycin B phosphotransferase as a selectable marker for DNA transfer experiments with higher eukaryotic cells. *Mol Cell Biol* 4:2929–2931.

Boronat A, Martinez M C, Reina M, Puigdomenech P & Palau J (1986) Isolation and sequencing of a 28 kD glutelin-2 gene from maize. Common elements in the 5' flanking regions among zein and glutelin genes. *Plant Sci.* 47:95–102.

Bourouis M & Jarry B (1983) Vectors containing a prokaryotic dihydrofolate reductase gene transform *Drosophila* cells to methotrexate-resistance. *EMBO J.* 2:1099–1104.

Caddick M X, Greenland A J, Jepson I, Krause K P, Qu N, Riddell K V, Salter M G, Schuch W, Sonnewald U & Tomsett A B. (1998) An ethanol inducible gene switch for plants used to manipulate carbon metabolism. *Nat Biotechnol* 16:177–180.

Callis J, Fromm M & Walbot V (1987) Introns increase gene expression in cultured maize cells. *Genes Dev.* 1:1183–1200.

Callis J, Raasch J A & Vierstra R D (1990) Ubiquitin extension proteins of *Arabidopsis thaliana*. Structure, localization, and expression of their promoters in transgenic tobacco. *J Biol Chem* 265:12486–12493.

Casas A M, Kononowicz A K, Zehr U B, Tomes D T, Axtell J D, Butler L G, Bressan R A & Hasegawa P M (1993) Transgenic sorghum plants via microprojectile bombardment. *Proc Natl Acad Sci USA* 90:11212–6.

Chibbar R N, Kartha K K, Datla R SS, Leung N, Caswell K, Mallard C S & Steinhauer L (1993) The effect of different promoter-sequences on transient expression of gus reporter gene in cultured barley (*Hordeum vulgare* L.) cells. *Plant Cell Rep* 12:506–509.

Christensen A H & Quail P H (1989) Sequence analysis and transcriptional regulation by heat shock of polyubiquitin transcripts from maize. *Plant Mol Biol* 12:619–632.

Christou P, Ford T & Kofron M (1991) Production of transgenic rice (*Oryza sativa* L.) plants from agronomically important indica and japonica varieties via electric discharge particle acceleration of exogenous DNA into immature zygotic embryos. *Bio/Technology* 9: 957–962.

Clark M S (ed.) (1997) *Plant Molecular Biology: A Laboratory Manual*, Chapter 7, Springer-Verlag GmbH & Co. KG, Berlin, Germany.

Comai L, Larson-Kelly N, Kiser J, Mau C J, Pokalsky A R, Shewmaker C K, McBride K, Jones A & Stalker D M (1988) Chloroplast transport of a ribulose bisphosphate carboxylase small subunit-5-enolpyruvyl 3-phosphoshikimate synthase chimeric protein requires part of the mature small subunit in addition to the transit peptide. *J Biol Chem* 263:15104-15109.

Creighton T E (1984) *Proteins*, W H Freeman & Co., New York, N.Y., United States of America.

Datta S K, Peterhans A, Datta K & Potrykus I (1990) Genetically engineered fertile Indica-rice recovered from protoplasts. *Bio/Technology* 8:736–740.

de Framond A J (1991) A metallothionein-like gene from maize (*Zea mays*). Cloning and characterization. *FEBS Lett* 290:103–6.

Della-Cioppa G, Kishore G M, Beachy R N & Fraley R T (1987) Protein trafficking in plant cells. *Plant Physiol* 84:965–968.

Deutscher M P (1990) *Guide to Protein Purification*, Simon M I & Abelson J N (eds), *Meth Enzymol Volume* 182.

Dong, J J, Teng W M, Buchholz W G & Hall T C (1996). *Agrobacterium*-mediated transformation of javanica rice. *Mol Breeding* 2:267–276.

Elroy-Stein O, Fuerst T R & Moss B (1989) Cap-Independent Translation of mRNA Conferred by Encephalomyocarditis Virus 5' Sequence Improves the Performance of the Vaccinia Virus/Bacteriophage T7 Hybrid Expression System. *Proc Natl Acad Sci USA* 86:6126–6130.

Engelen A J, van der Heeft F C, Randsdorp P H, Somers W A, Schaefer J & van der Vat B J (2001) Determination of phytase activity in feed by a colorimetric enzymatic method: collaborative interlaboratory study. *J AOAC Int* 84:629–33.

EP 0 292 435
EP 0 332 104
EP 0 332 581
EP 0 342 926
EP 0 392 225

Firek S, Draper J, Owen M R, Gandecha A, Cockburn B & Whitelam G C (1993) Secretion of a functional single-chain Fv protein in transgenic tobacco plants and cell suspension cultures. *Plant Mol Biol* 22:129–142.

Fromm M E, Morrish F, Armstrong C, Williams R, Thomas J & Klein T M. (1990) Inheritance and expression of chimeric genes in the progeny of transgenic maize plants. *Biotechnology* (NY) 8:833–839.

Gallie D R, Kado C I, Hershey J WB, Wilson M A & Walbot V (1989) in *Molecular Biology of RNA* (Cech T R, ed.), Alan R. Liss, Inc., New York, N.Y., United States of America, pp. 237–256.

Gallie D R, Sleat D E, Watts J W, Turner P C & Wilson T M (1987) A comparison of eukaryotic viral 5'-leader sequences as enhancers of mRNA expression in vivo. *Nucl Acids Res* 15:8693–8711.

Goff S A, Ricke D, Lan T H, Presting G, Wang R L, Dunn M, Glazebrook J, Sessions A, Oeller P, Varma H, Hadley D, Hutchinson D, Martin C, Katagiri F, Lange B M, Moughamer T, Xia Y, Budworth P, Zhong J P, Miguel T, Paszkowski U, Zhang S P, Colbert M, Sun W L, Chen L L, Cooper B, Park S, Wood T C, Mao L, Quail P, Wing R, Dean R, Yu Y S, Zharkikh A, Shen R, Sahasrabudhe S, Thomas A, Cannings R, Gutin A, Pruss D, Reid J, Tavtigian S, Mitchell J, Eldredge G, Scholl T, Miller R M, Bhatnagar S, Adey N, Rubano T, Tusneem N, Robinson R, Feldhaus J, Macalma T, Oliphant A & Briggs, S (2002) A draft sequence of the rice genome (*Oryza sativa* L ssp *japonica*). *Science* 296:92–100.

Gordon-Kamm W J, Spencer T M, Mangano M L, Adams T R, Daines R J, Start W G, O'Brien J V, Chambers S A, Adams W R Jr., Willetts N G, Rice T B, Mackey C J, Krueger R W, Kausch A P & Lemaux P G (1990) Transformation of Maize Cells and Regeneration of Fertile Transgenic Plants. *Plant Cell* 2:603–618.

Green M R (2000) TBP-associated factors (TAFIIs): multiple, selective transcriptional mediators in common complexes. *Trends Biochem Sci* 25:59–63.

Gritz L & Davies J (1983) Plasmid-encoded hygromycin B resistance: the sequence of hygromycin B phosphotransferase gene and its expression in *Escherichia coli* and *Saccharomyces cerevisiae*. Gene 25:179–188.

Henikoff S & Henikoff J G (1992) Amino Acid Substitution Matrices from Protein Blocks. *Proc Natl Acad Sci U S A* 89:10915–10919.

Hiei Y, Komari T & Kubo T (1997) Transformation of rice mediated by *Agrobacterium tumefaciens*. *Plant Mol Biol* 35:205–18.

Hiei Y, Ohta S, Komari T & Kumashiro Y (1994) Efficient transformation of rice (*Oryza sativa* L.) mediated by Agrobacterium and sequence analysis of the boundaries of the T-DNA. *Plant J* 6(2):271–282.

Höfgen R & Willmitzer L (1988) Storage of competent cells for *Agrobacterium* transformation. *Nucl Acids Res* 16:9877.

Hudspeth R L & Grula J W (1989) Structure and expression of the maize gene encoding the phosphoenolpyruvate carboxylase isozyme involved in C4 photosynthesis. *Plant Molec Biol* 12:579–589.

Jobling S A & Gehrke L (1987) Enhanced translation of chimaeric messenger RNAs containing a plant viral untranslated leader sequence. *Nature* 325:622–625.

Karlin S & Altschul S F (1993) Applications and Statistics for Multiple High-Scoring Segments in Molecular Sequences. *Proc Natl Acad Sci U S A* 90:5873–5877.

Keegan L, Gill G & Ptashne M (1986) Separation of DNA binding from the transcription-activating function of a eukaryotic regulatory protein. *Science* 231:699–704.

Kellogg E A (1998) Relationships of cereal crops and other grasses. *Proc Natl Acad Sci USA* 95:2005–2010

Kempin S A, Liljegren S J, Block L M, Rounsley S D, Yanofsky M F & Lam E (1997) Targeted disruption in *Arabidopsis*. *Nature* 389:802–803.

Klein T M, Wolf E D, Wu R & Sanford J C (1987) High velocity microprojectiles for delivering nucleic acids into living cells. *Nature* 327:70–73.

Koehler S M & Ho T M (1990) Hormonal regulation, processing, and secretion of cysteine proteinases in barley aleurone layers. *Plant Cell* 2:769–783.

Kong P & Steinbiss H H (1998) Complete nucleotide sequence and analysis of the putative polyprotein of maize dwarf mosaic virus genomic RNA (Bulgarian isolate). *Arch Virol* 143:1791–1799.

Koziel M G, Beland G L, Bowman C, Carozzi N B, Crenshaw R, Crossland L, Dawson J, Desai N, Hill M, Kadwell S, Launis L, Lewis K, Maddox D, McPherson K, Meghji M R, Merlin E, Rhodes R, Warren G W, Wright M & Evola S V (1993) Field performance of elite transgenic maize plants expressing an insecticidal protein derived from *Bacillus thuringiensis*. *Bio/Technology* 11:194–200.

Kuchler R J (1997) *Biochemical Methods in Cell Culture and Virology*, Dowden, Hutchinson and Ross, Inc., Stroudsburg, Pa., United States of America.

Kyte J & Doolittle R F (1982) A Simple Method for Displaying the Hydropathic Character of a Protein. *J Mol Biol* 157:105–132.

Lebel E, Heifetz P, Thorne L, Uknes S, Ryals J & Ward E (1998) Functional analysis of regulatory sequences controlling PR-1 gene expression in *Arabidopsis*. *Plant J* 16:223–233.

Liebl W, Wagner B & Schellhase J (1998) Properties of an alpha-galactosidase, and structure of its gene galA, within an alpha- and beta-galactoside utilization gene cluster of the hyperthermophilic bacterium *Thermotoga maritima*. *Syst Appl Microbiol* 21: 1–11.

Logemann J, Lipphardt S, Lorz H, Hauser I, Willmitzer L & Schell J (1989) 5' upstream sequences from the wun1 gene are responsible for gene activation by wounding in transgenic plants. *Plant Cell* 1:151–158.

Lommel S A, Kendall T L, Xiong Z & Nutter R C (1991) Identification of the maize chlorotic mottle virus capsid protein cistron and characterization of its subgenomic messenger RNA. *Virology* 81:382–385.

Macejak D G & Sarnow P (1991) Internal initiation of translation mediated by the 5' leader of a cellular mRNA. *Nature* 353:90–94.

Mayo O (1987) *The Theory of Plant Breeding*, Second Edition, Clarendon Press, New York, N.Y., United States of America.

McBride K E, Schaaf D J, Daley M & Stalker D M (1994) Controlled expression of plastid transgenes in plants based on a nuclear DNA-encoded and plastid-targeted T7 RNA polymerase. *Proc Natl Acad Sci USA* 91:7301–7305.

McBride K E & Summerfelt K R (1990) Improved binary vectors for *Agrobacterium*-mediated plant transformation. *Plant Mol Biol* 14: 269–276.

McElroy D, Blowers A D, Jenes B & Wu R (1991) Construction of expression vectors based on the rice actin 1 (Act1) 5' region for use in monocot transformation. *Mol. Gen. Genet.* 231:150–160.

McElroy D, Zhang W, Cao J & Wu R (1990) Isolation of an efficient actin promoter for use in rice transformation. *Plant Cell* 2:163–71.

Merrifield R B (1963) Solid Phase Peptide Synthesis. I. The Synthesis of a Tetrapeptide *J Am Chem Soc* 85:2149–54.

Messing J & Vieira J (1982) A new pair of M13 vectors for selecting either DNA strand of double-digest restriction fragments. *Gene* 19:259–268.

Mettler I J (1987) A simple and rapid method for minipreparation of DNA from tissue-cultured plant cells *Plant Mol Biol Reporter* 5:346–349.

Miao Z H & Lam E (1995) Targeted disruption of the TGA3 locus in *Arabidopsis thaliana*. *Plant J* 7:359–365.

Mukumoto F, Hirose S, Imaseki H & Yamazaki K (1993) DNA sequence requirement of a TATA element-binding protein from *Arabidopsis* for transcription in vitro. *Plant Mol Biol* 23: 995–1003.

Murashige T & Skoog F (1962) A revised medium for rapid growth and bioassays with tobacco tissue culture. *Physiologia Plantarum* 15: 473–497 (1962)

Needleman S B & Wunsch C D (1970) A General Method Applicable to the Search for Similarities in the Amino Acid Sequence of Two proteins. *J Mol Biol* 48:443–453.

Negrotto D, Jolley M, Beer S, Wenck A R & Hansen G (2000) The use of phosphomannose-isomerase as a selection marker to recover transgenic maize plant (*Zea may* L.) via *Agrobacterium* transformation. *Plant Cell Reports* 19:798–803. Norris S R, Meyer S E & Callis J (1993) The intron of *Arabidopsis thaliana* polyubiquitin genes is conserved in location and is a quantitative determinant of chimeric gene expression. *Plant Mol Biol* 21:895–906.

Ohtsuka E, Matsuki S, Ikehara M, Takahashi Y & Matsubara K (1985) An alternative approach to deoxyoligonucleotides as hybridization probes by insertion of deoxyinosine at ambiguous codon positions. *J. Biol. Chem.* 260:2605–2608.

Paszkowski J, Bauer M, Bogucki A & Potrykus 1 (1988) Gene targeting in plants. *EMBO J.* 7:4021–26.

Paszkowski J, Shillito R D, Saul M, Mandak V, Hohn T, Hohn B & Potrykus I (1984) Direct gene transfer to plants. *EMBO J.* 3:2717–2722.

Paterson A H (1996) The DNA Revolution, in *Genome Mapping in Plants*, Chapter 2, (Paterson A H, ed.), Academic Press/R.G. Lands Co., Austin, Tex., United States of America.

PCT International Patent Application Publication WO 93/07278

PCT International Patent Application Publication WO 93/21335

PCT International Patent Application Publication WO 94/00977

PCT International Patent Application Publication WO 97/32011

PCT International Patent Application Publication WO 03/57248

Pearson W R & Lipman D J (1988) Improved Tools for Biological Sequence Comparison. *Proc Natl Acad Sci U S A* 85:2444–2448.

Picard D, Salser S J & Yamamoto K R (1988) A movable and regulable inactivation function within the steroid binding domain of the glucocorticoid receptor. *Cell* 54:1073–1080.

Potrykus I, Paszkowski J, Saul M W, Petruska J & Shillito R D (1985) Molecular and general genetics of a hybrid foreign gene introduced into tobacco by direct gene transfer. *Mol Gen Genet* 199:169–177.

Prat S, Cortadas J, Puigdomenech P & Palau J (1985) Nucleic acid (cDNA) and amino acid sequences of the maize endosperm protein glutelin-2. *Nucl. Acid Res.* 13:1493–1504.

Reed J N, Privalle L S, Powell M J, Meghji M, Dawson J, Dunder E M, Suttie J, Wenck A, Launis K, Kramer C, Chang Y, Hansen G & Wright M (2001) Phosphomannose isomerase: An efficient selectable marker for plant transformation. *In Vitro Cell Dev Biol-Plant* 37:127–132.

Reich T J, Iyer V N & Miki B L (1986) Efficient transformation of alfalfa protoplasts by the intranuclear microinjection of Ti-plasmids. *Bio/Technology* 4:1001–1004.

Reiter R S, Young R M & Scolnik P A (1992) Genetic Linkage of the *Arabidopsis* Genome: Methods for Mapping with Recombinant Inbreds and Random Amplified Polymorphic DNAs (RAPDs), in *Methods in Arabidopsis Research*, World Scientific Press, River Edge, N.J., United States of America.

Rogers J C, Dean D & Heck G R (1985) Aleurain: a barley thio]protease closely related to mammalian cathepsin H. *Proc. Natl. Acad. Sci. USA* 82:6512–6516.

Rohrmeier T & Lehle L (1993) WIP1, a wound-inducible gene from maize with homology to Bowman-Birk proteinase inhibitors. *Plant Mol Biol* 22:783–792.

Rossolini G M, Cresti S, Ingianni A, Cattani P, Riccio M L & Satta G (1994) Use of deoxyinosine-containing primers vs degenerate primers for polymerase chain reaction based on ambiguous sequence information. *Mol Cell Probes* 8:91–98.

Roth B A, Goff S A, Klein T M & Fromm M E (1991) C1- and R-dependent expression of the maize Bz1 gene requires sequences with homology to mammalian myb and myc binding sites. *Plant Cell* 3:317–325.

Rothstein S J, Lahners K N, Lotstein R J, Carozzi N B, Jayne S M & Rice D A (1987) Promoter cassettes, antibiotic-resistance genes, and vectors for plant transformation. *Gene* 53:153–161.

Sambrook J & Russell D W (2001) *Molecular Cloning: A Laboratory Manual*, 3rd ed. Cold Spring Harbor Laboratory Press, Cold Spring Harbor, N ewYork, United States of America.

Schmidhauser T J & Helinski D R (1985) Regions of broad-host-range plasmid RK2 involved in replication and stable maintenance in nine species of gram-negative bacteria. *J Bacteriol* 164:446–455.

Schocher R J, Shillito R D, Saul M W, Paszkowski J & Potrykus 1 (1986) Co-transformation of foreign genes into plants. *Bio/Technology* 4:1093–1096.

Schultz B et al. (1998) T-DNA tagging in *Arabidopsis thaliana*: Cloning by gene disruption, in *Plant Molecular Biology Manual* (2nd edition, Gelvin S B, Schilperoort R A & Verma D PS, eds.) Kluwer Academic Publishers, New York, N.Y., United States of America.

Scopes R (1982) *Protein Purification: Principles and Practice*, Springer-Verlag, New York, N.Y., United States of America.

Sherman F, Fink G R & Hicks J (1982) *Methods in Yeast Genetics*, Cold Spring Harbor Laboratory Press, Cold Spring Harbor, N.Y., United States of America, Shimamoto K, Terada R, Izawa T & Fujimoto H (1989) Fertile transgenic rice plants regenerated from transformed protoplasts. *Nature* 338:274–276.

Shinshi H, Neuhas J M, Ryals J & Meins F Jr. (1990) Structure of a tobacco endochitinase gene: evidence that different chitinase genes can arise by transposition of sequences encoding a cysteine-rich domain. *Plant Mol Biol* 14:357–368.

Silhavy T J, M. L. Berman, and L. W. Enquist (1984) *Experiments with Gene Fusions*, Cold Spring Harbor Laboratory, Cold Spring Harbor, N.Y., United States of America.

Singh D P (1986) *Breeding for Resistance to Diseases and Insect Pests*, Springer-Verlag, New York, N.Y., United States of America.

Skuzeski J M, Nichols L M & Gesteland R F (1990) Analysis of leaky viral translation termination codons in vivo by transient expression of improved beta-glucuronidase vectors. *Plant Mol Biol* 15:65–79.

Smith T F & Waterman M (1981) Comparison of Biosequences. *Adv Appl Math* 2:482–489.

Song R, Llaca V & Messing J (2001) Mosaic organization of orthologous sequences in grass genomes. *Genome Res* 12:1549–1555.

Southern J A, Young D F, Heaney F, Baumgartner W K, Randall R E (1991) Identification of an epitope on the P and V proteins of simian virus 5 that distinguishes between two isolates with different biological characteristics. *J Gen Virol* 72:1551–7.

Spencer T M, Gordon-Kamm W J, Daines R J, Start W & Lemaux P (1990). *Theor Appl Genet* 79:625–631.

Stewart J M & Young J D (1984) *Solid Phase Peptide Synthesis*, $2^{nd}$ ed. Pierce Chemical Co., Rockford, Ill., United States of America.

Svab Z, Hajdukiewicz P & Maliga P (1990) Stable transformation of plastids in higher plants. *Proc Natl Acad Sci USA* 87:8526–8530.

Svab Z & Maliga P (1993) High-frequency plastid transformation in tobacco by selection for a chimeric aadA gene. *Proc Natl Acad Sci USA* 90:913–917.

Taylor M, Vasil V & Vasil I K (1993) Enhanced gus gene expression in cereal grass cell suspensions and immature embryos using the maize ubiquitin-based plasmid pAHC25. *Plant Cell Rep* 12:491–495.

Thompson C J, Movva N R, Tizard R, Crameri R, Davies J E, Lauwereys M & Botterman J (1987) Characterization of the herbicide-resistance gene bar from *Streptomyces hygroscopicus*. *EMBO J.* 6:2519–2523.

Tijssen P (1993) *Laboratory Techniques in Biochemistry and Molecular Biology-Hybridization with Nucleic Acid Probes*. Elsevier, New York, N.Y., United States of America.

Torrent M, Alvarez I, Geli M I, Dalcol I & Ludevid D (1997) Lysine-rich modified gamma-zeins accumulate in protein bodies of transiently transformed maize endosperms. *Plant Mol Biol* 34:139–149.

Triezenberg S J, Kingsbury R C & McKnight S L (1988) Functional dissection of VP16, the trans-activator of herpes simplex virus immediate early gene expression. *Genes Dev* 2:718–729.

Uknes S, Mauch-Mani B, Moyer M, Potter S, Williams S, Dincher S, Chandler D, Slusarenko A, Ward E & Ryals J (1992) Acquired resistance in *Arabidopsis*. *Plant Cell* 4:645–656.

Unger E A, Hand J M, Cashmore A R & Vasconcelos A C (1989) Isolation of a cDNA encoding mitochondrial citrate synthase from *Arabidopsis thaliana*. *Plant Mol Biol* 13:411–418.

U.S. Pat. No. 4,554,101
U.S. Pat. No. 4,940,935
U.S. Pat. No. 4,945,050
U.S. Pat. No. 5,036,006
U.S. Pat. No. 5,100,792
U.S. Pat. No. 5,188,642
U.S. Pat. No. 5,466,785
U.S. Pat. No. 5,501,967
U.S. Pat. No. 5,523,311
U.S. Pat. No. 5,591,616
U.S. Pat. No. 5,614,395
U.S. Pat. No. 5,639,949
U.S. Pat. No. 5,767,378
U.S. Pat. No. 5,994,629
U.S. Pat. No. 6,369,298

Van den Broeck G, Timko M P, Kausch A P, Cashmore A R, Van Montagu M & Herrera-Estrella L (1985) Targeting of a foreign protein to chloroplasts by fusion to the transit peptide from the small subunit of ribulose 1,5-bisphosphate carboxylase. *Nature* 313:358–363.

Vasil V, Castillo A M, Fromm M E & Vasil I K (1992) Herbicide resistant fertile transgenic wheat plants obtained by microprojectile bombardment of regenerable embryogenic callus. *Bio/Technology* 10:667–674.

Vasil V, Srivastava V, Castillo A M, Fromm M R & Vasil I K (1993) Rapid production of transgenic plants by direct bombardment of cultured immature embryos. *Bio/Technology* 11:1553–1558.

Vitale A, Smaniotto E, Longhi R & Galante E (1982) Reduced soluble proteins associated with maize endosperm protein bodies. *J. Exp. Bot.* 33:439–448.

Wallace J C, Galili G, Kawata E E, Cuellar R E, Shotwell M A & Larkins B A (1988) Aggregation of lysine-containing zeins into protein bodies in *Xenopus* oocytes. *Science* 240:662–664.

Warner S A, Scott R, Draper J (1993) Isolation of an asparagus intracellular PR gene (AoPR1) wound-responsive promoter by the inverse polymerase chain reaction and its characterization in transgenic tobacco. *Plant J* 3:191–201.

Wasmann C C, Reiss B, Bartlett S G & Bohnert H J (1986) The importance of the transit peptide and the transported protein for protein import into chloroplasts. *Mol Gen Genet* 205:446–453.

Weeks J T, Anderson O D & Blechl A E (1993) Rapid Production of Multiple Independent Lines of Fertile Transgenic Wheat (*Triticum aestivum*). *Plant Physiol* 102:1077–1084.

Welsh J R (1981) *Fundamentals of Plant Genetics and Breeding*, John Wiley & Sons, New York, N.Y., United States of America.

White J, Chang S Y & Bibb M J (1990) A cassette containing the bar gene of *Streptomyces hygroscopicus*: a selectable marker for plant transformation. *Nucl Acids Res* 18:1062.

Wood D R (ed.) (1983) *Crop Breeding*, American Society of Agronomy, Madison, Wis., United States of America.

Wricke G & Weber W E (1986) *Quantitative Genetics and Selection Plant Breeding*, Walter de Gruyter and Co., Berlin, Germany.

Wyss M, Pasamontes L, Friedlein A, Remy R, Tessier M, Kronenberger A, Middendorf A, Lehmann M, Schnoebelen L, Rothlisberger U, Kusznir E, Wahl G, Muller F, Lahm H W, Vogel K & van Loon A P (1999) Biophysical characterization of fungal phytases (myo-inositol hexakisphosphate phosphohydrolases): molecular size, glycosylation pattern, and engineering of proteolytic resistance. *Appl Environ Microbiol* 65:359–66.

Xu D, McElroy D, Thornburg R W & Wu R (1993) Systemic induction of a potato pin2 promoter by wounding, methyl jasmonate, and abscisic acid in transgenic rice plants. *Plant Mol Biol* 22:573–588.

Zhang H M, Yang H, Rech E L, Golds T J, Davis A S, Mulligan B J, Cocking E C & Davey M R (1988) Transgenic rice plants produced by electroporation-mediated plasmid uptake into protoplasts. *Plant Cell Reports* 7: 379–384.

Zhao Z Y, Cai T, Tagliani L, Miller M, Wang N, Pang H, Rudert M, Schroeder S, Hondred D, Seltzer J & Pierce D (2000) *Agrobacterium*-mediated sorghum transformation. *Plant Mol Biol* 44:789–98.

Zhu T, Peterson D J, Tagliani L, St Clair G, Baszczynski C L & Bowen B (1999) Targeted manipulation of maize genes in vivo using chimeric RNA/DNA oligonucleotides. *Proc Natl Acad Sci USA* 96:8768–8773.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for expressing a nucleotide sequence in a plant, the method comprising:
   (a) operably linking the nucleotide sequence to a promoter comprising SEQ ID NO: 6 to produce an expression cassette; and
   (b) generating a transgenic plant comprising the expression cassette, whereby the nucleotide sequence is expressed in the plant.

2. The method of claim 1, wherein the generating comprises transforming a plant cell with the expression cassette and regenerating the plant from the transfomed plant cell.

3. The method of claim 2, wherein the transforming is by biolistic transformation of a vector comprising the expression cassette.

4. The method of claim 3, wherein the vector is a binary *Agrobacterium* expression vector.

5. The method of claim 1, wherein the nucleotide sequence encodes a polypeptide selected from the group consisting of carbohydrases, cellulases, hemicellulases, pectinases, isomerases, lyases, proteases, heat shock proteins, chaperonins, phytases, insecticidal proteins, antimicrobial proteins, α-amylases, glucoamylases, glucanases, glucosidases, xylanases, ferulic acid esterases, galactosidases, pectinases, and chymosin.

6. The method of claim 1, wherein the plant is selected from the group consisting of rice, maize, wheat, barley, oats, rye, millet, sorghum, triticale, secale, einkom, spelt, emmer, teff, milo, flax, gramma grass, *Tripsacum*, and *teosinte*.

7. An isolated nucleic acid molecule comprising SEQ ID NO: 6.

8. An expression cassette comprising SEQ ID NO: 6.

9. A recombinant vector comprising the expression cassette of claim 8.

10. A bacterial or plant cell comprising the expression cassette of claim 8.

11. A transgenic plant comprising the expression cassette of claim 8.

12. The tranagenic plant of claim 11, wherein the plant is a monocot.

13. The tranagenic plant of claim 12, wherein the monocot is selected from the group consisting of rice, maize, wheat, barley, oats, rye, millet, sorghum, triticale, secale, einkorn, spelt, emmer, teff, milo, flax, gramma grass, Tripsacum, and teosinte.

14. The transgenic plant of claim 11 wherein the plant is selected from the group consisting of rice, wheat, barley, rye, maize, potato, canola, soybean, sunflower, carrot, sweet potato, sugarbeet, bean, pea, chicory, lettuce, cabbage, cauliflower; broccoli, turnip, radish, spinach, asparagus, onion, garlic, eggplant, pepper, celery, squash, pumpkin, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane.

15. The tranagenic plant of claim 14, wherein the plant is maize.

16. The transgenic plant of claim 11, wherein the expression cassette is expressed in a seed and a polypeptide encoded by the nucleotide sequence is located within a protein body of a cell of the seed.

17. A method of producing a heterologous polypeptide in a plant cell, the method comprising:
   (a) generating a plant cell comprising a nucleotide sequence encoding the heterologous polypeptide operably linked to SEQ ID NO: 6; and
   (b) expressing in the plant cell the nuoleotide sequence encoding the heterologous polypeptide,
   whereby the heterologous polypeptide is produced in the plant cell.

18. The method of claim 17, wherein the generating comprises transforming the plant cell with an expression cassette comprising the nucleotide sequence encoding the heterologous polypeptide.

19. The method of claim 18, wherein the transforming is by biolistic transformation of a vector comprising the expression cassette.

20. The method of claim 19, wherein the vector is a binary *Agrobacterium* expression vector.

21. The method of claim 17, wherein the nucleotide sequence encodes a polypeptide selected from the group consisting of carbohydrases, cellulases, hemicellulases, pectinases, isomerases, lyases, proteases, heat shock proteins, chaperonins, phytases, insecticidal proteins, antimicrobial proteins, α-amylases, glucoamylases, glucanases, glucosidases, xylanases, ferulic acid esterases, galactosidases, pectinases, and chymosin.

22. The method of claim 17, wherein the plant is selected from the group consisting of rice, maize, wheat, bailey, oats, rye, millet, sorghum, triticale, secale, einkorn, spelt, emmer, teff, milo, flax, gramma grass, Tripsacum, and teosinte.

23. The method of claim 17, further comprising regenerating a plant from the plant cell.

24. The method of claim 17, further comprising isolating the polypeptide from the plant.

25. The method of claim 24, wherein the polypeptide is located within a protein body of the plant cell.

* * * * *